(12) United States Patent
Shanjani et al.

(10) Patent No.: US 11,304,778 B2
(45) Date of Patent: Apr. 19, 2022

(54) INTRAORAL APPLIANCES WITH PROXIMITY AND CONTACT SENSING

(71) Applicant: Align Technology, Inc., San Jose, CA (US)

(72) Inventors: Yaser Shanjani, Milpitas, CA (US); Bruce Cam, San Jose, CA (US); Jun Sato, San Jose, CA (US); John Y. Morton, San Jose, CA (US); Victor Chen, Mountain View, CA (US); Chunhua Li, Cupertino, CA (US); Allen R. Boronkay, San Jose, CA (US); Srinivas Kaza, Mountain View, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/146,465

(22) Filed: Jan. 11, 2021

(65) Prior Publication Data
US 2021/0244501 A1  Aug. 12, 2021

Related U.S. Application Data

(63) Continuation of application No. 16/680,393, filed on Nov. 11, 2019, now Pat. No. 10,888,396, which is a
(Continued)

(51) Int. Cl.
*A61C 7/00* (2006.01)
*H04B 5/00* (2006.01)
(Continued)

(52) U.S. Cl.
CPC ............ *A61C 7/002* (2013.01); *A61B 5/0015* (2013.01); *A61B 5/0816* (2013.01); *A61B 5/389* (2021.01);
(Continued)

(58) Field of Classification Search
CPC ... A61B 5/0015; A61B 5/0488; A61B 5/0816; A61B 5/4818; A61B 5/682; A61C 7/002;
(Continued)

(56) References Cited

U.S. PATENT DOCUMENTS

| 3,797,115 A | 3/1974 | Cohen et al. |
| 4,094,068 A | 6/1978 | Schinhammer |

(Continued)

FOREIGN PATENT DOCUMENTS

| CN | 104127253 A | 11/2014 |
| WO | 03096922 A1 | 11/2003 |
| WO | 2014143911 A1 | 9/2014 |

OTHER PUBLICATIONS

Dental Monitoring, "Basics: How to put your Cheek Retractor? (Dental Monitoring Tutorial)", https://lwww.youtube.com/watch?v=6K1HXw4Kq3c, May 27, 2016.
(Continued)

*Primary Examiner* — Nader Bolourchi
(74) *Attorney, Agent, or Firm* — Shay Glenn LLP

(57) ABSTRACT

Detection of placement of dental aligners in patient mouth on teeth for indication of wearing compliance. Described herein are apparatuses and methods for detecting wearing, including compliance. In some variations these apparatuses and methods may include a sensor configured to detect deflection of the one or more deflectable structures. In some variations, these apparatuses and methods may include a proximity sensor coupled to the appliance shell and configured to generate sensor data when in proximity with intraoral tissue.

17 Claims, 55 Drawing Sheets

Related U.S. Application Data continuation of application No. 15/625,872, filed on Jun. 16, 2017, now Pat. No. 10,470,847.

(60) Provisional application No. 62/351,516, filed on Jun. 17, 2016, provisional application No. 62/351,391, filed on Jun. 17, 2016, provisional application No. 62/483,283, filed on Apr. 7, 2017.

(51) Int. Cl.
| | |
|---|---|
| A61B 5/389 | (2021.01) |
| A61B 5/00 | (2006.01) |
| A61B 5/08 | (2006.01) |
| A61C 7/08 | (2006.01) |
| H04Q 9/00 | (2006.01) |

(52) U.S. Cl.
CPC ............ *A61B 5/4818* (2013.01); *A61B 5/682* (2013.01); *A61C 7/08* (2013.01); *H04B 5/00* (2013.01); *H04B 5/0031* (2013.01); *H04B 5/0056* (2013.01); *H04B 5/0081* (2013.01); *H04Q 9/00* (2013.01); *H04Q 2209/43* (2013.01); *H04Q 2209/50* (2013.01)

(58) Field of Classification Search
CPC .......... A61C 7/08; H04B 5/00; H04B 5/0031; H04B 5/0056; H04B 5/0081; H04Q 2209/43; H04Q 2209/50; H04Q 9/00
See application file for complete search history.

(56) References Cited

U.S. PATENT DOCUMENTS

| | | |
|---|---|---|
| 4,129,946 A | 12/1978 | Kennedy |
| 4,179,812 A | 12/1979 | White |
| 4,204,325 A | 5/1980 | Kaelble |
| 4,368,040 A | 1/1983 | Weissman |
| 4,971,557 A | 11/1990 | Martin |
| 5,636,736 A | 6/1997 | Jacobs et al. |
| 5,680,874 A | 10/1997 | Takuno |
| 5,820,368 A | 10/1998 | Wolk |
| 6,102,701 A | 8/2000 | Engeron |
| 6,183,248 B1 | 2/2001 | Chishti et al. |
| 6,213,767 B1 | 4/2001 | Dixon et al. |
| 6,386,864 B1 | 5/2002 | Kuo |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,769,913 B2 | 8/2004 | Hurson |
| 6,783,604 B2 | 8/2004 | Tricca |
| 6,790,035 B2 | 9/2004 | Tricca et al. |
| 6,814,574 B2 | 11/2004 | Abolfathi et al. |
| 6,843,370 B2 | 1/2005 | Tuneberg |
| 6,947,038 B1 | 9/2005 | Anh et al. |
| 6,988,893 B2 | 1/2006 | Haywood |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,841,464 B2 | 11/2010 | Cinader, Jr. et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,197,252 B1 | 6/2012 | Harrison, III |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,419,428 B2 | 4/2013 | Lawrence |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,753,114 B2 | 6/2014 | Vuillemot |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 9,901,332 B2 * | 2/2018 | Jessop ..................... A61C 5/90 |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 2002/0192617 A1 | 12/2002 | Phan et al. |
| 2003/0060532 A1 | 3/2003 | Subelka et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0040551 A1 | 2/2005 | Biegler et al. |

(56) References Cited

U.S. PATENT DOCUMENTS

| | | |
|---|---|---|
| 2005/0042577 A1 | 2/2005 | Kvitrud et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0116561 A1* | 6/2006 | Tricca ............... A61B 5/0088 600/309 |
| 2006/0199142 A1 | 9/2006 | Liu et al. |
| 2006/0234179 A1 | 10/2006 | Wen et al. |
| 2007/0218422 A1 | 9/2007 | Ehrenfeld |
| 2007/0263226 A1 | 11/2007 | Kurtz et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0062394 A1 | 3/2010 | Jones et al. |
| 2010/0129763 A1 | 5/2010 | Kuo |
| 2010/0151404 A1 | 6/2010 | Wu et al. |
| 2010/0217130 A1 | 8/2010 | Weinlaender |
| 2011/0179851 A1* | 7/2011 | Mack ..................... G01L 1/26 73/1.79 |
| 2011/0212420 A1 | 9/2011 | Vuillemot |
| 2011/0269092 A1 | 11/2011 | Kuo et al. |
| 2012/0028210 A1 | 2/2012 | Hegyi et al. |
| 2013/0070926 A1 | 3/2013 | Eun |
| 2014/0067334 A1 | 3/2014 | Kuo |
| 2014/0342301 A1 | 11/2014 | Fleer et al. |
| 2015/0102941 A1 | 4/2015 | Keech et al. |
| 2015/0216641 A1 | 8/2015 | Popa-Simil et al. |
| 2015/0265376 A1 | 9/2015 | Avi |
| 2015/0366637 A1 | 12/2015 | Kopelman et al. |
| 2015/0366638 A1 | 12/2015 | Avi et al. |
| 2016/0193014 A1 | 7/2016 | Morton et al. |
| 2016/0242870 A1 | 8/2016 | Matov et al. |
| 2016/0242871 A1 | 8/2016 | Morton et al. |
| 2017/0007359 A1 | 1/2017 | Avi et al. |
| 2017/0007360 A1 | 1/2017 | Kopelman et al. |
| 2017/0007361 A1 | 1/2017 | Allen et al. |
| 2017/0007366 A1 | 1/2017 | Kopelman et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2017/0319296 A1 | 11/2017 | Webber et al. |
| 2018/0078334 A1 | 3/2018 | Lotan et al. |
| 2018/0153648 A1 | 6/2018 | Shanjani et al. |
| 2018/0168776 A1 | 6/2018 | Webber |
| 2018/0177570 A1 | 6/2018 | Alauddin et al. |
| 2018/0228359 A1 | 8/2018 | Meyer et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Bruce et al. |
| 2019/0021817 A1 | 1/2019 | Sato et al. |
| 2019/0026599 A1 | 1/2019 | Salah et al. |
| 2019/0029775 A1 | 1/2019 | Morton et al. |
| 2019/0029784 A1 | 1/2019 | Moalem et al. |
| 2019/0046297 A1 | 2/2019 | Kopelman et al. |
| 2019/0069975 A1 | 3/2019 | Cam et al. |
| 2019/0099129 A1 | 4/2019 | Kopelman et al. |
| 2019/0099241 A1* | 4/2019 | Way ..................... A61C 7/36 |
| 2019/0125494 A1 | 5/2019 | Li et al. |
| 2019/0125497 A1 | 5/2019 | Mitra et al. |
| 2019/0152152 A1 | 5/2019 | O'Leary et al. |
| 2019/0175304 A1 | 6/2019 | Morton et al. |
| 2019/0231477 A1 | 8/2019 | Shanjani et al. |
| 2019/0262101 A1 | 8/2019 | Yaser et al. |
| 2019/0269482 A1 | 9/2019 | Shanjani et al. |
| 2019/0298494 A1 | 10/2019 | Webber et al. |
| 2019/0314119 A1 | 10/2019 | Kopelman et al. |
| 2019/0338067 A1 | 11/2019 | Robert et al. |
| 2019/0343606 A1 | 11/2019 | Wu et al. |
| 2020/0000553 A1 | 1/2020 | Svetlana et al. |
| 2020/0086553 A1 | 3/2020 | Mojdeh et al. |
| 2020/0100864 A1 | 4/2020 | Yuxiang et al. |
| 2020/0100865 A1 | 4/2020 | Yuxiang et al. |
| 2020/0100866 A1 | 4/2020 | Viktoria et al. |
| 2020/0100871 A1 | 4/2020 | Yuxiang et al. |
| 2020/0155276 A1 | 5/2020 | Bruce et al. |
| 2020/0188062 A1 | 6/2020 | Avi et al. |
| 2020/0214598 A1 | 7/2020 | Huizhong et al. |
| 2020/0214801 A1 | 7/2020 | Yuxiang et al. |
| 2020/0390523 A1 | 12/2020 | Jun et al. |
| 2021/0078357 A1 | 3/2021 | Venkatasanthanam et al. |

OTHER PUBLICATIONS

Dental Monitoring, Dental monitoring tutorial, 1 page (Screenshot), retrieved from the internet (https:www.youtube.com/watch?v=Dbe3udOf9_c), Mar. 18, 2015.

Eclinger Selfie, Change your smile, 1 page (screenshot), retrieved from the internet https://play.google.com/store/apps/details?id=parkelict.ecligner), on Feb. 13, 2018.

* cited by examiner

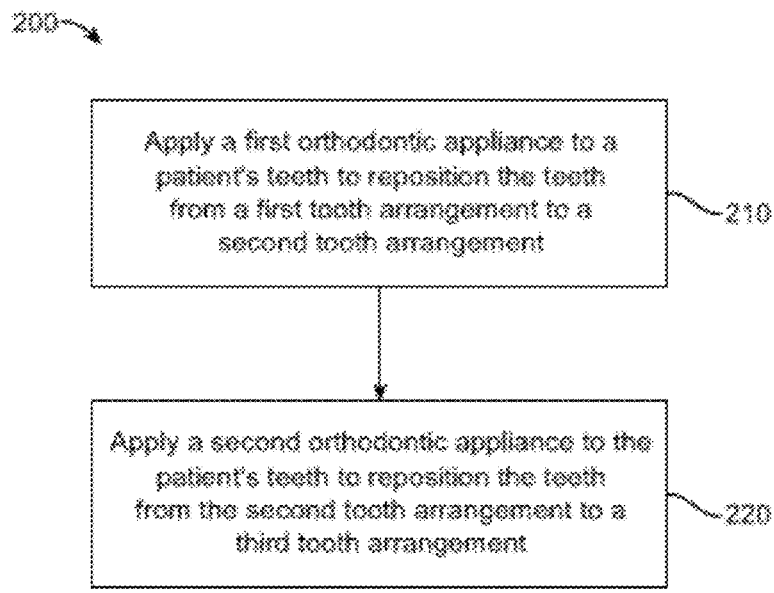

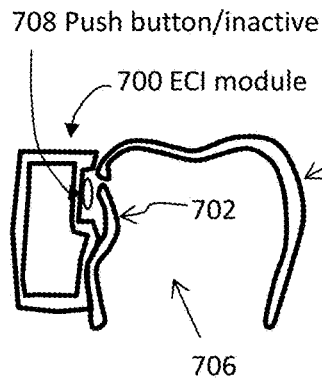
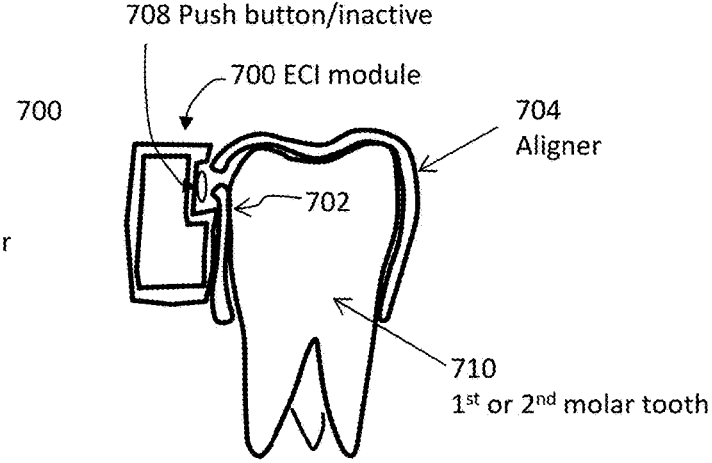
FIG. 7A
FIG. 7B
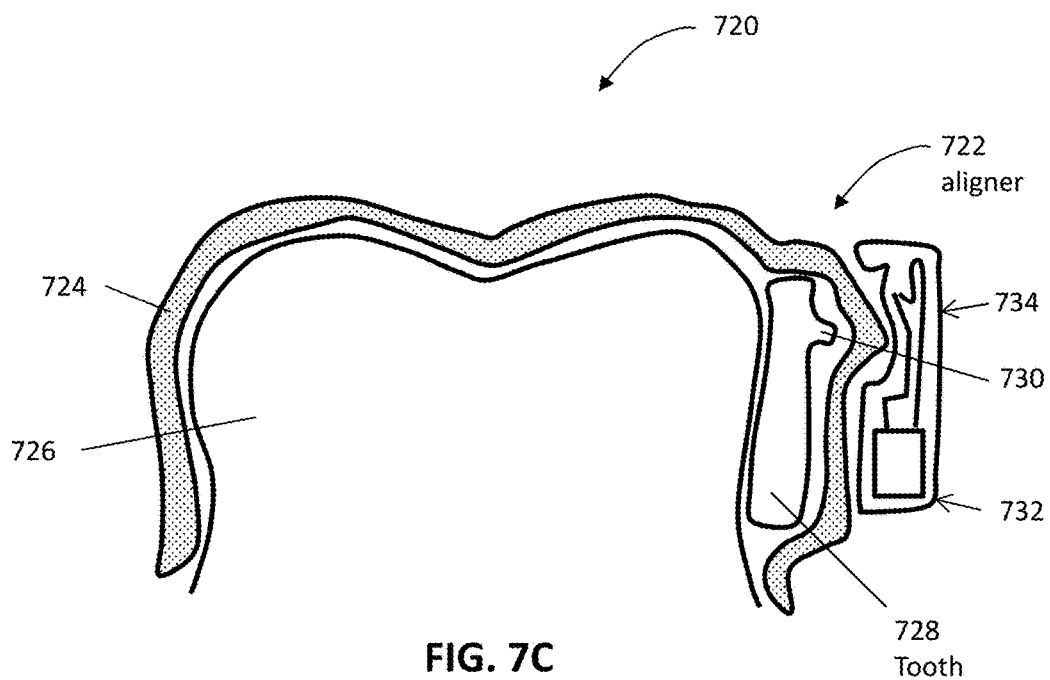
FIG. 7C

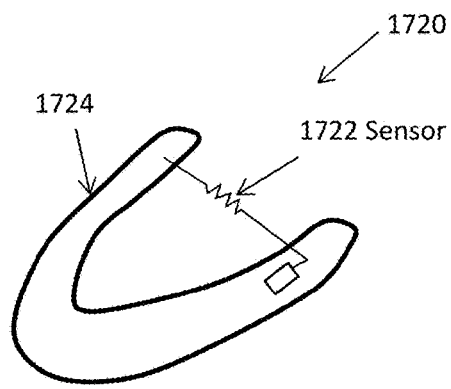
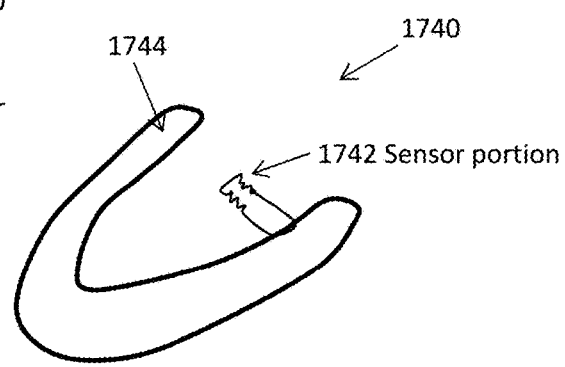
FIG. 17B                FIG. 17C
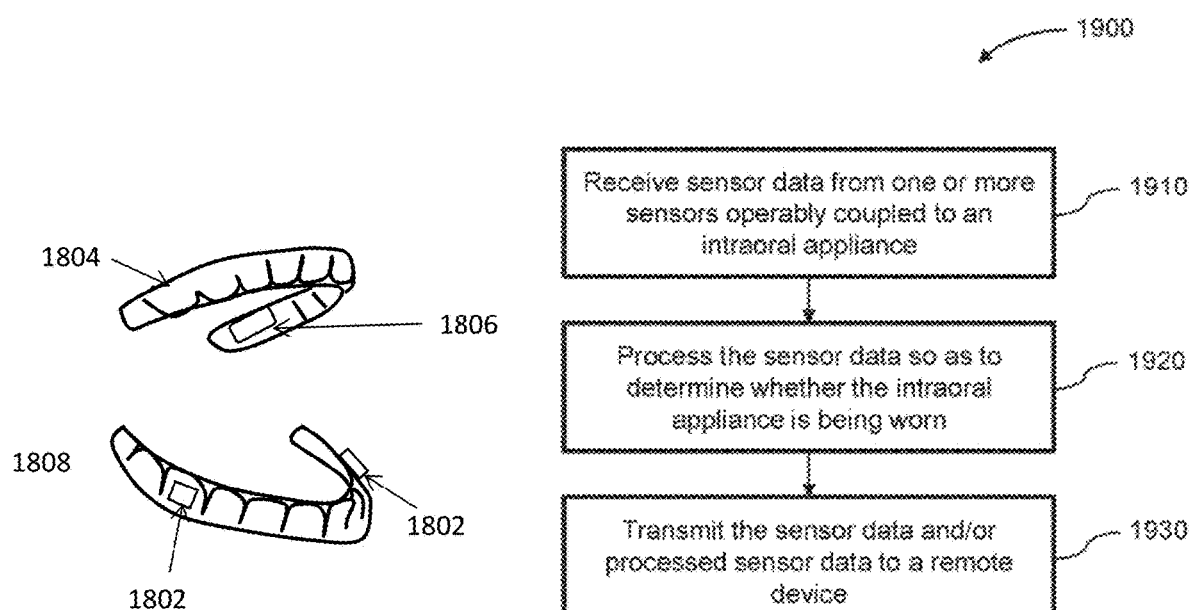
FIG. 18                FIG. 19

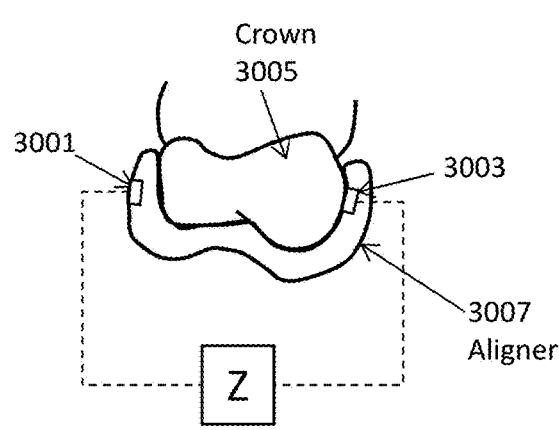
FIG. 30A
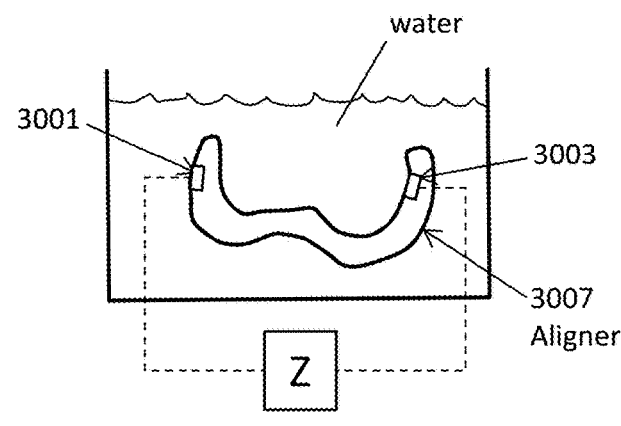
FIG. 30B
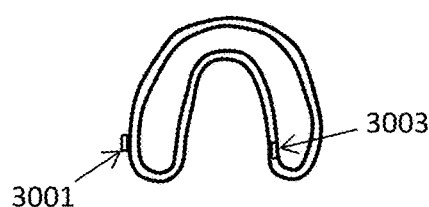
FIG. 30C
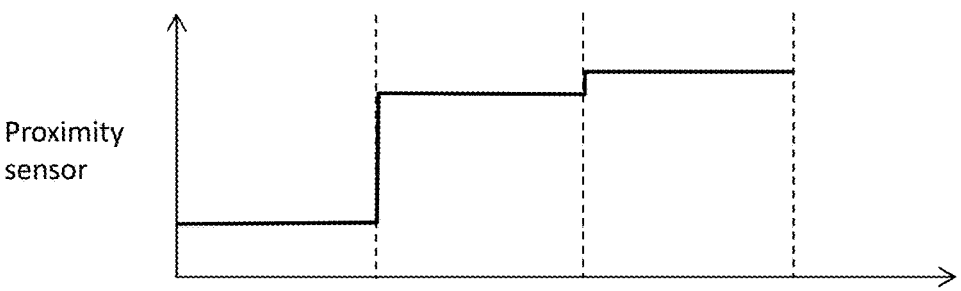
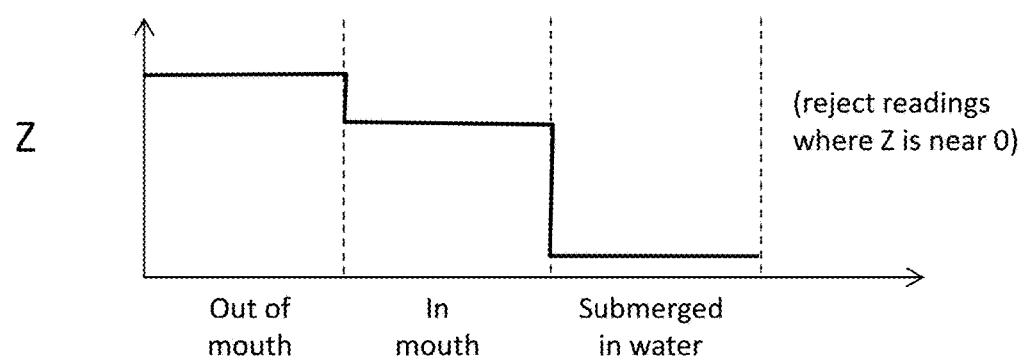
FIG. 30D

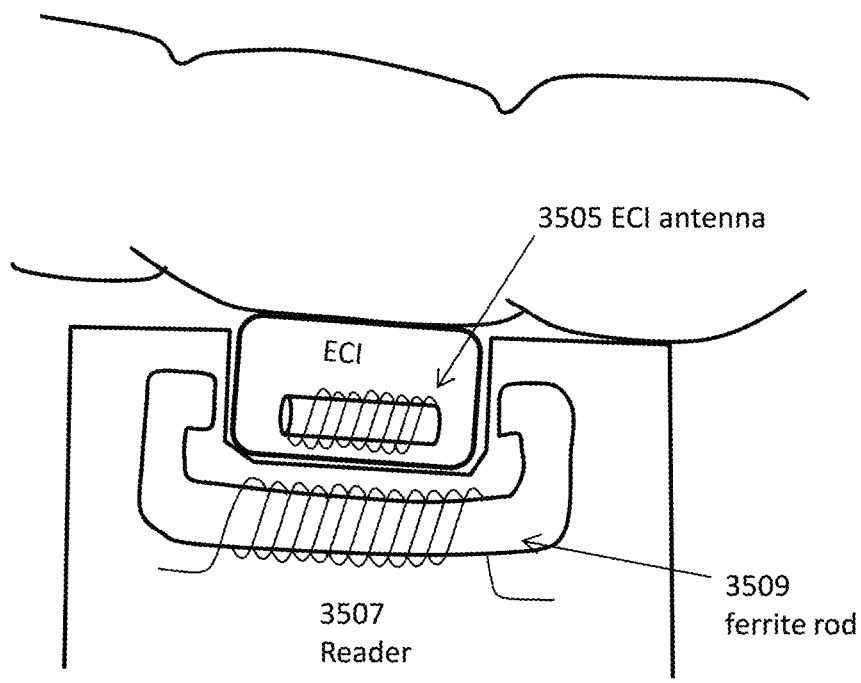
FIG. 35B
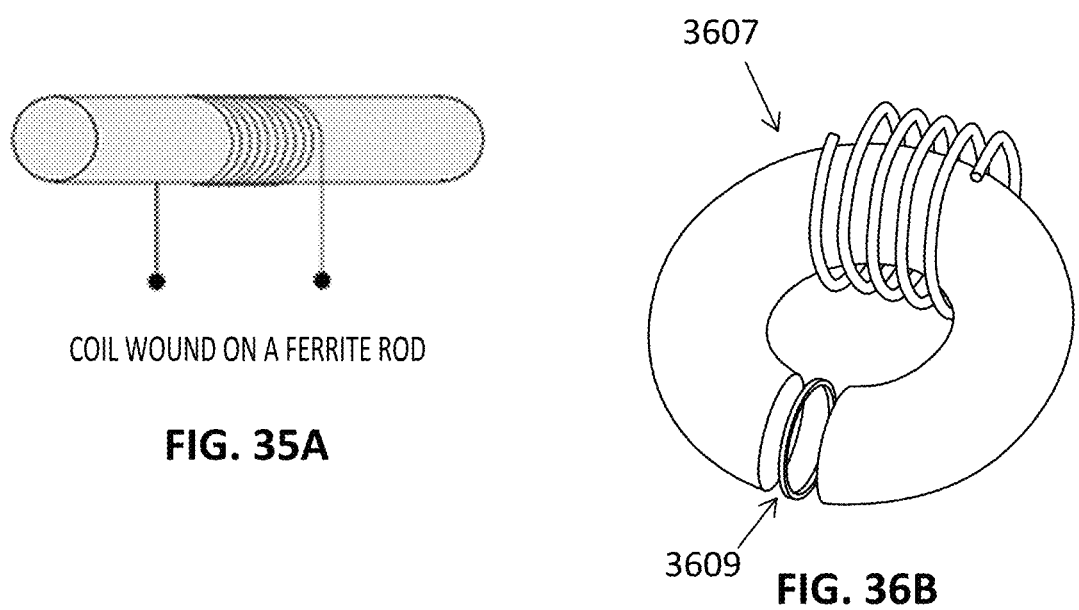
FIG. 35A
FIG. 36B

INTRAORAL APPLIANCES WITH PROXIMITY AND CONTACT SENSING

CLAIM OF PRIORITY

This application is a continuation of U.S. patent application Ser. No. 16/680,393, filed Nov. 11, 2019, titled "INTRAORAL APPLIANCES WITH PROXIMITY AND CONTACT SENSING," now U.S. Pat. No. 10,888,396, which is a continuation of U.S. patent application Ser. No. 15/625,872, filed Jun. 16, 2017, titled "INTRAORAL APPLIANCES WITH SENSING," now U.S. Pat. No. 10,470,847, which claims priority to U.S. Provisional Patent Application No. 62/351,516, filed Jun. 17, 2016, titled "EMBEDDED INTRAORAL SENSING FOR PHYSIOLOGICAL MONITORING AND TREATMENT WITH AN ORAL APPLIANCE," U.S. Provisional Patent Application No. 62/351,391, filed Jun. 17, 2016, titled "ELECTRONIC COMPLIANCE INDICATOR FOR INTRAORAL APPLIANCES," and U.S. Provisional Patent Application No. 62/483,283, filed Apr. 7, 2017, titled "WIRELESS ELECTRONIC COMPLIANCE INDICATOR, READER CASE AND USER INTERFACE FOR INTRAORAL APPLIANCES."

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan.

During orthodontic treatment with patient-removable appliances, the practitioner may rely on the patient to comply with the prescribed appliance usage. In some instances, a patient may not wear the orthodontic appliance as prescribed by the practitioner. Extended removal of the appliance, for any reason beyond what is recommended, may interrupt the treatment plan and lengthen the overall period of treatment. There is a need for methods and apparatuses that allow monitoring of the wearing and/or effects of intraoral appliances. Described herein are methods and apparatuses for performing such monitoring.

Obstructive sleep apnea (hereinafter "OSA") is a medical condition characterized by complete or partial blockage of the upper airway during sleep. The obstruction may be related to relaxation of soft tissues and muscles in or around the throat (e.g., the soft palate, back of the tongue, tonsils, uvula, and pharynx) during sleep. OSA episodes may occur multiple times per night and disrupt the patient's sleep cycle. Suffers of chronic OSA may experience sleep deprivation, excessive daytime sleepiness, chronic fatigue, headaches, snoring, and hypoxia.

Prior methods and apparatus for monitoring physiological characteristics of patients with conditions such as sleep disordered breathing can be less than ideal in at least some respects. It would be desirable to provide systems for monitoring physiological characteristics without requiring sensors placed outside of the intraoral cavity. For example, instead of sensors on the body of a patient, implanted within the patient, or disposed within the mouth but connected to external apparatus, it is preferred to have sensors that operate autonomously within the intraoral cavity of the patient. It would be helpful to provide intraoral appliances comprising embedded intraoral sensors, allowing autonomous monitoring of physiological characteristics of patients, thereby providing data useful in the diagnosis of sleep disorders and other oral- and airway-related disorders.

SUMMARY OF THE DISCLOSURE

Described herein are apparatuses, including devices and systems, including in particular appliances (e.g., orthodontic appliances) and methods for monitoring an orthodontic appliance, including, but not limited to monitoring patient compliance with orthodontic treatment. Monitoring may alternatively or additionally include monitoring status, monitoring wear of the appliance, monitoring the geographic/spatial location of the appliance, monitoring the environment of the appliance, etc. In some embodiments, an orthodontic appliance includes one or more sensors configured to obtain sensor data; these sensors may include those that are indicative of patient compliance (e.g., whether the patient is wearing the appliance). The appliance can include one or more processors operably coupled to the sensor(s) and configured to process the sensor data so as to generate patient compliance data, thus enabling electronic monitoring of patient compliance with a prescribed course of orthodontic treatment. Advantageously, the systems, methods, and devices herein may increase patient compliance and improve treatment efficacy, as well as provide patient data useful to the practitioner for designing and monitoring orthodontic treatments.

A device for monitoring usage of an intraoral appliance may include an appliance shell comprising a plurality of teeth receiving cavities; one or more sensors operably coupled to the appliance shell and configured to generate sensor data indicative of appliance usage by a patient; and a processor operably coupled to the one or more sensors and configured to process the sensor data so as to determine whether the intraoral appliance is being worn on the patient's teeth.

The apparatuses and methods described herein may be configured to detect ("smart detection") placement of aligners on a tooth or teeth and may be configured to differentiate from other, similar, events such as water immersion. Also described herein are methods and apparatuses that permit direct communication with cell phones for activation and retrieving data from monitor(s).

As mentioned, the methods and apparatuses described herein may generally be used with or as part of any monitoring devices for monitoring an orthodontic appliance. For example, described herein are Electronic Compliance Indicator (ECI) apparatuses that may be configured to record sensor data from subjects (e.g., patients) wearing or intended/intending to wear an orthodontic aligner such as a shell aligner. However, it should be understood that these methods and apparatuses are not limited to just monitoring compliance and operation on compliance data, but may be used for any type of data, and these monitoring apparatuses (including ECIs) may also be generically referred to as data loggers or embedded data loggers. Thus, in any of the description and examples provided herein, unless the context makes it clear otherwise, when an "ECI" apparatus is described, the apparatus may not be limited to compliance monitoring. Thus, for any of the description, examples, methods and apparatuses described herein, the term "ECI" should be understood to be more broadly referred to as a monitoring apparatus (MA) or performance monitoring apparatus (PMA), and not just an ECI.

For example, in any of these apparatuses, the data may be stored in physical memory on the monitoring apparatus (e.g., the ECI) and may be retrieved by another device in communication with the monitoring apparatus. Retrieval may be done wirelessly, e.g., using near-field communication (NFC) and/or Bluetooth (BLE) technologies to use a smartphone or other hand-held device to retrieve the data. Specifically described herein are monitoring apparatuses (including ECI apparatuses) and orthodontic aligners using them that include temperature and capacitive sensors, a CPU, a NFC communication module, an NFC antenna, a PCB and battery. Also described herein are cases or holders that may boost and/or relay the signals from the small monitoring apparatus to a handheld device such as a smartphone; such cases or holders may be referred to as NFC-BLE enabled Aligner cases.

A monitoring apparatus such as an electronic compliance indicator (ECI) apparatus configured to monitor usage of an intraoral appliance may include a housing enclosing a power source and monitoring circuitry, the monitoring circuitry comprising a processor, a memory, and one or more sensors; a removable mechanical activation interrupt between the power source and the processor, wherein the mechanical activation interrupt has a first position that breaks a connection between the power source and the monitoring circuitry so that no current flows between the power source and the monitoring circuitry and a second position in which there is an electrical connection between the monitoring circuity and the power source; and an elastomeric overmold encapsulating the housing.

The removable mechanical activation interrupt may comprise a magnetic switch, a removable activation rod, a pin, etc. Any of these apparatuses may include the dental appliance (e.g., an aligner such as a shell aligner) to which the monitoring apparatus (e.g., ECI) may be permanently or removably coupled.

In general, any of the monitoring apparatus (e.g., ECI apparatuses) may be sized to fit against or over one tooth. For example the housing may have a maximum diameter of 2 cm or less, 1.5 cm or less, 1.0 cm or less, 0.9 cm or less, 0.8 cm or less, 0.7 cm or less, 0.6 cm or less, etc.). The monitoring apparatus housing may generally be thin (e.g., 1.0 cm or less, 0.9 cm or less, 0.8 cm or less, 0.7 cm or less, 0.6 cm or less, 0.5 cm or less, 0.4 cm or less, etc.). In any of these apparatuses, the monitoring circuitry may be configured for a wired connection, e.g., may include a plurality of data electrodes external to the housing but encapsulated by the elastic overmold. The apparatus may configured to be connect to a plurality of metallic/conductive leads that pierce the (e.g., self-healing) overmold material to contact the otherwise covered contacts.

Also described herein are methods of activating a monitoring apparatus (such as an electronic compliance indicator or ECI) configured to monitor an intraoral appliance. For example, a method may include: moving a mechanical activation interrupt of the monitoring apparatus from a first position that breaks a connection between a power source and a monitoring circuitry of the monitoring apparatus such that no current flows between the power source and the monitoring circuitry to a second position in which there is an electrical connection between the monitoring circuity and the power source; inserting the monitoring apparatus, coupled to an orthodontic appliance, into a patient's oral cavity; and recording data from one or more sensors with the monitoring apparatus. Moving the mechanical activation interrupt may comprise: operating a magnetic switch by removing the monitoring apparatus from a packaging having a permanent magnet; inserting or removing an activation rod; and/or inserting or removing a pin. The method may also include coupling the monitoring apparatus to the orthodontic appliance. Inserting the monitoring apparatus may comprise inserting the monitoring apparatus coupled to a shell aligner. Recording data may comprise recording data from two or more sensors of the monitoring apparatus every 1 to every 30 minutes (e.g., every approximately 10 minutes).

Also described herein are monitoring apparatuses (e.g., electronic compliance indicator apparatuses) configured to monitor usage of an intraoral appliance and provide output via a removable wired connection. A monitoring apparatus may include: a housing enclosing a power source and monitoring circuitry, the monitoring circuitry comprising a processor, a memory, and one or more sensors; a self-healing elastomeric overmold encapsulating the housing; a plurality of data electrodes external to the housing but encapsulated by the elastic overmold; and an attachment configured to secure the monitoring apparatus to an orthodontic appliance. The apparatus may include the orthodontic appliance (e.g., a shell aligner). Any appropriate self-healing material may be used, including an electrically insulating polymeric material.

Also described herein are boosters and/or converters for transferring a signal (such as a NFC signal) from the monitoring apparatus to a signal that can be received by a smartphone, which typically has a much larger (and poorly matched/difficult to match) antenna for receiving the NFC from the monitoring apparatus device. For example, described herein are near field communication (NFC) to Bluetooth communication (BLE) signal coupler devices for relaying monitoring data from an orthodontic Monitoring Apparatus (monitoring apparatus, such as an ECI) to a handheld processor (such as a smartphone). These devices may include: a housing; a first antenna configured for NFC within the housing; a second antenna configured for BLE within the housing; a holder on the housing configured to hold the monitoring apparatus in alignment with the first antenna; and NFC to BLE transmission circuitry configured to receive data from the first antenna and to transmit data from the second antenna. The holder may comprise a case formed at least partially from the housing and configured to hold the monitoring apparatus (or the MA and dental appliance such as an aligner) within the case so that the monitoring apparatus is aligned with the first antenna. The NFC to BLE transmission circuitry may comprise a power source within the housing. The holder may include an indentation on the housing. The first antenna may comprise a trace antenna or a coil antenna; for example, the first antenna comprises a toroidal loop antenna having a gap.

Although the apparatuses and methods described herein include numerous examples of near field communication (NFC), including NFC-to-NFC communication, any of the methods and apparatuses described herein may be used with other types of wireless communication modes, including, without limitation, Wi-Fi, radio (RF, UHF, etc.), infrared (IR), microwave, Bluetooth (including Bluetooth low energy or BLE), magnetic field induction (including NFC), Wimax, Zigbee, ultrasound, etc. In particular, the methods and apparatuses described herein may include apparatuses that convert between these different wireless modes.

Also described herein are methods of relaying monitoring data from an orthodontic Monitoring Apparatus (such as an electronic compliance indicator apparatus) to a handheld processor. For example, a method may comprise: aligning a monitoring apparatus with a first antenna within a housing of a near field communication (NFC) to Bluetooth communication (e.g., BLE) signal coupler device; transmitting the monitoring data from the monitoring apparatus to the NFC to BLE signal coupler device by NFC; and retransmitting the monitoring data from the NFC to BLE signal coupler device via a Bluetooth signal to a handheld electronics device. The method may also include inserting the monitoring apparatus into the NFC to BLE signal coupler device, wherein the NFC to BLE signal coupler device is configured as a case configured to hold the monitoring apparatus (or MA and a dental appliance to which the monitoring apparatus is coupled). The method may also include receiving the Bluetooth signal in the handheld electronics device, wherein the handheld electronics device comprises a smartphone. The method may also include modifying the monitoring data before retransmitting the data. Transmitting the monitoring data may comprise receiving the NFC signal comprising the monitoring data on a first antenna of the NFC to BLE signal coupler device; alternatively or additionally, retransmitting the monitoring data may comprise transmitting the monitoring data as the Bluetooth data via a second antenna of the NFC to BLE signal coupler device configured for Bluetooth communication.

Also described herein are improved systems, methods, and apparatus for monitoring physiological characteristics of patients, including from a patient's airway. In many embodiments, an orthodontic appliance is provided. The orthodontic appliance comprises one or more intraoral sensors embedded within an appliance shell shaped to receive teeth. In some embodiments, the intraoral sensors comprise a transmitter and a receiver. In some embodiments, the intraoral sensors comprise a plurality of electrodes. The one or more intraoral sensors are coupled to one or more processors. The processors are configured to determine a characteristic of the patient's intraoral cavity or airway based on measurements from the intraoral sensors. In some cases, the measurements include electrical impedance measurements. In some cases, the measurements include return signals from the patient's intraoral cavity or airway in response to emitted signals from a transmitter. Monitoring the physiological characteristics of patients using the appliances disclosed herein allows more precise diagnosis of patient conditions such as OSA. Because the symptoms of diseases such as OSA manifest when the patient is unconscious, autonomous electronic monitoring with an intraoral appliance can provide patient data that would otherwise be difficult or impossible to obtain, thereby facilitating diagnosis and treatment of the underlying condition. The monitoring systems and methods disclosed herein can be combined with a treatment apparatus, such as an appliance applying tooth-moving forces or an appliance for increasing airway clearance in the treatment of OSA.

In one aspect, an apparatus for monitoring a physiological characteristic of a patient is provided. The apparatus comprises an intraoral appliance shaped to receive the patient's teeth. The appliance comprises a plurality of electrodes. The electrodes are positioned to make electrical contact with the patient's intraoral cavity when the intraoral appliance is worn by the patient. The appliance further comprises one or more processors configured to use the electrodes to measure an electrical impedance. The processor uses the measured electrical impedance to determine a physiological characteristic of the patient.

In another aspect, an apparatus for monitoring a characteristic of a patient's intraoral cavity or airway is provided. The apparatus comprises an intraoral appliance shaped to receive the patient's teeth and includes a transmitter and a receiver. The appliance may further comprise one or more processors configured to cause the transmitter to emit a signal within the patient's intraoral cavity; measure a signal returning from the patient's intraoral cavity or airway in response to the emitted signal using the receiver; and determine, based on the measured signal, the characteristic of the patient's intraoral cavity or airway.

Other objects and features of the present invention will become apparent by a review of the specification, claims, and appended figures.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 illustrates a method of orthodontic treatment using a plurality of appliances.

FIG. 3A schematically illustrates an example of a monitoring apparatus (shown as an ECI device).

FIGS. 7A and 7B illustrate an example of a monitoring device with a deflectable structure.

FIG. 7C shows an example of a monitoring device with a deflectable structure.

FIG. 17B illustrates an example of a monitoring device including a gas flow sensor.

FIG. 17C shows an example of a monitoring device including a gas flow sensor.

FIG. 18 illustrates an example of a monitoring device using motion sensing.

FIG. 19 illustrates an example of a method for monitoring usage of an intraoral appliance.

FIG. 30A shows an example of an ECI apparatus including a pair of guard electrodes; FIG. 30B illustrates the complex impedance of an ECI apparatus such as that shown in FIG. 30A when submerged in water; FIG. 30C is an example of an ECI apparatus including capacitance-sensing electrodes positioned at the end of the aligner appliance. FIG. 30D illustrates the interpretation of the capacitance-sensing electrode to distinguish false positives when determining if an appliance having an ECI apparatus such as that shown in FIG. 30A is being worn.

FIG. 31A is a top view with the case cover open. FIG. 31B shows a back view of the case of FIG. 31A, and FIG. 31C is a side view of the case of FIG. 31A. FIG. 31D is a top view of a prototype of the case shown in FIG. 31A.

FIG. 34B shows alternative variations of antennas on the aligner.

FIGS. 35A and 35B illustrate a coil antenna and the use of a coil antenna as part of a data reader to read data from an ECI, respectively.

FIG. 36B illustrates an example of a toroid loop antenna with a gap in the ferrite core that may be used as part of an NFC coupler, such as illustrated in FIG. 36A, for example.

DETAILED DESCRIPTION

Figures 1A, 1B, 1C, 1D:
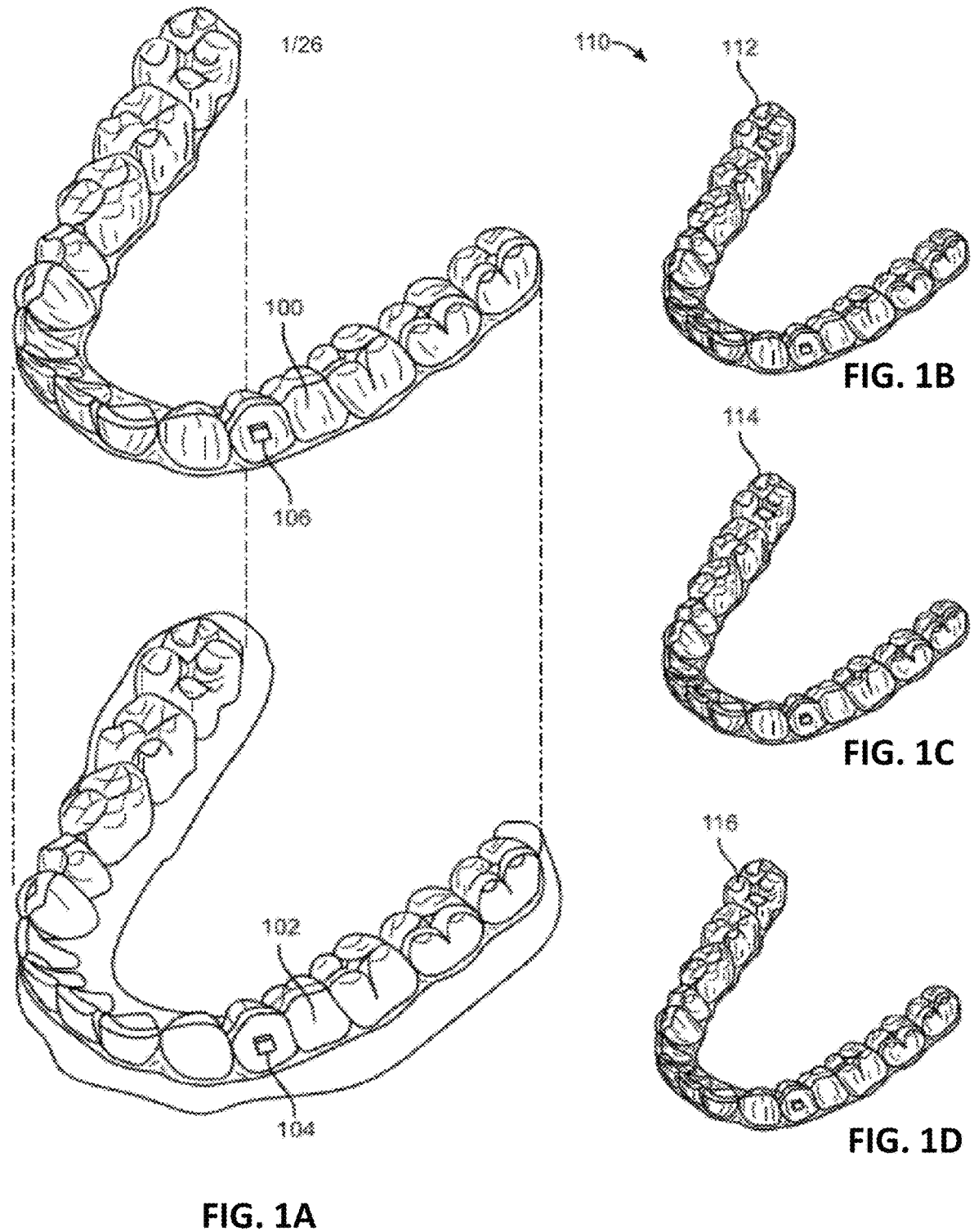
FIG. 1A illustrates an example of a tooth repositioning appliance.
FIGS. 1B-1D shows an example of a tooth repositioning system.

The monitoring apparatuses described herein may generally include Electronic Compliance Indicators (ECIs). An ECI may record sensor data from a subject wearing one or more dental appliances, such as dental/orthodontic aligners, including shell aligners. Data recorded by the ECI may be stored in physical memory on the ECI and may be retrieved by another device. In particular, the data described may be retrieved by a hand held electronics communication device such as a smartphone, tablet, or the like. The handheld electronics device may include a user interface to augment communication between the ECI and the device, and may provide feedback to the user (e.g., patient) and/or technician, physician, dentist, orthodontist, or other medical/dental practitioner. Once transmitted to the handheld device, the data may be processed (or further processed) and/or passed on to a remote processor, memory and/or server.

In particular, described herein are apparatuses for monitoring, including ECIs, that are very small and therefore use a relay, such as an appliance case or holder configured to operate as a relay. For example, described herein are apparatuses that use both NFC and BLE communication to transmit data between an ECI and a handheld electronic device (e.g., smartphone). Using NFC and BLE technologies may allow a smartphone to retrieve the data even from a very small ECI that includes only a small antenna, with a reasonably high accuracy and low power.

The apparatuses and methods described herein for monitoring treatment with removable intraoral appliances may generate sensor data related to usage of an intraoral appliance. The sensor data can be processed and analyzed to determine whether the patient is wearing the appliance in accordance with a prescribed treatment plan. Advantageously, the apparatuses and methods described herein provide an integrated electronic sensing and logging system capable of generating more reliable and accurate patient compliance data, which may be used by the treating practitioner to track patient behavior and improve treatment efficacy. Additionally, the monitoring apparatuses described herein may provide high value sensing data useful for appliance design. In some embodiments, the sensing data provided by the monitoring apparatuses described herein may be used as feedback to modify parameters of an ongoing orthodontic treatment, also known as adaptive closed-loop treatment planning.

The ECI apparatuses described herein may detect when the device is worn on a subject's tooth/teeth using any appropriate method, including one or more of those described herein. For example, an apparatuses for monitoring usage of an intraoral appliance (an ECI) may include one or more deflectable structures formed with or coupled to the intraoral appliance. The deflectable structure(s) can be shaped to be deflected when the intraoral appliance is worn on a patient's teeth. The device can comprise a sensor configured to generate sensor data indicative of deflection of the deflectable structure(s). Optionally, the device can comprise a processor operably coupled to the sensor and configured to process the sensor data so as to determine whether the intraoral appliance is being worn.

The intraoral appliance may comprise an appliance shell including a plurality of teeth receiving cavities. The deflectable structure(s) can be located near a tooth receiving cavity of the plurality of teeth receiving cavities so as to be deflected outward when a tooth is positioned within the tooth receiving cavity. The deflectable structure(s) can be formed in a wall of the tooth receiving cavity. The deflectable structure(s) can be deflected outward by at least 25 µm when the tooth is positioned within the tooth receiving cavity.

The deflectable structure(s) may comprise a deflected state when the intraoral appliance is being worn and a resting state when the intraoral appliance is not being worn, and the deflectable structure(s) interact with the sensor when in the deflected state. The sensor can comprise a mechanical switch and the deflectable structure(s) can engage the mechanical switch when in the deflected state. The sensor can comprise an optical switch and the deflectable structure(s) can activate the optical switch when in the deflected state.

The deflectable structure(s) may comprise a cantilever, dimple, concavity, flap, protrusion, or pop-out structure.

The apparatuses may further comprise a communication unit operably coupled to the sensor and configured to transmit one or more of the sensor data or the processed sensor data to a remote device. The sensor may be integrated with the intraoral appliance or coupled to a tooth. The processor may be integrated with the intraoral appliance or coupled to a tooth. Alternatively or additionally, the processor may be located external to the patient's intraoral cavity.

Any of the devices for monitoring usage of an intraoral appliance may comprise an appliance shell comprising a plurality of teeth receiving cavities and one or more proximity sensors operably coupled to the appliance shell and configured to generate sensor data when in proximity with intraoral tissue. The device can comprise a processor operably coupled to the one or more proximity sensors and configured to process the sensor data so as to determine whether the intraoral appliance is being worn on a patient's teeth.

The one or more proximity sensors may comprise one or more touch sensors (similarly the touch sensors described herein may be referred to as proximity sensors and/or proximity/touch sensors). The one or more touch sensors can comprise at least one capacitive touch sensor activated by charges associated with one or more of enamel, gingiva, oral mucosa, saliva, cheeks, lips, or tongue. The one or more touch sensors can comprise at least one capacitive touch sensor activate by positive charges associated with plaque or bacteria on the patient's teeth. The processor may optionally be configured to process the sensor data so as to determine an amount of bacteria on the patient's teeth. The one or more touch sensors can comprise at least one resistive touch sensor.

The one or more touch sensors may comprise at least one capacitive touch sensor configured to use one or more of enamel, gingiva, oral mucosa, saliva, cheeks, lips, or tongue as a ground electrode.

The one or more proximity sensors may comprise one or more of: a capacitive sensor, an eddy-current sensor, a magnetic sensor, an optical sensor, a photoelectric sensor, an ultrasonic sensor, a Hall Effect sensor, an infrared touch sensor, or a surface acoustic wave (SAW) touch sensor. The one or more proximity sensors may be configured to generate sensing data when in proximity to one or more of the patient's enamel, gingiva, oral mucosa, cheeks, lips, or tongue. The one or more proximity sensors may be integrated with the intraoral appliance, coupled to a tooth, or a combination thereof.

The processor may be integrated with the intraoral appliance or coupled to a tooth.

An apparatuses for monitoring usage of an intraoral appliance may include an appliance shell comprising a plurality of teeth receiving cavities and one or more vibration sensors operably coupled to the appliance shell and configured to generate sensor data of intraoral vibration patterns. The device can also comprise a processor operably coupled to the one or more vibration sensors and configured to process the sensor data so as to determine whether the intraoral appliance is being worn on a patient's teeth. The one or more vibration sensors comprise one or more of: a MEMS microphone, an accelerometer, or a piezoelectric sensor. The intraoral vibration patterns may be associated with one or more of: vibrations transferred to the patient's teeth via the patient's jaw bone, teeth grinding, speech, mastication, breathing, or snoring. The processor may determine whether the intraoral appliance is being worn by comparing the intraoral vibration patterns to patient-specific intraoral vibration patterns. The one or more vibration sensors may be integrated with the intraoral appliance, coupled to a tooth, or a combination thereof. The processor is integrated with the intraoral appliance or coupled to a tooth.

The various embodiments described herein can be used in combination with various types of intraoral appliances worn in a patient's mouth. The intraoral appliance may be an orthodontic appliance, such as an aligner or wire-and-bracket appliance, used to reposition one or more of the patient's teeth to a desired arrangement, e.g., to correct a malocclusion. Alternatively or additionally, the intraoral appliance may be used to maintain one or more of the patient's teeth in a current arrangement, such as a retainer. Other examples of intraoral appliances suitable for use in conjunction with the embodiments herein include sleep apnea treatment devices (e.g., mandibular advancement devices or splints), night guards (e.g., for treating bruxism), mouth guards, and palatal expanders.

Appliances having teeth receiving cavities that receive and reposition teeth, e.g., via application of force due to appliance resiliency, are generally illustrated with regard to FIG. 1A. FIG. 1A illustrates an exemplary tooth repositioning appliance or aligner 100 that can be worn by a patient in order to achieve an incremental repositioning of individual teeth 102 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the URL "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

FIGS. 1B-1D illustrate an example of a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 1A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

FIG. 2 illustrates a method 200 of orthodontic treatment using a plurality of appliances, in accordance with embodiments. The method 200 can be practiced using any of the appliances or appliance sets described herein. In step 210, a first orthodontic appliance is applied to a patient's teeth in order to reposition the teeth from a first tooth arrangement to a second tooth arrangement. In step 220, a second orthodontic appliance is applied to the patient's teeth in order to reposition the teeth from the second tooth arrangement to a third tooth arrangement. The method 200 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

An intraoral appliance can be operably coupled to a monitoring device (also referred to herein as an "electronic compliance indicator") configured to provide data related to appliance usage and/or patient compliance, such as data indicative of whether the appliance is being worn, the amount of time the appliance is worn, and/or interaction between the appliance and the intraoral cavity (e.g., contact between the appliance and intraoral tissues, force and/or pressure applied by the appliance to intraoral tissues). Alternatively or in combination, the monitoring device can be configured to provide data indicative of one or more characteristics of the patient's intraoral cavity or a portion thereof (e.g., teeth, gingiva, palate, lips, tongue, cheeks, saliva, airway), such as temperature, color, sound, vibration, motion, pH, conductivity, charge, resistance, capacitance, humidity, or gas flow. The characteristics of the patient's intraoral cavity can optionally be used to determine appliance usage and/or patient compliance, as discussed in greater detail herein.

The monitoring devices described herein can be designed for use in the patient's intraoral cavity. For example, the dimensions of a monitoring device may be limited in order to avoid patient discomfort and/or facilitate integration into an intraoral appliance as discussed below. In some embodiments, a monitoring device has a height or thickness less than or equal to about 1.5 mm, or less than or equal to about 2 mm. In some embodiments, a monitoring device has a length or width less than or equal to about 4 mm, or less than or equal to about 5 mm. The shape of the monitoring device can be varied as desired, e.g., circular, ellipsoidal, triangular, square, rectangular, etc. For instance, in some embodiments, a monitoring device can have a circular shape with a diameter less than or equal to about 5 mm.

A relatively thin and flexible monitoring device can be used to provide a larger surface area while reducing patient discomfort. In some embodiments, the monitoring devices herein are sized to conform to a surface of a tooth crown (e.g., a buccal, lingual, and/or occlusal surface of a tooth crown). For example, a monitoring device having dimensions of about 10 mm by about 5 mm can be used to cover a buccal surface of a molar crown. As another example, a monitoring device having dimensions of about 10 mm by about 20 mm can be used to cover the buccal, occlusal, and lingual surfaces of a tooth crown. A monitoring device can be in contact with a crown of a single tooth, or with crowns of a plurality of teeth, as desired.

The other properties of the monitoring device (e.g., volume, weight) can be designed in order to reduce patient discomfort. For instance, the weight of a monitoring device can be selected not to exceed a level that would exert undesirable forces on the underlying teeth.

FIG. 3A schematically illustrates a monitoring device 300 (e.g., an ECI). The monitoring device 300 can be used in combination with any embodiment of the systems and devices described herein, and the components of the monitoring device 300 are equally applicable to any other embodiment of the monitoring devices described herein. The monitoring device 300 can be implemented as an application-specific integrated circuit (ASIC) including one or more of the following components: a processor 302, a memory 304, one or more sensors 306, a clock 308, a communication unit 310, an antenna 312, a power management unit 314, or a power source 316. The processor 302 (e.g., a central processing unit (CPU), microprocessor, field programmable gate array (FPGA), logic or state machine circuit, etc.), also referred to herein as a controller, can be configured to perform the various methods described herein. The memory 304 encompasses various types of memory known to those of skill in the art, such as RAM (e.g., SRAM, DRAM), ROM (EPROM, PROM, MROM), or hybrid memory (e.g., flash, NVRAM, EEPROM), and the like. The memory 304 can be used to store instructions executable by the processor 302 to perform the methods provided herein. Additionally, the memory can be used to store sensor data obtained by the sensor(s) 306, as discussed in greater detail below.

The monitoring device 300 can include any number of sensors 306, such as one, two, three, four, five, or more sensors. In some embodiments, the use of multiple sensors provides redundancy to increase the accuracy and reliability of the resultant data. Some or all of the sensors 306 can be of the same type. Some or all of the sensors 306 can be of different types. Examples of sensor types suitable for use in the monitoring devices described herein include: touch or tactile sensors (e.g., capacitive, resistive), proximity sensors, audio sensors (e.g., microelectromechanical system (MEMS) microphones), color sensors (e.g., RGB color sensors), electromagnetic sensors (e.g., magnetic reed sensors, magnetometer), light sensors, force sensors (e.g., force-dependent resistive materials), pressure sensors, temperature sensors, motion sensors (e.g., accelerometers, gyroscopes), vibration sensors, piezoelectric sensors, strain gauges, pH sensors, conductivity sensors, gas flow sensors, gas detection sensors, humidity or moisture sensors, physiological sensors (e.g., electrocardiography sensors, bio-impedance sensors, photoplethysmography sensors, galvanic skin response sensors), or combinations thereof. In some embodiments, the sensors herein can be configured as a switch that is activated and/or deactivated in response to a particular type of signal (e.g., optical, electrical, magnetic, mechanical, etc.).

A sensor 306 can be located at any portion of an intraoral appliance, such as at or near a distal portion, a mesial portion, a buccal portion, a lingual portion, a gingival portion, an occlusal portion, or a combination thereof. A sensor 306 can be positioned near a tissue of interest when the appliance is worn in the patient's mouth, such as near or adjacent the teeth, gingiva, palate, lips, tongue, cheeks, airway, or a combination thereof. For example, when the appliance is worn, the sensor(s) 306 can cover a single tooth, or a portion of a single tooth. Alternatively, the sensor(s) 306 can cover multiple teeth or portions thereof. In embodiments where multiple sensors 306 are used, some or all of the monitoring devices can be located at different portions of the appliance and/or intraoral cavity. Alternatively, some or all of the sensor 306 can be located at the same portion of the appliance and/or intraoral cavity.

An analog-to-digital converter (ADC) (not shown) can be used to convert analog sensor data into digital format, if desired. The processor 302 can process the sensor data obtained by the sensor(s) 306 in order to determine appliance usage and/or patient compliance, as described herein. The sensor data and/or processing results can be stored in the memory 304. Optionally, the stored data can be associated with a timestamp generated by the clock 308 (e.g., a real-time clock or counter).

The monitoring device 300 may include a communication unit 310 configured to transmit the data stored in the memory (e.g., sensor data and/or processing results) to a remote device. The communication unit 310 can utilize any suitable communication method, such as wired or wireless communication methods (e.g., RFID, near-field communication, Bluetooth, ZigBee, infrared, etc.). The communication unit 310 can include a transmitter for transmitting data to the remote device and an antenna 312. Optionally, the communication unit 310 includes a receiver for receiving data from the remote device. In some embodiments, the communication channel utilized by the communication unit 310 can also be used to power the device 300, e.g., during data transfer or if the device 300 is used passively.

The remote device can be any computing device or system, such as a mobile device (e.g., smartphone), personal computer, laptop, tablet, wearable device, etc. Optionally, the remote device can be a part of or connected to a cloud computing system ("in the cloud"). The remote device can be associated with the patient, the treating practitioner, medical practitioners, researchers, etc. In some embodiments, the remote device is configured to process and analyze the data from the monitoring device 300, e.g., in order to monitor patient compliance and/or appliance usage, for research purposes, and the like.

The monitoring device 300 can be powered by a power source 316, such as a battery. In some embodiments, the power source 316 is a printed and/or flexible battery, such as a zinc-carbon flexible battery, a zinc-manganese dioxide printed flexible battery, or a solid-state thin film lithium phosphorus oxynitride battery. The use of printed and/or flexible batteries can be advantageous for reducing the overall size of the monitoring device 300 and avoiding patient discomfort. For example, printed batteries can be fabricated in a wide variety of shapes and can be stacked to make three-dimensional structures, e.g., to conform the appliance and/or teeth geometries. Likewise, flexible batteries can be shaped to lie flush with the surfaces of the appliance and/or teeth. Alternatively or in combination, other types of batteries can be used, such as supercapacitors. In some embodiments, the power source 316 can utilize lower power energy harvesting methods (e.g., thermodynamic, electrodynamic, piezoelectric) in order to generate power for the monitoring device 300. Optionally, the power source 316 can be rechargeable, for example, using via inductive or wireless methods. In some embodiments, the patient can recharge the power source 316 when the appliance is not in use. For example, the patient can remove the intraoral appliance when brushing the teeth and place the appliance on an inductive power hub to recharge the power source 316.

Optionally, the monitoring device 300 can include a power management unit 314 connected to the power source 316. The power management unit 314 can be configured to control when the monitoring device 300 is active (e.g., using power from the power source 316) and when the device 300 is inactive (e.g., not using power from the power source 316). In some embodiments, the monitoring device 300 is only active during certain times so as to lower power consumption and reduce the size of the power source 316, thus allowing for a smaller monitoring device 300. In some embodiments, the monitoring device 300 includes an activation mechanism (not shown) for controlling when the monitoring device 300 is active (e.g., powered on, monitoring appliance usage) and when the monitoring device 300 is dormant (e.g., powered off, not monitoring appliance usage). The activation mechanism can be provided as a discrete component of the monitoring device 300, or can be implemented by the processor 302, the power management unit 314, or a combination thereof. The activation mechanism can be used to reduce the amount of power used by the monitoring device 300, e.g., by inactivating the device 300 when not in use, which can be beneficial for reducing the size of the power supply 316 and thus the overall device size.

In some embodiments, the monitoring device 300 is dormant before being delivered to the patient (e.g., during storage, shipment, etc.) and is activated only when ready for use. This approach can be beneficial in conserving power expenditure. For example, the components of the monitoring device 300 can be electrically coupled to the power source 316 at assembly, but may be in a dormant state until activated, e.g., by an external device such as a mobile device, personal computer, laptop, tablet, wearable device, power hub etc. The external device can transmit a signal to the monitoring device 300 that causes the activation mechanism to activate the monitoring device 300. As another example, the activation mechanism can include a switch (e.g., mechanical, electronic, optical, magnetic, etc.), such that the power source 316 is not electrically coupled to the other components of the monitoring device 300 until the switch is triggered. For example, in some embodiments, the switch is a reed switch or other magnetic sensor that is held open by a magnet. The magnet can be removably attached to the monitoring device 300, or may be integrated into the packaging for the device 300 or appliance, for example. When the monitoring device is separated from the magnet (e.g., by removing the magnet or removing the device and appliance from the packaging), the switch closes and connects the power source 316. As another example, the monitoring device 300 can include a mechanical switch such as a push button that is manually actuated in order to connect the power source 316. In some embodiments, the activation mechanism includes a latching function that locks the switch upon the first actuation to maintain connectivity with the power source so as to maintain activation of the monitoring device 300. Optionally, the switch for the activation mechanism can be activated by a component in the patient's intraoral cavity (e.g., a magnet coupled to a patient's tooth), such that the monitoring device 300 is active only when the appliance is worn by the patient, and is inactive when the appliance is removed from the patient's mouth. Alternatively or in combination, the switch can be activated by other types of signals, such as an optical signal.

Figure 23:
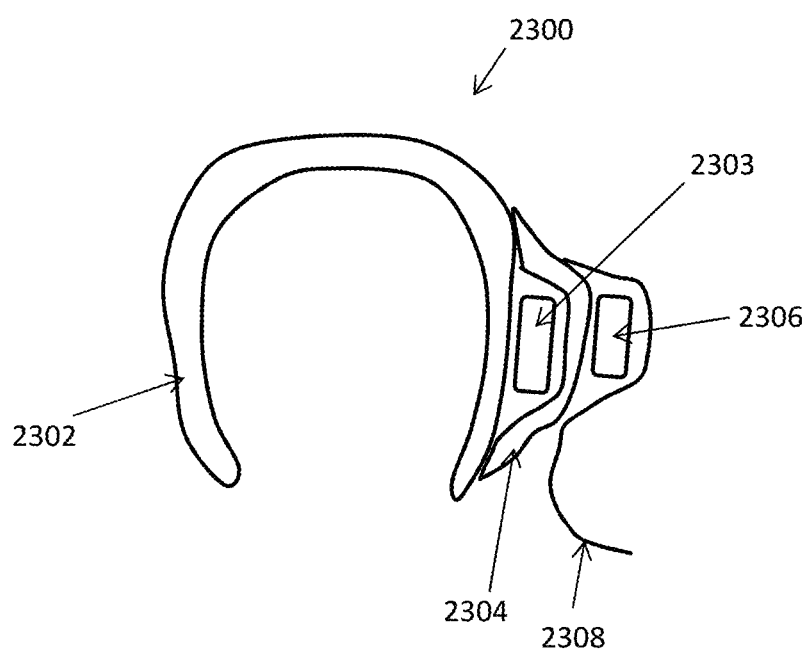
FIG. 23 illustrates an example of a monitoring device.

FIG. 23 illustrates a monitoring device 2300 with an activation mechanism, in accordance with embodiments. The monitoring device 2300, as with all other monitoring devices described herein, can be similar to the monitoring device 300, and can include some or all of the components described herein with respect to the monitoring device 300. The device 2300 is coupled to an intraoral appliance 2302 (e.g., via an encapsulating material 2304). The device 2300 can include an activation mechanism 2303 including a magnetic switch. Prior to use, the device 2300 can be removably coupled to a magnet 2306 (e.g., using tape 2308), and the magnet 2306 can hold the magnetic switch in an open position such that the device 2300 is inactive. When the appliance 2302 is ready for use, the user can remove the magnet 2306, thus closing the magnetic switch and connecting the components of the monitoring device 2300 to a power source. The intraoral appliances and monitoring devices described herein can be configured in many different ways. In some embodiments, an intraoral appliance as described herein is operably coupled to a single monitoring device. Alternatively, the intraoral appliance can be operably coupled to a plurality of monitoring devices, such as at least two, three, four, five, or more monitoring devices. Some or all of the monitoring devices may be of the same type (e.g., collect the same type of data). Alternatively, some or all of the monitoring devices may be of different types (e.g., collect different types of data). Any of the embodiments of monitoring devices described herein can be used in combination with other embodiments in a single intraoral appliance.

A monitoring device can be located at any portion of the appliance, such as at or near a distal portion, a mesial portion, a buccal portion, a lingual portion, a gingival portion, an occlusal portion, or a combination thereof. The monitoring device can be positioned near a tissue of interest when the appliance is worn in the patient's mouth, such as near or adjacent the teeth, gingiva, palate, lips, tongue, cheeks, airway, or a combination thereof. For example, when the appliance is worn, the monitoring device can cover a single tooth, or a portion of a single tooth. Alternatively, the monitoring device can cover multiple teeth or portions thereof. In embodiments where multiple monitoring devices are used, some or all of the monitoring devices can be located at different portions of the appliance. Alternatively, some or all of the monitoring devices can be located at the same portion of the appliance.

A monitoring device can be operably coupled to the intraoral appliance in a variety of ways. For example, the monitoring device can be physically integrated with the intraoral appliance by coupling the monitoring device to a portion of the appliance (e.g., using adhesives, fasteners, latching, laminating, molding, etc.). The coupling may be a releasable coupling allowing for removal of the monitoring device from the appliance, or may be a permanent coupling in which the monitoring device is permanently affixed to the appliance. Alternatively or in combination, the monitoring device can be physically integrated with the intraoral appliance by encapsulating, embedding, printing, or otherwise forming the monitoring device with the appliance. In some embodiments, the appliance includes a shell shaped to receive the patient's teeth, and the monitoring device is physically integrated with the shell. The monitoring device can be located on an inner surface of the shell (e.g., the surface adjacent to the received teeth), an outer surface of the shell (e.g., the surface away from the received teeth), or within a wall of the shell. Optionally, as discussed further herein, the shell can include a receptacle shaped to receive the monitoring device. Exemplary methods for fabricating an appliance with a physically integrated monitoring device (e.g., by incorporating some or all of the components of the monitoring device during direct fabrication of the appliance) are described in further detail herein.

Figure 3B:
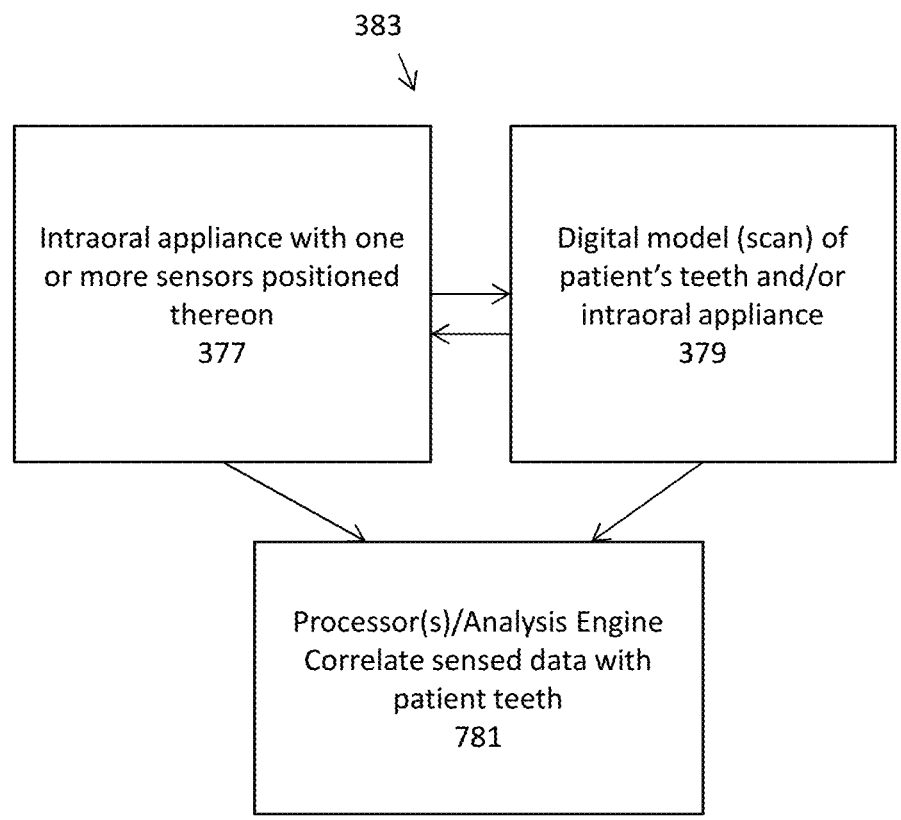
FIG. 3B schematically illustrates a system including any of the intraoral appliances with one or more sensors as described herein, and digital scan data of the appliance and/or patient's teeth. An analysis engine (which may be part of the intraoral appliance or separate from the intraoral appliance) may integrate the distal information and the sensor information, and may relate the specific sensor information to the patient's teeth using the digital scan data.

In general any of the apparatuses described herein may be used in conjunction with digital model(s) or scans or the patient's teeth and/or intraoral appliance. For example, FIG. 3B schematically illustrates a system 383 including an intraoral appliance 377 with one or more sensors, and digital scan data of the appliance and/or patient's teeth 379. An analysis engine 381 (which may be part of the intraoral appliance or separate from the intraoral appliance) may integrate the distal information and the sensor information, and may relate the specific sensor information to the patient's teeth using the digital scan data.

Figure 4A:
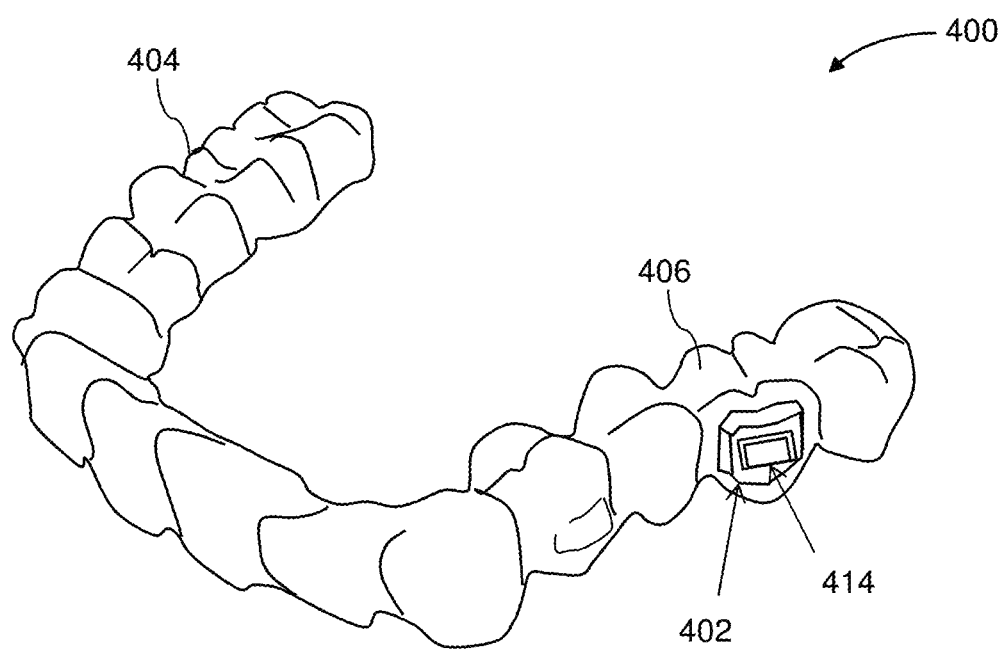
FIG. 4A illustrates an example of an intraoral appliance including an integrated monitoring device.
Figure 4B:
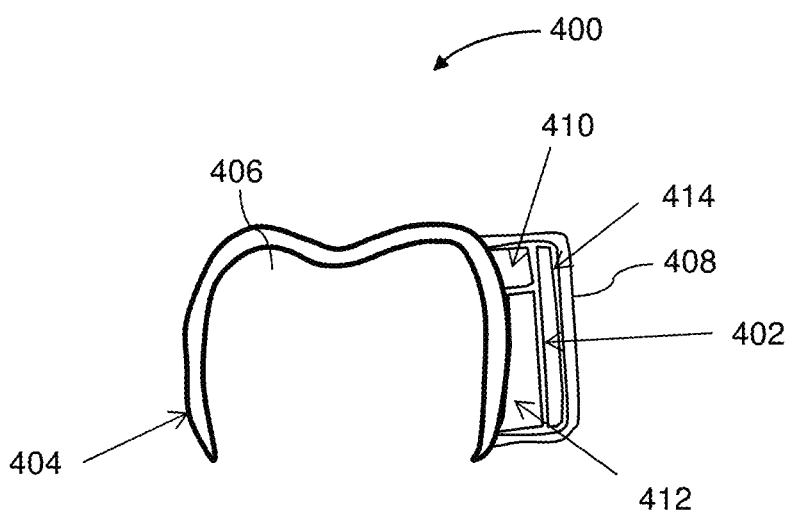
FIG. 4B is a cross-sectional view of the appliance of FIG. 4A.

FIGS. 4A and 4B illustrate an intraoral appliance 400 including an integrated monitoring device 402, in accordance with embodiments. The appliance 400 includes a shell 404 having a plurality of teeth receiving cavities, and the monitoring device 402 is coupled to an outer, buccal surface of the shell 404 adjacent a tooth receiving cavity 406. In the depicted embodiment, the monitoring device 402 is coupled to a tooth receiving cavity 406 for a molar. It shall be appreciated that in alternative embodiments, the monitoring device 402 can be coupled to other portions of the shell 404, such as an inner surface, a lingual surface, an occlusal surface, one or more tooth receiving cavities for other types of teeth (e.g., incisor, canine, premolar), etc. The monitoring device 402 can be shaped to conform to the geometry of the corresponding appliance portion (e.g., the wall of the cavity 306) so as to provide a lower surface profile and reduce patient discomfort. In some embodiments, the appliance 400 includes a receptacle 408 formed on the outer surface of the shell 404 and the monitoring device 402 is positioned within the receptacle. Exemplary methods for forming an appliance with a receptacle 408 and integrated monitoring device 402 are described in detail below.

The monitoring device 402 can include any of the components previously described herein with respect to the monitoring device 300 of FIG. 3A. For example, the monitoring device 402 can include a sensor 410, a power source 412 (e.g., a battery), and/or a communication unit 414 (e.g., a wireless antenna). The arrangement of the components of the monitoring device 402 can be varied as desired. In some embodiments, the sensor 408 is located adjacent to the tooth receiving cavity 406. A gap can be formed in the shell 404 adjacent to the sensor 410 so as to permit direct access to the received tooth. The communication unit 414 (or a component thereof, such as an antenna) can be located adjacent to or on the outer surface of the receptacle 408 so as to facilitate data transmission.

Figure 5:
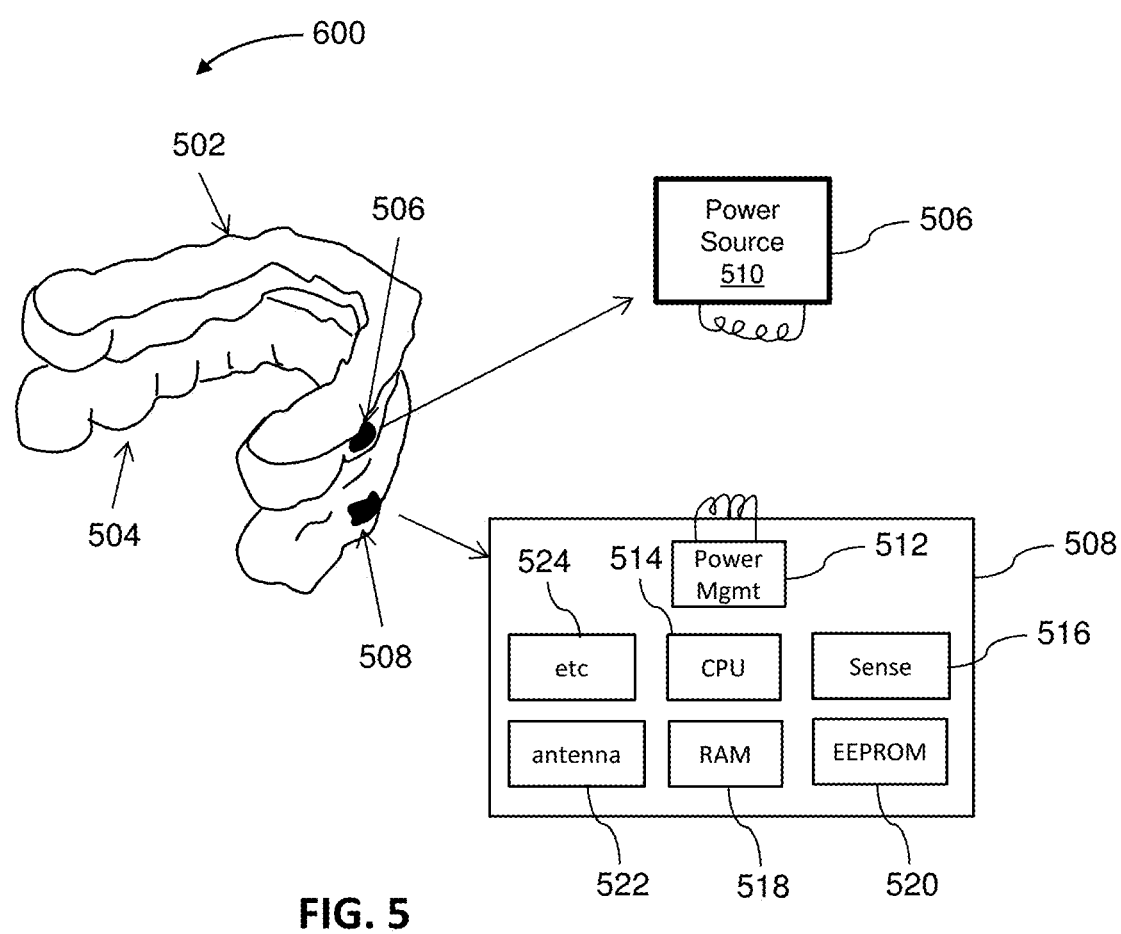
FIG. 5 illustrates an example of a monitoring system including a first appliance and a second appliance.

In some embodiments, some of the components of a monitoring device may be packaged and provided separately from other components of the device. For example, a monitoring device can include one or more components that are physically integrated with a first intraoral appliance and one or more components that are physically integrated with a second intraoral appliance. The first and second intraoral appliances can be worn on opposing jaws, for example. Any of the components of a monitoring device (e.g., components of the device 300 of FIG. 3A) can be located on an appliance for the upper jaw, an appliance for the lower jaw, or a combination thereof. In some embodiments, it is beneficial to distribute the components of the monitoring device across multiple appliances in order to accommodate space limitations, accommodate power limitations, and/or improve sensing, for example. Additionally, some of the components of a monitoring device can serve as a substrate for other components (e.g., a battery serves as a substrate to an antenna). FIG. 5 illustrates a monitoring system 500 including a first appliance 502 and a second appliance 504, in accordance with embodiments. The first appliance 502 can be shaped to receive teeth of a patient's upper arch and the second appliance 504 can be shaped to receive teeth of a patient's lower arch. The system 500 can include a monitoring device separated into a first subunit 506 physically integrated with the first appliance 502 and a second subunit 508 physically integrated with the second appliance 508. In some embodiments, the first subunit 506 is a power supply subunit including a power source 510, and the second subunit 508 is a sensing subunit including the remaining components of the monitoring device, such as a power management unit 512, processor (e.g., CPU 514), sensor 516, memory (e.g., RAM 518 such as SRAM or DRAM; ROM such as EPROM, PROM, or MROM; or hybrid memory such as EEPROM 520, flash, or NVRAM), communication unit (e.g., antenna 522), or any other component 524 described herein (e.g., with respect to the monitoring device 300 of FIG. 3A). The first subunit 506 and second subunit 508 can be operably coupled to each other via inductive coupling between the power supply 510 and power management unit 512, e.g., when the first appliance 502 and second appliance 504 are brought into proximity with each other by the closing of the patient's jaws.

The configuration of FIG. 5 can be varied as desired. For example, the first subunit 506 can be physically integrated with the second appliance 504 and the second subunit 508 can be physically integrated with the first appliance 502. As another example, the distribution of the monitoring device components between the first subunit 506 and second subunit 508 can differ from the depicted embodiment.

Alternatively or in combination, a monitoring device can include one or more components that are physically integrated with an intraoral appliance and one or more components that are physically integrated with another device external to the patient's intraoral cavity. For example, the external device can be a wearable device (e.g., headgear, smart watch, wearable computer, etc.) worn on another portion of the patient's body. As another example, the external device can be a power hub, a mobile device, personal computer, laptop, tablet, etc. Any of the components of a monitoring device (e.g., components of the device 300 of FIG. 3A) can be located on an external device. In some embodiments, the monitoring device includes a communication unit and antenna integrated into the intraoral appliance that transmits sensor data from the patient's intraoral cavity to the external device, and optionally receives data from the external device. The monitoring device components integrated into the external device can provide additional functionality (e.g., processing and/or analysis capabilities) that augments the functionality of the monitoring device components within the intraoral appliance. The monitoring device components within the intraoral appliance may be capable of operating with or without the augmented functionalities.

Alternatively or in combination, a monitoring device can include one or more components that are physically integrated with an intraoral appliance and one or more components that are located in the patient's intraoral cavity separate from the appliance. The intraoral components can be positioned so as to interact with (e.g., physically contact, communicate with) the integrated components in the appliance when the appliance is worn. In some embodiments, the intraoral components are coupled to a portion of the intraoral cavity, such as a crown of the patient's tooth. For instance, the intraoral components can be physically integrated into an attachment device mounted on a patient's tooth. Alternatively or in combination, the monitoring device can be surgically implanted, e.g., in the bone of the patient's jaw. Any of the components of a monitoring device (e.g., components of the device 300 of FIG. 3A) can be located in the patient's intraoral cavity rather than in the intraoral appliance. In some embodiments, the appliance and integrated components can be removed from the patient's mouth independently of the intraoral components. Advantageously, this approach may reduce costs by allowing the same device components to be used with multiple different appliances, e.g., when applying a sequence of shell appliances to reposition the patient's teeth.

Figure 6A:
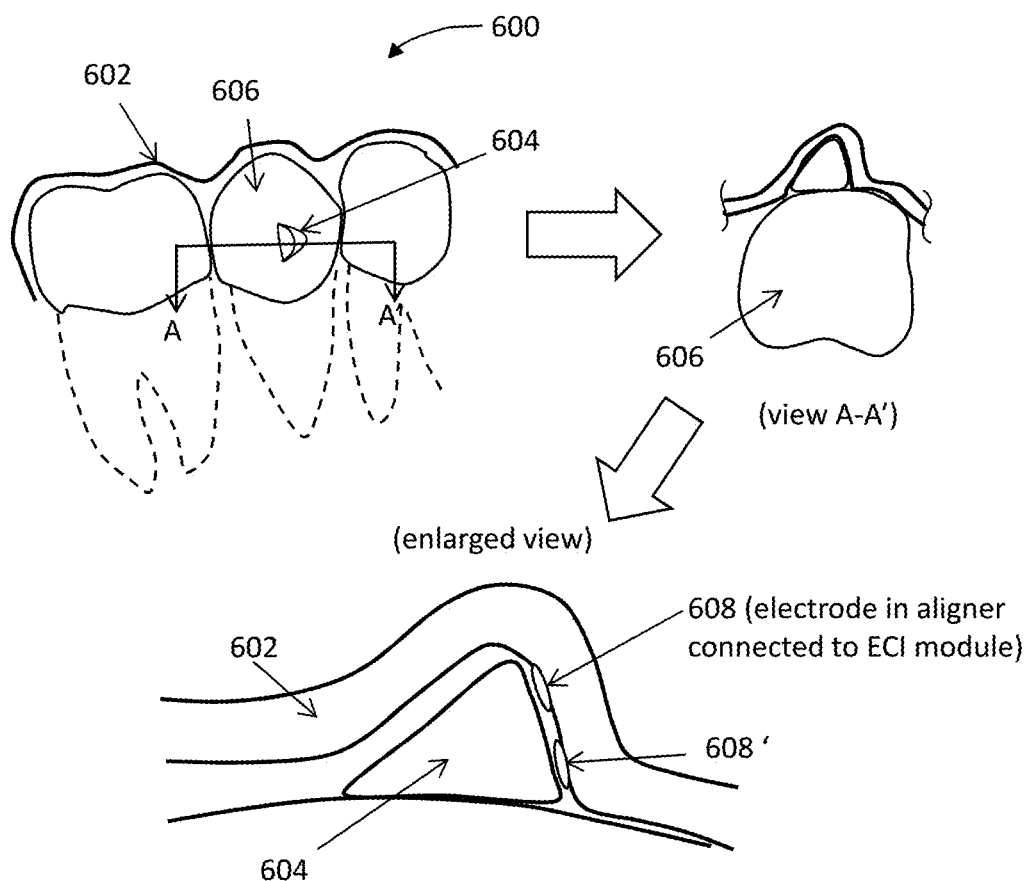
FIG. 6A illustrates an example of a system including an intraoral appliance and an attachment device mounted on a tooth.

FIG. 6A illustrates a system 600 including an intraoral appliance 602 and an attachment device 604 mounted on a tooth 606, in accordance with embodiments. The appliance 602 can include a shell with a tooth receiving cavity shaped to receive the tooth 606 and a receptacle shaped to accommodate the attachment device 604 on the tooth 606. In some embodiments, the system 600 includes a monitoring device having a first subunit physically integrated into the appliance 602 (e.g., according to any of the methods described herein) and a second subunit physically integrated into the attachment device 604. In some embodiments, the second subunit integrated into the attachment device 604 includes the relatively bulky components of the monitoring device, such as the power source, memory, and/or sensors. For example, the attachment device 604 can include a battery or other power source operably coupled to the monitoring device components integrated into the appliance 602, e.g., via inductive coupling or direct contact using electrodes 608. In alternative embodiments, this configuration can be reversed, with the power source mounted in the appliance 602 and the remaining monitoring device components located in the attachment device 604. This approach can reduce costs when multiple appliances are used, since only the power source is replaced with each new appliance. As another example, the attachment device 604 can include a passive sensing element driven by one or more monitoring device components located in the appliance 602. In yet another example, the attachment device 604 can include a conductive element used to trigger a switch integrated in the appliance 602.

Figure 6B:
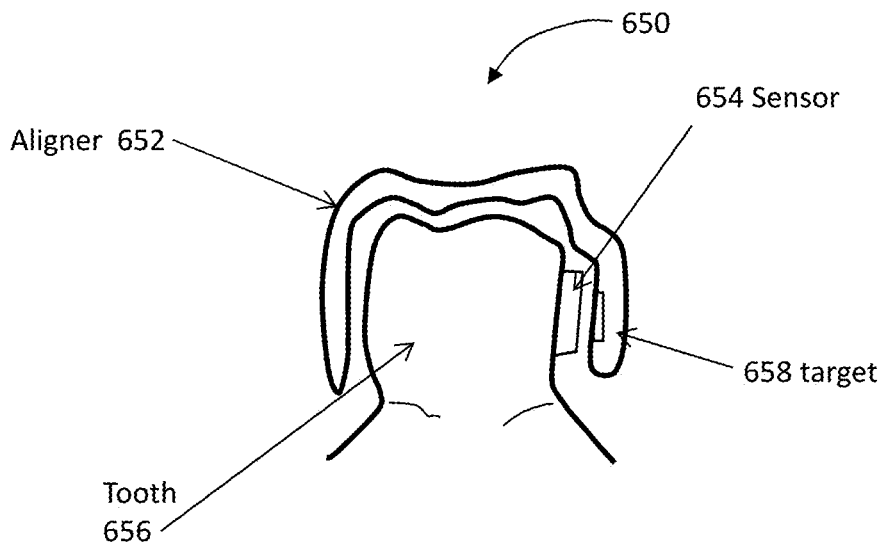
FIG. 6B shows an example of a system including an intraoral appliance and an attachment device mounted on a tooth.

FIG. 6B illustrates a system 650 including an intraoral appliance 652 and an attachment device 654 mounted on a tooth 656, in accordance with embodiments. Similar to the appliance 600, the appliance 652 can include a shell with a tooth receiving cavity shaped to receive the tooth 656 and a receptacle shaped to accommodate the attachment device 654 on the tooth 656. In some embodiments, the system 650 includes a monitoring device having a first subunit physically integrated into the appliance 652 (e.g., according to any of the methods described herein) and a second subunit physically integrated into the attachment device 654. The first subunit in the appliance 652 can include a sensing target 658 and the second subunit in the attachment device 654 can include one or more sensors configured to detect the target. For example, the sensing target 658 can be a mirror or opaque surface and the sensor can be a photodetector. As another example, the sensing target 658 can be a magnet and the sensor can be a magnetometer. In yet another example, the sensing target 658 can be a metallic element (e.g., foil, coating) and the sensor can be a capacitive sensor. Optionally, the sensing target 658 can be a powered coil generating an AC electromagnetic field, such that the sensor also obtains power from the sensing target 658. In alternative embodiments, the locations of the first and second subunits can be reversed, such that the sensing target 658 is located in the attachment device 654 and the sensor is located in the appliance 652.

The monitoring devices of the present disclosure may utilize many different types and configurations of sensors. The description below of certain exemplary monitoring devices is not intended to be limiting, and it shall be appreciated that the features of the various embodiments described herein can be used in combination with features of other embodiments. For example, the monitoring devices discussed below may also include any of the components previously described with respect to the monitoring device 300 of FIG. 3A. A single monitoring device can include any combination of the sensor types and sensor configurations described herein.

In some embodiments, a monitoring device includes a structure shaped to interact with the sensor when the intraoral appliance is worn on the patient's teeth. The monitoring device can include one or more deflectable structures (e.g., a cantilever, dimple, concavity, flap, protrusion, pop-out structure, etc.) formed with or coupled to the appliance. The deflectable structure can be deflected outward by the patient's tooth or an attachment device coupled to the tooth when the appliance is worn, for example. In some embodiments, the monitoring device includes a sensor (e.g., a mechanical switch such as a push button), an electrical switch, an optical switch, a proximity sensor, a touch sensor, etc., configured to generate sensor data indicative of deflection of the deflectable structure (e.g., whether the structure is deflected, the deflection distance, etc.). The monitoring device can also include a processor operably coupled to the sensor and configured to process the sensor data so as to generate appliance usage and/or compliance data (e.g., information regarding whether the appliance is being worn). Optionally, the sensor can provide more complex data (e.g., force and/or pressure data) regarding the interaction between the appliance and the patient's teeth. In some embodiments, the deflectable structure is in a deflected state when the appliance is being worn and in a resting state when the appliance is not being worn, and the deflectable structure interacts with (e.g., activates) the sensor only when in the deflected state.

FIGS. 7A and 7B illustrate a monitoring device 700 with a deflectable structure 702, in accordance with embodiments. In the depicted embodiment, the deflectable structure 702 is formed in a shell 704 of an intraoral appliance, e.g., in a wall of a tooth receiving cavity 706. The monitoring device 700 can include a sensor 708 (e.g., push button) configured to detect the deflection of the deflectable structure 702. When the appliance is not being worn on the patient's teeth (FIG. 7A), the deflectable structure 702 can be in a resting state such that the sensor 708 is not activated. When the appliance is worn by the patient, the tooth 710 (e.g., a first or second molar) can displace the deflectable structure 702 outwards to activate the sensor 708. The deflection distance can be varied as desired. For instance, the structure 702 can be deflected outward by a distance of at least about 25 μm, at least about 30 μm, at least about 50 μm, at least about 100 μm, at least about 200 μm, at least about 300 μm, or a distance within a range from about 25 μm to about 300 μm. The monitoring device 700 can include other components (e.g., as previously described with respect to FIG. 3A) for storing, processing, analyzing, and/or transmitting the sensor data.

FIG. 7C illustrates a monitoring device 720 with a deflectable structure 722, in accordance with embodiments. The deflectable structure 722 is formed in a shell of an intraoral appliance, e.g., in a wall of a tooth receiving cavity 724. The tooth receiving cavity 724 is shaped to receive a tooth 726 coupled to an attachment device 728. In some embodiments, the attachment device 728 includes an activator structure 730 that deflects the deflectable structure 722 when the tooth 726 is received in the cavity 724. The monitoring device 720 includes a sensing subunit 732 mounted to the shell near the deflectable structure 722. The sensing subunit 732 includes a sensor 734 (e.g., a switch) that is activated by the deflection of the deflectable structure 722. Optionally, the sensor 732 can be covered with a flexible membrane. The subunit 732 can also include a power source, a processor, and/or any of the other monitoring device components described herein (e.g., with respect to the embodiment of FIG. 3A).

Figure 7D:
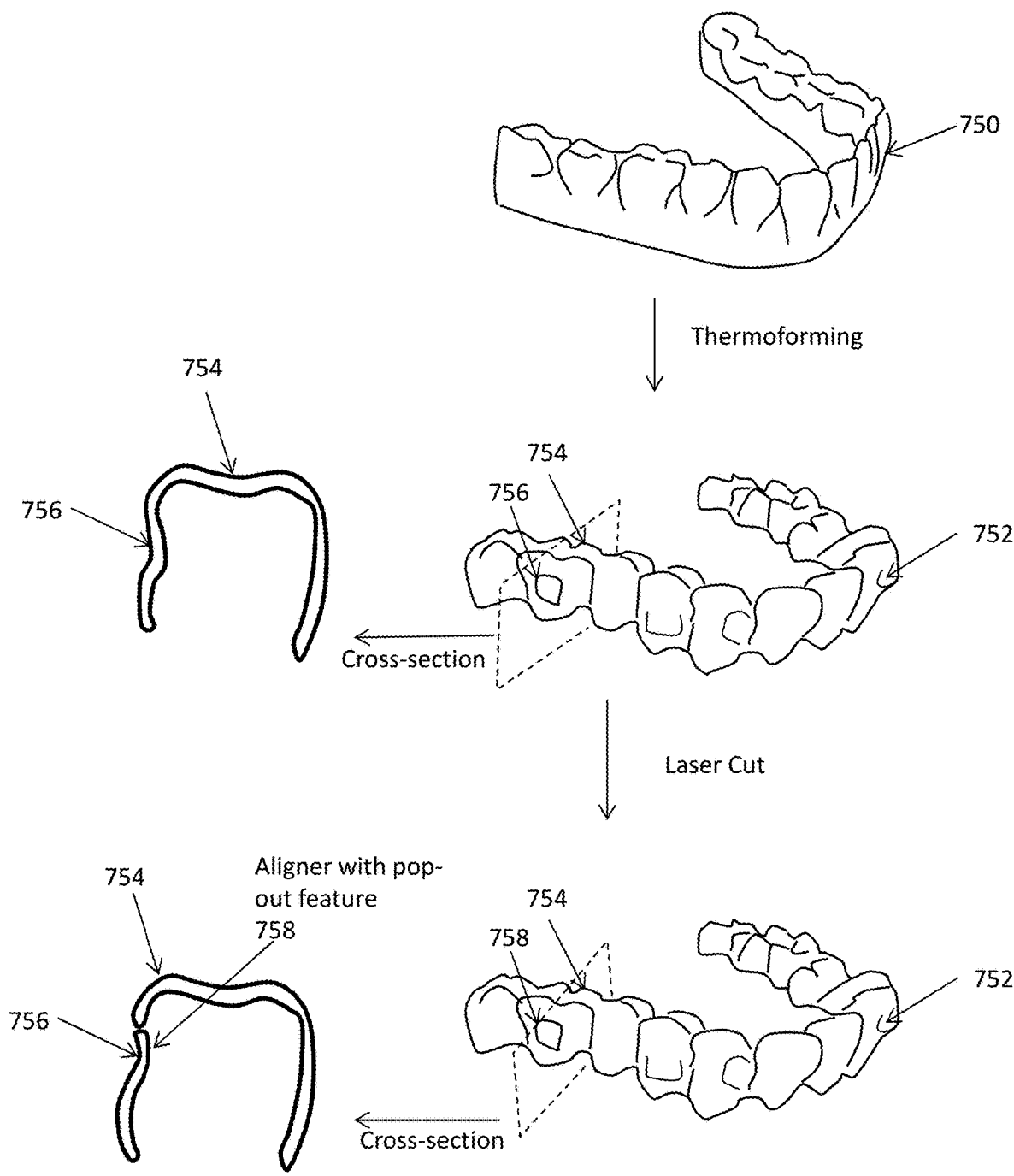
FIG. 7D illustrates an exemplary method for fabricating an intraoral appliance with a deflectable structure.

FIG. 7D illustrates a method for fabricating an intraoral appliance with a deflectable structure, in accordance with embodiments. In the first step, a mold 750 of a patient's dentition is provided. The mold 750 can represent the patient's teeth in a current or target tooth arrangement, for example. In a second step, an intraoral appliance 752 is formed by forming (e.g., thermoforming) a material over the mold 750. Alternatively, the intraoral appliance 752 can be formed by direct fabrication (e.g., stereolithography, 3D printing, etc.) without using the mold 750. The appliance can include a shell with a tooth receiving cavity 754 having a dimple or concavity 756 at the target location for the deflectable structure. In a third step, a deflectable structure 758 is formed in the appliance 752 by cutting the wall of the cavity 754 so as to form a cantilevered portion. Cutting of the appliance 752 can be performed using methods known to those of skill in the art, such as laser cutting or milling. Subsequently, the other components of the monitoring device can be coupled to the appliance 752 adjacent to or near the deflectable structure 758.

Alternatively or in combination, a monitoring device can include one or more proximity sensors configured to generate sensor data when in proximity to a sensing target. Examples of proximity sensors suitable for use with the embodiments herein include capacitive sensors, resistive sensors, inductive sensors, eddy-current sensors, magnetic sensors, optical sensors, photoelectric sensors, ultrasonic sensors, Hall Effect sensors, infrared touch sensors, or surface acoustic wave (SAW) touch sensors. A proximity sensor can be activated when within a certain distance of the sensing target. The distance can be about less than 1 mm, or within a range from about 1 mm to about 50 mm. In some embodiments, a proximity sensor can be activated without direct contact between the sensor and the sensing target (e.g., the maximum sensing distance is greater than zero).

In some embodiments, a proximity sensor is activated when in direct contact with the sensing target (the sensing distance is zero), also known as a touch or tactile sensor. Examples of touch sensors include capacitive touch sensors, resistive touch sensors, inductive sensors, pressure sensors, and force sensors. In some embodiments, a touch sensor is activated only by direct contact between the sensor and the sensing target (e.g., the maximum sensing distance is zero). Some of the proximity sensor types described herein (e.g., capacitive sensors) may also be touch sensors, such that they are activated both by proximity to the sensing target as well as direct contact with the target.

One or more proximity sensors may be integrated in the intraoral appliance and used to detect whether the appliance is in proximity to one or more sensing targets. The sensing targets can be an intraoral tissue (e.g., the teeth, gingiva, palate, lips, tongue, cheeks, or a combination thereof). For example, proximity sensors can be positioned on the buccal and/or lingual surfaces of an appliance in order to detect appliance usage based on proximity to and/or direct contact with the patient's cheeks and/or tongue. As another example, one or more proximity sensors can be positioned in the appliance so as to detect appliance usage based on proximity to and/or direct contact with the enamel and/or gingiva. In some embodiments, multiple proximity sensors are positioned at different locations appliance so as to detect proximity to and/or direct contact with different portions of the intraoral cavity.

Alternatively or in combination, one or more sensing targets can be coupled to an intraoral tissue (e.g., integrated in an attachment device on a tooth), or can be some other component located in the intraoral cavity (e.g., a metallic filling). Alternatively or in combination, one or more proximity sensors can be located in the intraoral cavity (e.g., integrated in an attachment device on a tooth) and the corresponding sensing target(s) can be integrated in the intraoral appliance. Optionally, a proximity sensor integrated in a first appliance on a patient's upper or lower jaw can be used to detect a sensing target integrated in a second appliance on the opposing jaw or coupled to a portion of the opposing jaw (e.g., attached to a tooth), and thus detect proximity and/or direct contact between the patient's jaws.

The proximity sensor may be a capacitive sensor activated by charges on the sensing target. The capacitive sensor can be activated by charges associated with intraoral tissues or components such as the enamel, gingiva, oral mucosa, saliva, cheeks, lips, and/or tongue. For example, the capacitive sensor can be activated by charges (e.g., positive charges) associated with plaque and/or bacteria on the patient's teeth or other intraoral tissues. In such embodiments, the capacitive sensing data can be used to determine whether the appliance is being worn, and optionally the amount of plaque and/or bacteria on the teeth. As another example, the capacitive sensor can be activated by charges associated with the crowns of teeth, e.g., negative charges due to the presence of ionized carboxyl groups covalently bonded to sialic acid.

Various configurations of capacitive sensors can be used for the monitoring devices described herein. In some embodiments, the electrical charges on the surface of an intraoral tissue can interfere with the electric field of the capacitive sensor. Alternatively or in combination, the intraoral tissue can serve as the ground electrode of the capacitive sensor. Optionally, a shielding mechanism can be used to guide the electric field of the capacitive sensor in a certain location and/or direction for detecting contact with a particular tissue.

Figure 8A:
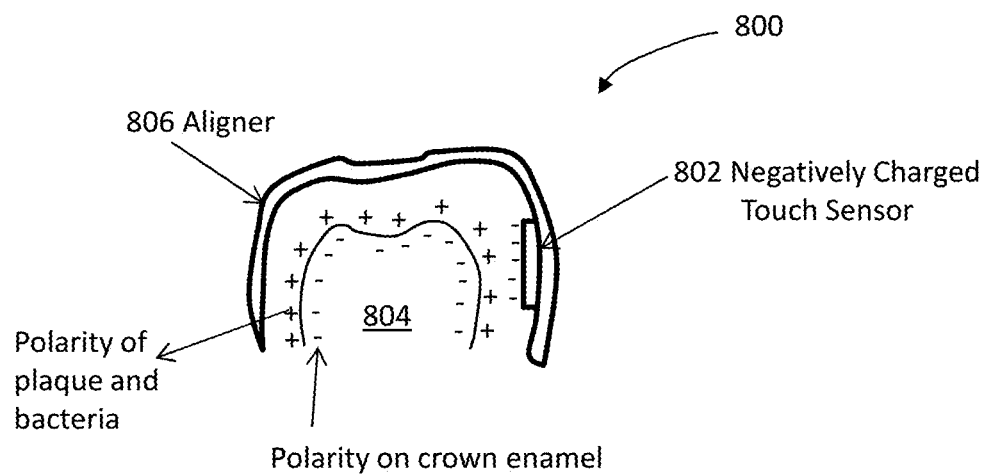
FIG. 8A illustrates an example of an intraoral appliance including a capacitive sensor.

FIG. 8A illustrates an intraoral appliance 800 including a capacitive sensor 802, in accordance with embodiments. In some embodiments, the sensing target for the capacitive sensor 802 is the surface of the patient's tooth 804, and the capacitive sensor 802 is coupled to the inner surface of a tooth receiving cavity 806 of an intraoral appliance so as to be adjacent to the tooth 804 when the appliance is worn. The capacitive sensor 802 can be activated by proximity to the tooth 804 and/or direct contact with the tooth 804. In some embodiments, the capacitive sensor 802 is activated by negative charges on the enamel of the tooth crown. Alternatively or in combination, the capacitive sensor 802 can be activated by positive charges associated with plaque and/or bacteria on the tooth crown. Optionally, the capacitive sensor 802 can be activated by charges associated with minerals in the patient's saliva on the tooth surface, including but not limited to $NH_4+$, $Ca_2+$, $PO_43"$, $HCO_3-$, and F.

Figure 8B:
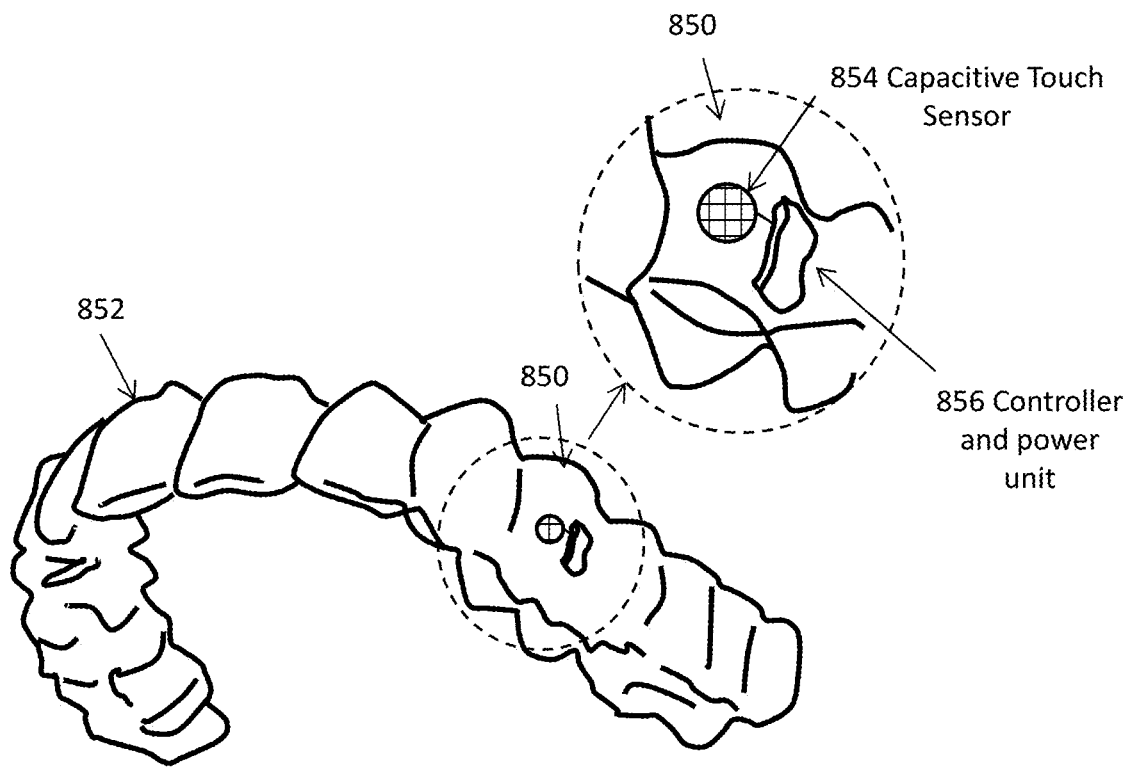
FIG. 8B illustrates an example of a monitoring device integrated into an intraoral appliance.

FIG. 8B illustrates a monitoring device 850 integrated into an intraoral appliance 852, in accordance with embodiments. The monitoring device 850 can be located on any suitable portion of the appliance 852, such as a buccal surface and/or lingual surface of the appliance 852 adjacent a tooth receiving cavity. The device 850 can include a capacitive sensor 854 (e.g., a capacitive touch sensor grid). The capacitive sensor 854 can be similar to the sensor 802 described with respect to FIG. 8A, for example. In some embodiments, the capacitive sensor 854 is flexible and/or thermoformable so as to conform to the shape of the appliance 852. The monitoring device 850 can also include a controller and power source 856 coupled to the capacitive sensor 854, as well as any of the other components described herein with respect to the monitoring device 300 of FIG. 3A. The controller and power source 856 can be used to power the capacitive sensor 854, process proximity and/or contact data obtained by the capacitive sensor 854, store the obtained data and/or processing results, and/or transmit the data and/or processing results to a remote device, for example.

Although FIG. 8B illustrates a single monitoring device 850 with a single capacitive sensor 854, other configurations can also be used. For example, in alternative embodiments, the monitoring device 850 can include multiple capacitive sensors located at different sites on the appliance 852 to detect proximity to and/or contact with multiple locations in the intraoral cavity. Optionally, multiple monitoring devices can be used, with each device being coupled to one or more respective capacitive sensors.

Figure 8C:
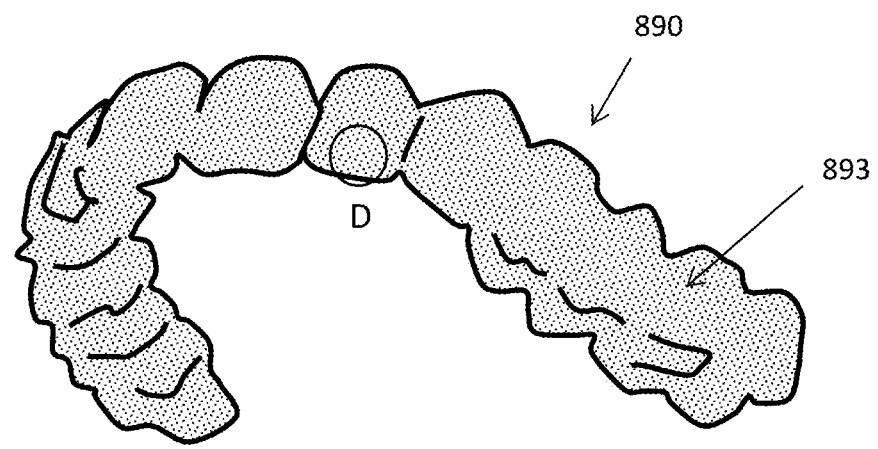
FIG. 8C illustrates an example of an intraoral appliance in which the majority of the aligner surface comprises a capacitive touch-sensor material.
Figure 8D:
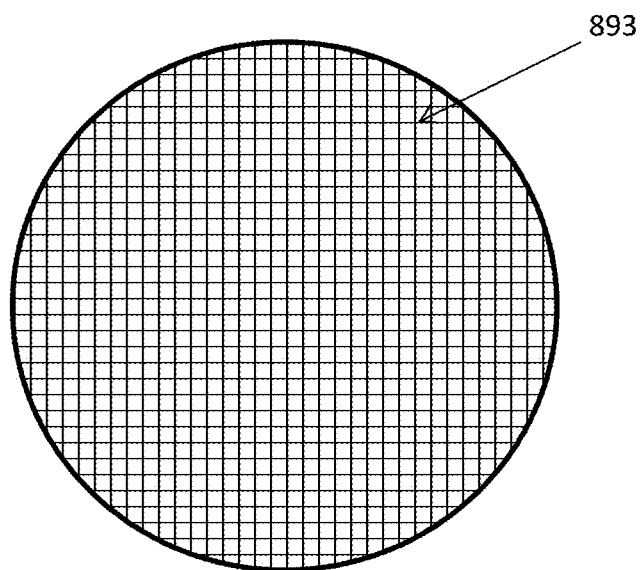
FIG. 8D illustrates an enlarged view, showing the grid pattern of the capacitive touch sensor that is distributed across the surface of the intraoral appliance of FIG. 8C.

In some variations, the majority of (or all of) the intraoral appliance (shown in this example as an aligner, but as mentioned above, may be configured as any other intraoral appliance) may include a capacitive touch-sensor material. In FIG. 8C, the aligner 890 includes a formed surface of capacitive touch-sensor material 893. FIG. 8D shows an enlarged view, showing a grid pattern of the capacitive touch sensor that may be distributed across the surface of the intraoral appliance of FIG. 8C.

The capacitive touch sensor may relate intensity and location of touch information, and may derive force (force moment, and force direction) on the patient's teeth from the intraoral appliance. In some variations the appliance may include one or more processors for receiving touch information from the grid of capacitive sensors and may correlate this information with applied force on the teeth by the apparatus. For example, the capacitive touch data may be correlate to particular teeth using a digital model of the patient's teeth and/or aligner (as discussed above generally in FIG. 3B).

Figure 9:
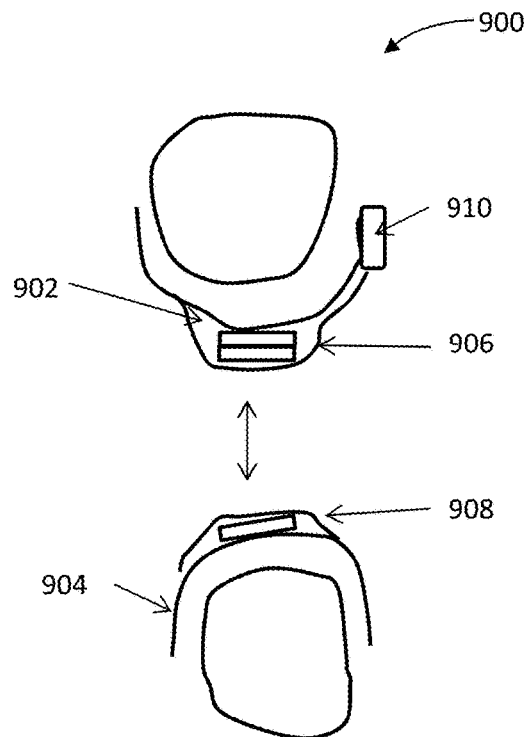
FIG. 9 illustrates an example of a monitoring system for detecting proximity between the patient's jaws.

FIG. 9 illustrates a monitoring system 900 for detecting proximity between the patient's jaws, in accordance with embodiments. The system 900 includes a first appliance 902 worn on the patient's upper teeth and a second appliance 904 worn on the patient's lower teeth. The system 900 also includes a monitoring device including a first sensing subunit 906 (e.g., a first plate) integrated with the first appliance 902, a second sensing subunit 908 (e.g., a second plate) integrated with the second appliance 904, and a controller 910 integrated with the first appliance 902 and coupled to the first sensing subunit 906. Alternatively, the controller 910 can be integrated with the second appliance 904 and coupled to the second sensing subunit 908. In some embodiments, the monitoring device is used to measure the capacitance and/or charge between first sensing subunit 906 and the second sensing subunit 908, and the measurement data can be used to determine whether the patient's jaws are in proximity to each other.

Alternatively or in combination, a monitoring device can include one or more vibration sensors configured to generate sensor data indicative of intraoral vibration patterns. Examples of vibration sensors include audio sensors (e.g., MEMS microphones), accelerometers, and piezoelectric sensors. The intraoral vibration patterns can be associated with one or more of: vibrations transferred to the patient's teeth via the patient's jaw bone, teeth grinding, speech, mastication, breathing, or snoring. In some embodiments, the intraoral vibration patterns originate from sounds received by the patient's ear drums. The intraoral vibration patterns may also originate from intraoral activities, such as teeth grinding, speech, mastication, breathing, snoring, etc. The sensor data generated by the vibration sensors can be processed to determine appliance usage and/or patient compliance. For instance, the monitoring device can include a processor that compares the detected intraoral vibration patterns to patient-specific intraoral vibration patterns to determine whether the appliance is being worn on a patient's teeth. In some embodiments, the processor is trained using previous data of patient-specific intraoral vibration patterns, and then determines whether the appliance is being worn by matching the measured patterns to the previous patterns. Alternatively or in combination, appliance usage can be determined by comparing the measured vibration patterns to vibration patterns obtained when the appliance is not being worn.

Alternatively or in combination, a monitoring device can include one or more optical sensors configured to detect appliance usage based on optical signals. For example, the optical sensors can be color sensors (e.g., mono-channel color sensors, multi-channel color sensors such as RGB sensors) configured to detect the colors of intraoral tissues. In some embodiments, one or more color sensors can be integrated into the intraoral appliance so as to be positioned adjacent to certain intraoral tissue (e.g., enamel, gingiva, cheeks, tongue, etc.) when the appliance is worn in the mouth. The device can determine whether the appliance is currently being worn based on whether the colors detected by the sensors match the expected colors for the tissues. In such embodiments, the monitoring device can include one or more light sources (e.g., LEDs) providing illumination for the color sensors.

As another example, the monitoring device can include one or more emitters (e.g., a LED) configured to generate optical signals and one or more optical sensors (e.g., a photodetector) configured to measure the optical signals. For example, an emitter can be positioned such that when the appliance is worn, the optical signal is reflected off of a surface (e.g., an intraoral tissue, a portion of an intraoral appliance) in order to reach the corresponding optical sensor. In some embodiments, when the appliance is not being worn, the optical signal is not reflected and does not reach the optical sensor. Accordingly, activation of the optical sensor can indicate that the appliance is currently being worn.

Figure 10A:
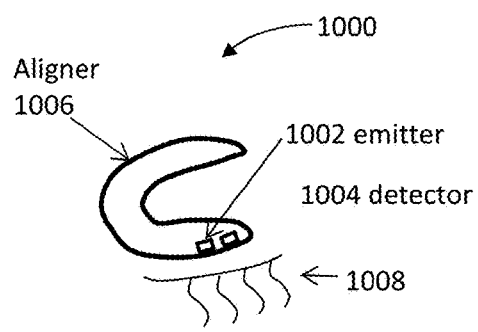
FIG. 10A shows an example of a monitoring device utilizing optical sensing.

FIG. 10A illustrates a monitoring device 1000 utilizing optical sensing, in accordance with embodiments. The device 1000 includes an emitter 1002 and an optical sensor 1004 integrated into an intraoral appliance 1006. In the depicted embodiment, the emitter 1002 and sensor 1004 are both located on a buccal surface of the appliance 1006 such that optical signals from the emitter 1002 are reflected off the patient's cheek 1008 to reach the sensor 1004 when the appliance 1006 is worn. In alternative embodiments, the emitter 1002 and sensor 1004 can be located on a lingual surface of the appliance 1006 such that optical signals from emitter 1002 are reflected off the patient's tongue to reach the sensor 1004.

Figure 10B:
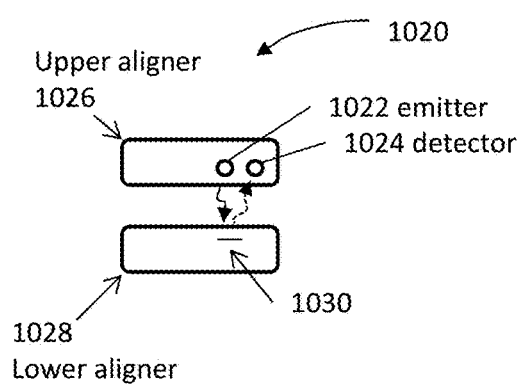
FIG. 10B illustrates an example of a monitoring device using optical sensing.

FIG. 10B illustrates a monitoring device 1020 using optical sensing, in accordance with embodiments. The device 1020 includes an emitter 1022 and an optical sensor 1024 integrated into a first intraoral appliance 1026 worn on a jaw of the patient (e.g., upper or lower jaw). The emitter 1022 and sensor 1024 can be arranged such that optical signals from the emitter 1022 reflect off of a second intraoral appliance 1028 worn on the patient's opposing jaw to reach the sensor 1024 when the first appliance 1026 and second appliance 1028 are being worn. Optionally, the second appliance 1028 can include a surface 1030 with optical properties selected to enhance and/or control reflection of the optical signal.

As another example, the emitter can be positioned such that when the appliance is worn, the optical signal is transmitted directly to the optical sensor without requiring any reflection off another surface. In some embodiments, when the appliance is not being worn, the optical signal does not reach the optical sensor. Accordingly, activation of the optical sensor can indicate that the appliance is currently being worn.

Figure 10C:
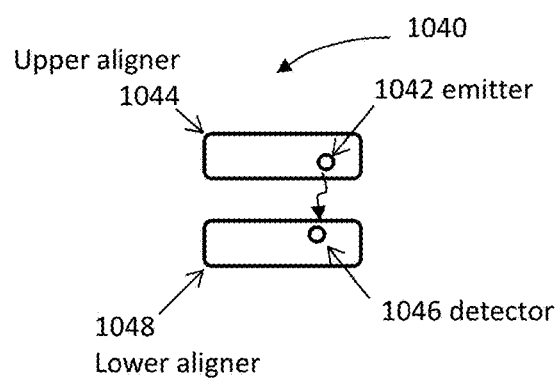
FIG. 10C illustrates an example of a monitoring device using optical sensing.

FIG. 10C illustrates a monitoring device 1040 using optical sensing, in accordance with embodiments. The device 1040 includes an emitter 1042 integrated into a first intraoral appliance 1044 worn on a jaw of the patient (e.g., upper or lower jaw) and an optical sensor 1046 integrated into a second intraoral appliance 1048 worn on the patient's opposing jaw. The emitter 1042 and sensor 1046 can be arranged such that the optical signals from the emitter 1042 are transmitted directly to the sensor 1046 when the first appliance 1044 and second appliances 1048 are worn. In yet another example, the emitter can be positioned such that when the appliance is worn, the optical signal is occluded by an intraoral tissue (e.g., the patient's tongue). In some embodiments, when the appliance is not being worn, the optical signal is not occluded and reaches the optical sensor (e.g., via direct transmission or reflection from a surface). Accordingly, activation of the optical sensor can indicate that the appliance is not currently being worn. Optionally, the optical signal can be infrared light in order to be less obtrusive to the patient.

Figures 11A, 11B:
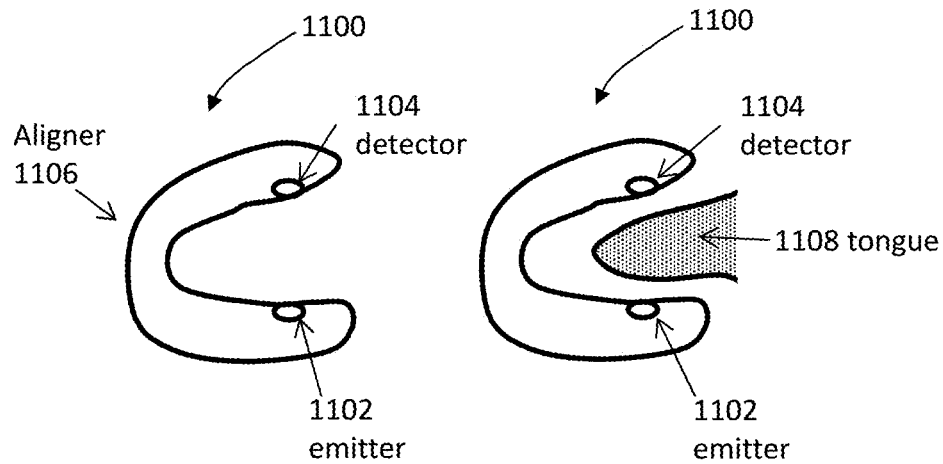
FIGS. 11A and 11B illustrate operation of an example of a monitoring device using optical sensing.

FIGS. 11A and 11B illustrate a monitoring device 1100 using optical sensing, in accordance with embodiments. The device 1100 includes an emitter 1102 and optical sensor 1104 integrated into an intraoral appliance 1106. The emitter 1102 and sensor 1104 can be positioned on opposing sides of the lingual surface of the appliance 1106 such that optical signals are transmitted directly from the emitter 1102 to the sensor 1104 when the appliance 1106 is not being worn (FIG. 11A). When the appliance 1106 is worn (FIG. 11B), the patient's tongue 1108 can occlude the transmission of optical signals between the emitter 1102 and sensor 1104.

Figures 11C, 11D:
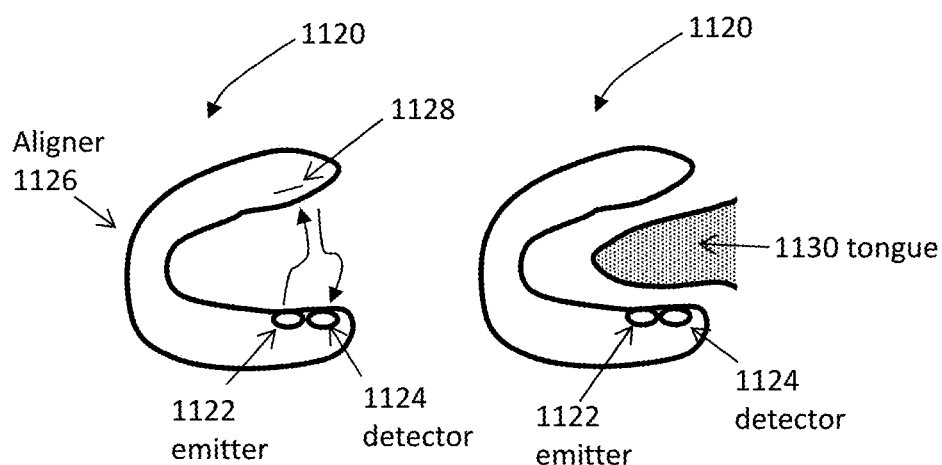
FIGS. 11C and 11D illustrate an example of a monitoring device using optical sensing.

FIGS. 11C and 11D illustrate a monitoring device 1120 using optical sensing, in accordance with embodiments. The device 1120 includes an emitter 1122 and optical sensor 1124 integrated into an intraoral appliance 1126. The emitter 1122 and sensor 1124 can be positioned the same side of the lingual surface of the appliance 1126 such that optical signals generated by the emitter 1122 are reflected off the opposing lingual surface 1128 to the sensor 1124 when the appliance 1126 is not being worn (FIG. 11C). Optionally, the optical properties of the surface 1128 can be selected to enhance and/or control the reflection of the optical signal. When the appliance 1126 is worn (FIG. 11D), the patient's tongue 1130 can occlude the transmission of optical signals between the emitter 1122 and sensor 1124.

Additionally, the optical sensing-based monitoring devices described herein can also be configured to detect variations in the reflected and/or transmitted optical signal caused by breathing, mastication, or other patient movements. This information can be used to further improve the reliability and accuracy of optical-sensing based compliance monitoring.

Alternatively or in combination, the monitoring devices of the present disclosure can include one or more magnetic sensors configured to detect appliance usage based on changes to a magnetic field. Examples of magnetic sensors suitable for use with the embodiments herein include magnetometers, Hall Effect sensors, magnetic reed switches, and magnetoresistive sensors. In some embodiments, the characteristics of the magnetic field (e.g., magnitude, direction) vary based on whether the appliance is currently being worn, e.g., due to interference from intraoral tissues such as the teeth. Accordingly, the device can determine appliance usage by processing and analyzing the magnetic field detected by the magnetic sensors.

Figures 12A, 12B:
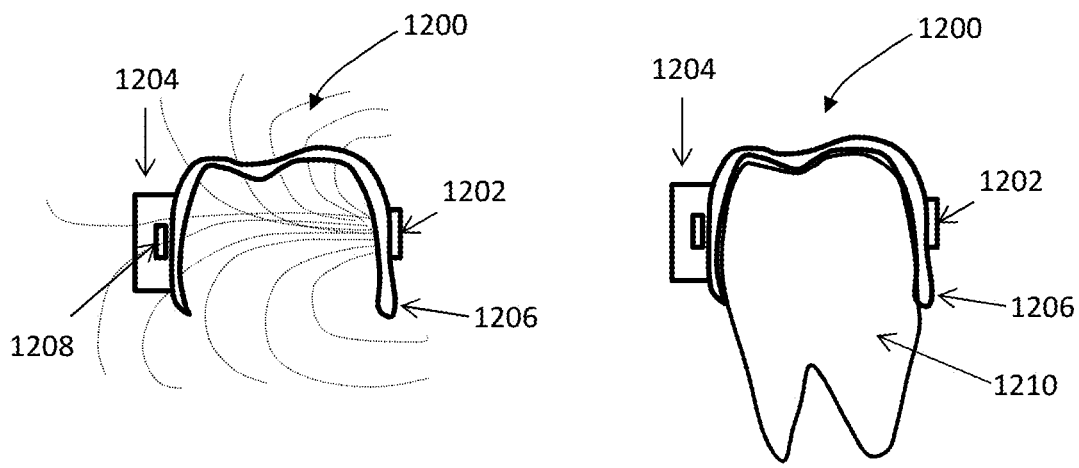
FIGS. 12A and 12B illustrate an example of a monitoring device using magnetic sensing.

FIGS. 12A and 12B illustrate a monitoring device 1200 using magnetic sensing, in accordance with embodiments. The device 1200 includes a magnet 1202 and a sensing subunit 1204 coupled to an intraoral appliance 1206. For example, the appliance 1206 can include a shell with tooth-receiving cavities and the magnet 1202 and sensing subunit 1204 can be coupled to the outer surface of a tooth receiving cavity. The sensing subunit 1204 includes one or more magnetic sensors 1208 (e.g., three magnetometers) configured to measure the characteristics (e.g., magnetic, direction) of the magnetic field generated by the magnet 1202. In some embodiments, when the appliance 1206 is worn by the patient, the tooth 1210 received in the cavity interferes with the magnetic field (FIG. 12B), such that the field characteristics differ from when the appliance is not being worn (FIG. 12A). The monitoring device 1200 can include a processor (not shown) configured to determine whether the appliance is being worn based on the sensing data produced by the magnetic sensor(s) 1208.

Figure 12C:
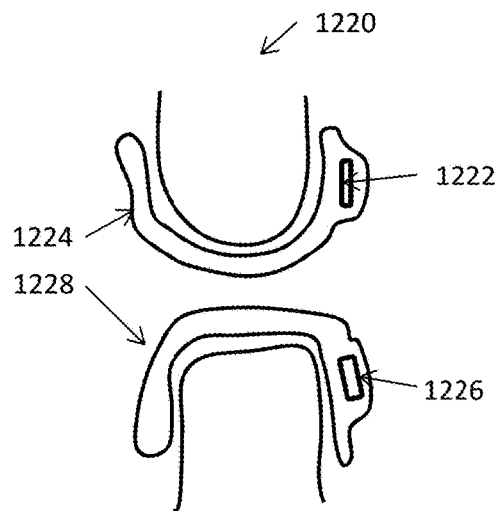
FIG. 12C shows an example of a monitoring device using magnetic sensing.

FIG. 12C illustrates a monitoring device 1220 using magnetic sensing, in accordance with embodiments. The device 1220 includes a magnetic sensor 1222 (e.g., a Hall Effect sensor or a magnetoresistive sensor) integrated into a first intraoral appliance 1224 worn on a patient's jaw (e.g., upper or lower jaw). The magnetic sensor 1222 is used to detect a magnetic field generated by a magnet 1226 integrated into a second intraoral appliance 1228 worn on the opposing jaw. In some embodiments, the characteristics of the magnetic field vary based on whether the first appliance 1224 and second appliance 1228 are being worn on the patient's teeth. The monitoring device 1220 can include a processor (not shown) configured to determine whether the appliances are being worn based on the sensing data produced by the magnetic sensors 1222.

A magnetic sensing-based monitoring device may include a ferromagnetic target (e.g., a metal plate) that alters the characteristics of the magnetic field when the appliance is worn. The ferromagnetic target can be integrated into an intraoral appliance or an attachment device mounted on a tooth, or can be an existing element in the intraoral cavity (e.g., a metal filling, implant, etc.). The monitoring device can detect whether the patient is using the appliance by sensing the characteristics of the magnetic field and detecting whether the ferromagnetic target is present.

Figure 13A:
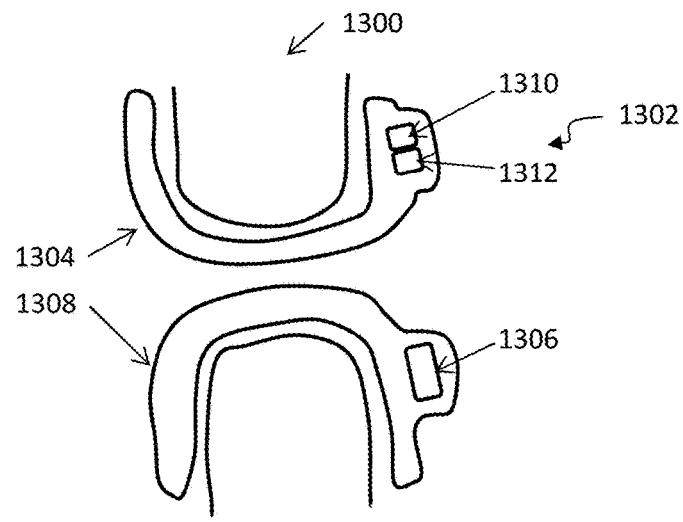
FIG. 13A illustrates an example of a monitoring device using magnetic sensing.

FIG. 13A illustrates a monitoring device 1300 using magnetic sensing, in accordance with embodiments. The monitoring device 1300 includes a sensing subunit 1302 integrated into a first intraoral appliance 1304 worn on a patient's jaw (e.g., upper or lower jaw) and a ferromagnetic target 1306 (e.g., a metal plate) integrated into a second intraoral appliance 1308 worn on the opposing jaw. The sensing subunit 1302 can include a magnet 1310 and a magnetic sensor 1312 that detect the magnetic field generated by the magnet 1310. In some embodiments, when the first appliance 1304 and second appliance 1308 are worn by the patient, the presence of the ferromagnetic target 1306 alters the characteristics of the generated magnetic field. The monitoring device 1300 can include a processor (not shown) configured to determine whether the appliances are being worn based on the sensing data produced by the magnetic sensor 1312.

Figure 13B:
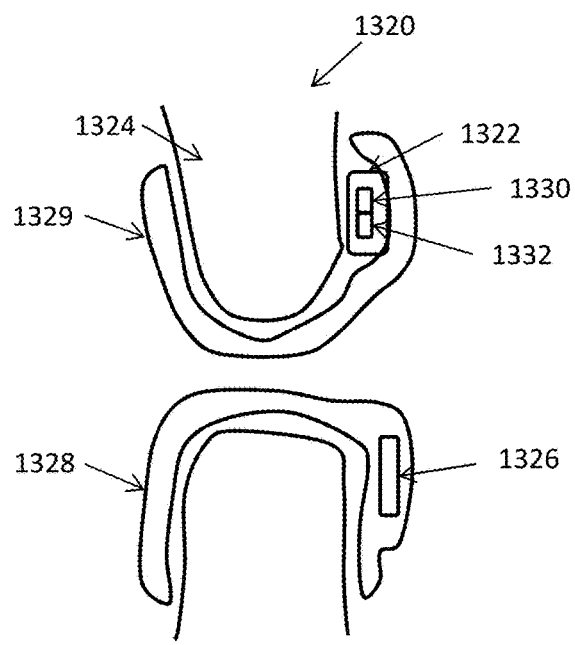
FIG. 13B illustrates an example of a monitoring device using magnetic sensing.
Figure 13C:
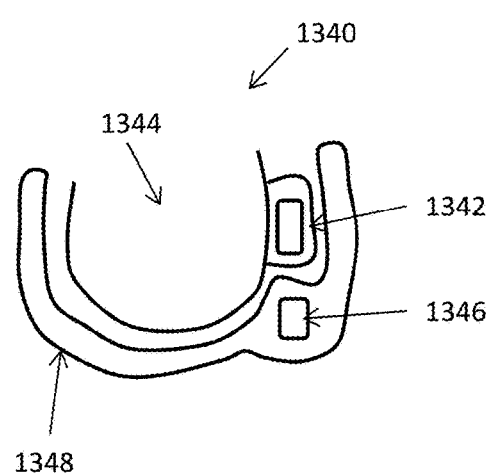
FIG. 13C shows an example of a monitoring device using magnetic sensing.

FIG. 13B illustrates a monitoring device 1320 using magnetic sensing, in accordance with embodiments. The monitoring device 1320 includes a sensing subunit 1322 integrated into an attachment device coupled to a tooth 1324 in a patient's jaw (e.g., upper or lower jaw) and a ferromagnetic target 1326 (e.g., a metal plate) integrated into an intraoral appliance 1328 worn on the opposing jaw. Optionally, a second intraoral appliance 1329 including a cavity shaped to receive the tooth 1324 and sensing subunit 1322 can also be worn. The sensing subunit 1322 can include a magnet 1330 and a magnetic sensor 1332 that detects the magnetic field generated by the magnet 1330. In some embodiments, when the appliance 1328 is worn by the patient, the presence of the ferromagnetic target 1326 alters the characteristics of the generated magnetic field. The monitoring device 1320 can include a processor (not shown) configured to determine whether the appliance 1328 is being worn based on the sensing data produced by the magnetic sensor 1332. Optionally, the processor and other components of the monitoring device 1320 can also be integrated into the attachment device. This implementation can reduce the costs of the device 1320, since only the relatively low cost ferromagnetic target would be replaced with each new appliance. FIG. 13C illustrates a monitoring device 1340 using magnetic sensing, in accordance with embodiments. The monitoring device 1340 includes a sensing subunit 1342 integrated into an attachment device coupled to a tooth 1344 in a patient's jaw (e.g., upper or lower jaw) and a ferromagnetic target 1346 (e.g., a metal plate) integrated into an intraoral appliance 1348 worn on the same jaw. The appliance 1348 can include a cavity shaped to receive the tooth 1344 and the sensing subunit 1342. The sensing subunit 1342 can include a magnet and a magnetic sensor that detects the magnetic field generated by the magnet. In some embodiments, when the appliance 1348 is worn by the patient, the presence of the ferromagnetic target 1346 alters the characteristics of the generated magnetic field. The monitoring device 1340 can include a processor (not shown) configured to determine whether the appliance 1348 is being worn based on the sensing data produced by the magnetic sensor. Optionally, the processor and other components of the monitoring device 1340 can also be integrated into the attachment device, thus reducing cost when multiple appliances are used.

Alternatively or in combination, a monitoring device can use a magnet to directly activate a magnetic sensor. For example, a magnet can be attached to an intraoral tissue, such as a tooth surface. The monitoring device can include a magnetic sensor (e.g., a magnetic reed sensor or switch) integrated into an intraoral appliance such that when the appliance is worn, the magnet activates the sensor. In alternative embodiments, the locations of the magnet and magnetic sensor can be switched, such that the magnetic sensor is attached to the intraoral tissue and the magnet is integrated into the appliance. Optionally, the magnet can be integrated into a first intraoral appliance worn on a patient's jaw (e.g., upper or lower jaw) and the magnetic sensor can be integrated into a second intraoral appliance worn on the opposing jaw, such that when both appliances are worn, the magnet activates the sensor.

Alternatively or in combination, a monitoring device can utilize two or more magnets that interact with each other (e.g., by exerting magnetic forces on each other), and a sensor that detects the interaction between the magnets. For example, the sensor can be a mechanical switch coupled to a magnet and actuated by magnetic forces exerted on the magnet. As another example, the sensor can be configured to detect the characteristics (e.g., magnitude, direction) of the magnetic force exerted on a magnet by the other magnets. The magnets and sensor can each be independently integrated in an appliance or coupled to a tooth or other intraoral tissue.

Figure 14A:
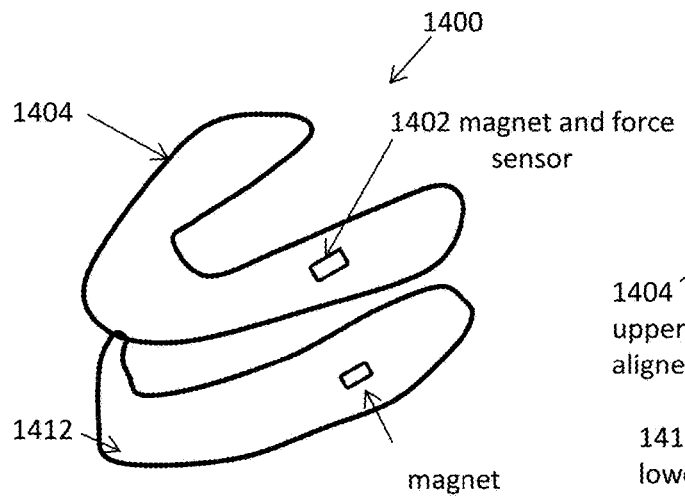
FIG. 14A illustrates an example of a monitoring device using a plurality of magnets.
Figure 14B:
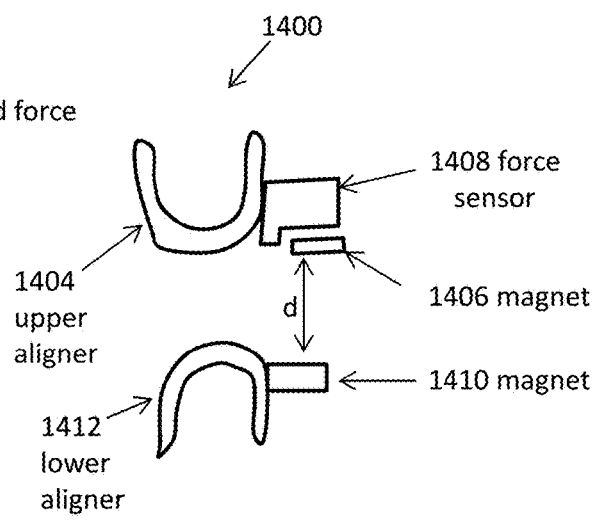
FIG. 14B is a cross-sectional view of the device of FIG. 14A.

FIGS. 14A and 14B illustrate a monitoring device 1400 using a plurality of magnets, in accordance with embodiments. The device 1400 includes a sensing subunit 1402 integrated into a first intraoral appliance 1404 worn on a patient's jaw (e.g., upper or lower jaw). The sensing subunit includes a first magnet 1406 coupled to a force sensor 1408. A second magnet 1410 is integrated into a second intraoral appliance 1412 worn on the opposing jaw. The force sensor 1408 can measure the magnetic force between the first magnet 1406 and the second magnet 1410, which varies according to the distance between the magnets. The monitoring device 1400 can include a processor (not shown) configured to determine whether the appliances are being worn based on the measured force. In some embodiments, the magnetic force can also be used to generate power for monitoring device 1400.

Alternatively or in combination, the monitoring devices of the present disclosure can include one or more force and/or pressure sensors for detecting appliance usage. For example, the monitoring device can include a force- and/or pressure-dependent resistive material, such as a film or sheet. The resistive material can be positioned between two thin electrodes in an intraoral appliance, and the resistance of the material may increase or decrease as force and/or pressure is exerted on the material, e.g., by the interaction between the teeth and the appliance. Other types of force and/or pressure sensors include strain gauges and piezocrystal sensors. In some embodiments, the monitoring device determines whether the patient is wearing the appliance based on the force and/or pressure measurements obtained by the force and/or pressure sensors. The measurement data may be indicative of the force and/or pressure between the appliance and an intraoral tissue, such as one or more of the patient's teeth. Optionally, the measurement data can be based on the force and/or pressure between the appliance and one or more attachment devices mounted on the patient's teeth. The monitoring device can process the data to determine whether the measured force and/or pressure are within the expected range corresponding to the patient wearing the appliance.

A monitoring device can include a single force and/or pressure sensor, or a plurality of force and/or pressure sensors. The sensors can be positioned at any location in the appliance, such on an inner surface, an outer surface, a buccal surface, a lingual surface, an occlusal surface, a mesial portion, a distal portion, a gingival portion, or a combination thereof. In some embodiments, the sensors are positioned to be near certain teeth when the appliance is worn. In embodiments where the appliance is an orthodontic appliance, the sensors can be positioned near teeth to be repositioned, e.g., at locations where the appliance is expected to exert force on the teeth. For example, if the appliance is shaped to engage an attachment device mounted on a tooth in order to exert force onto the tooth, a force and/or pressure sensor can be located at or near the location of engagement between the appliance and the attachment device.

Figure 15:
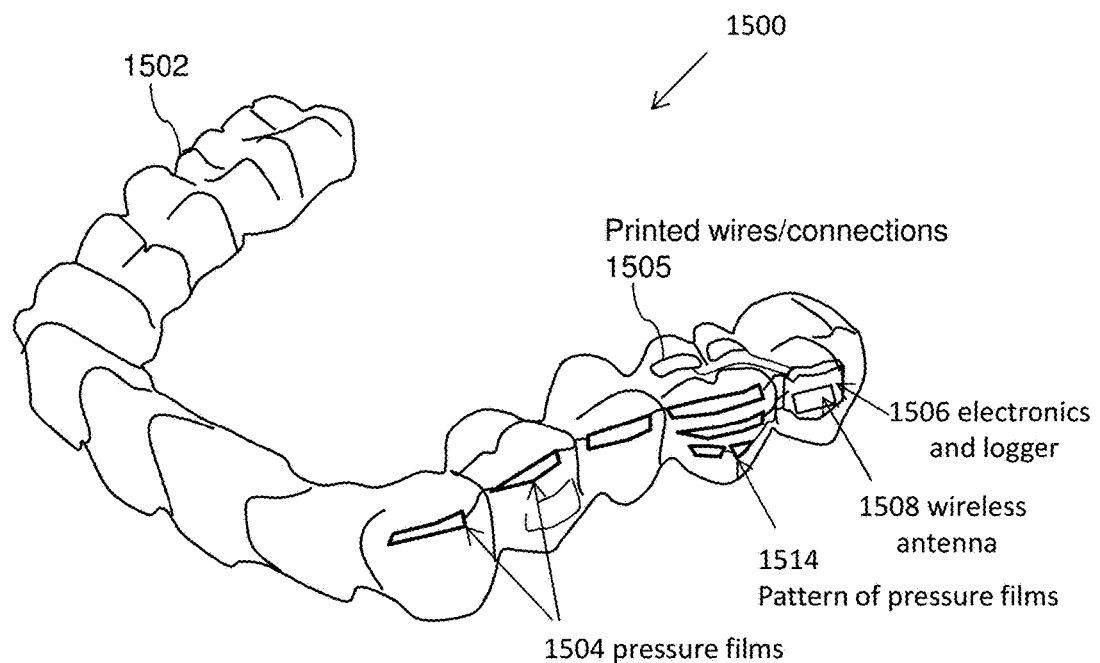
FIG. 15 illustrates an example of a monitoring device configured to measure force and/or pressure between an intraoral appliance and the patient's teeth.

FIG. 15 illustrates a monitoring device 1500 configured to measure force and/or pressure between an intraoral appliance 1502 and the patient's teeth, in accordance with embodiments. The device 1500 includes a plurality of pressure and/or force sensors 1504 (e.g., pressure-dependent resistive films) electrically coupled (e.g., via printed wires 1505 or other connecting elements) to a controller 1506. The plurality of pressure and/or force sensors 1504 can be patterned on the inner surface of the appliance 1502 so as to generate sensor data indicative of the pressure and/or force between the appliance 1502 and the patient's teeth. In some embodiments, the appliance 1502 includes a plurality of teeth receiving cavities and the pressure and/or force sensors 1504 are located on the buccal, lingual, and/or occlusal surfaces of the cavities. The controller 1506 can include components (e.g., as previously described with respect to FIG. 3) configured to process the sensor data to determine whether the appliance 1502 is being worn. Optionally, the controller 1506 can include a wireless antenna 1508 for transmitting the sensing data and/or processing results to a remote device, as described herein.

Figure 16A:
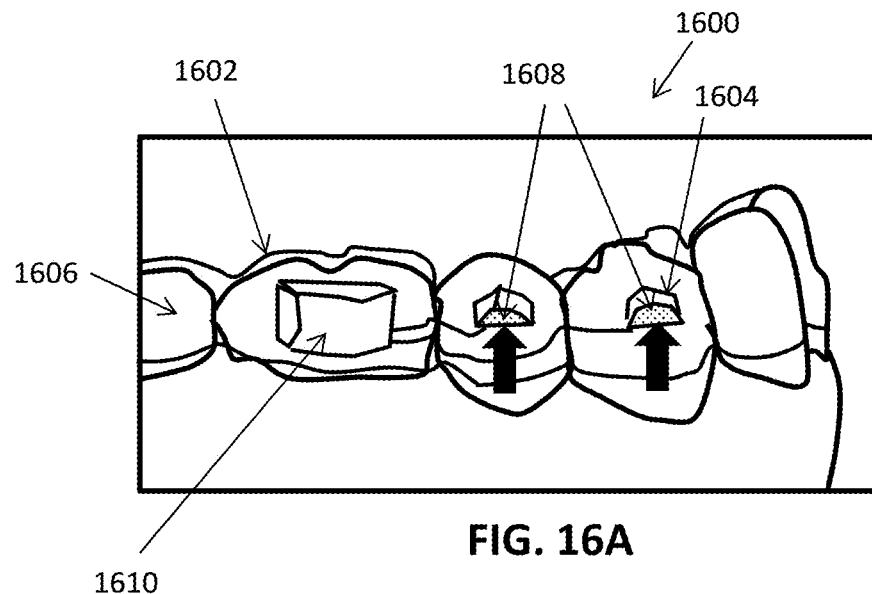
FIG. 16A illustrates an example of a monitoring device configured to measure force and/or pressure between an intraoral appliance and one or more attachment devices on a patient's teeth.
Figure 16B:
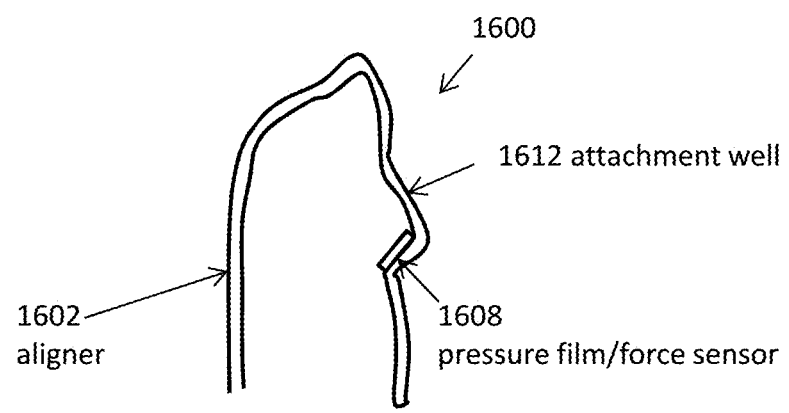
FIG. 16B is a cross-sectional view of the device of FIG. 16A.

FIGS. 16A and 16B illustrate a monitoring device 1600 configured to measure force and/or pressure between an intraoral appliance 1602 and one or more attachment devices 1604 on a patient's teeth 1606, in accordance with embodiments. The device 1600 includes a plurality of pressure and/or force sensors 1608 (e.g., pressure-dependent resistive films) electrically coupled to a controller 1610. The plurality of pressure and/or force sensors 1608 can be patterned on the inner surface of the appliance 1602 so as to generate sensor data indicative of the pressure and/or force between the appliance 1602 and the attachment devices 1604 on the patient's teeth 1606. In some embodiments, the appliance 1602 includes a plurality of teeth receiving cavities formed with one or more receptacles 1612 to receive the corresponding attachment devices 1604 on the patient's teeth, and the pressure and/or force sensors 1608 can be positioned the inner surface of one or more receptacles 1612. The controller 1610 can include components (e.g., as previously described with respect to FIG. 3A) configured to process the sensor data to determine whether the appliance 1602 is being worn.

Any of the apparatuses (e.g., monitoring devices) described herein may be configured to determine mechanical impedance of the teeth and/or intraoral appliance. For example, any of the apparatuses described herein may be configured to derive a mechanical impedance of a tooth, multiple or groups of teeth, and/or the appliance. Generally, mechanical impedance may be referred to as the resistance to motion given an applied force:

$$Z(w)=F(w)/v(w)$$

Where F=force, v=velocity and w=angular frequency.

Figure 16C:
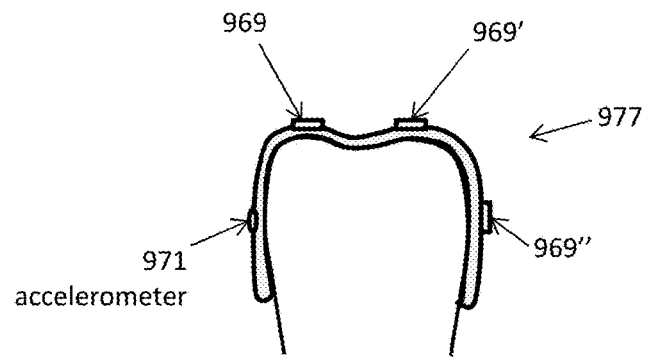
FIG. 16C is an example of an intraoral device configured to measure mechanical impedance of a tooth or teeth.

FIG. 16C illustrates one example of a section through an intraoral appliance 977 (showing in this example as an aligner) including a motion sensor 971 (such as an accelerometer) and one or more force sensors 969, 969', 969". Alternatively or additionally, one or more of the motion sensor and force sensor(s) may be positioned directly on the teeth (including on an attachment adapted to secure the intraoral appliance to the teeth) and may communicate with a processor/analysis engine, battery, communications circuitry, etc. on the aligner.

Figure 16D:
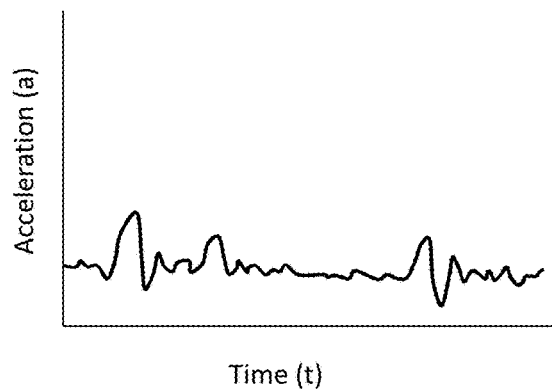
FIG. 16D graphically illustrates the detection of acceleration over time at a particular tooth (or an aligner portion corresponding to a particular tooth).
Figure 16E:
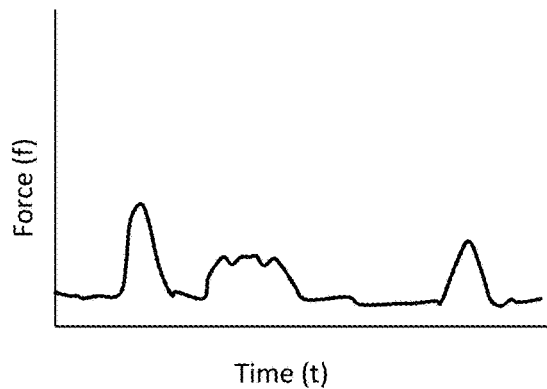
FIG. 16E graphically illustrates the detection of force over time at the same tooth (or aligner region) for which acceleration was determined as shown in FIG. 16D. An intraoral device configured to measure mechanical impedance such as the apparatus shown in FIG. 16C may correlate the acceleration over time and the force over time to estimate mechanical impedance for the tooth.

The processor/analysis engine may then use the motion (e.g., acceleration) data over time, an example of which is shown in FIG. 16D, and corresponding force data over time, an example of which is shown in FIG. 16E, and may correlate this data to estimate mechanical impedance.

Alternatively of additionally, the system may estimate mechanical impedance based on underdamped second order system (e.g., as a logarithmic decrement of an underdamped second order system). In this case, the apparatus may be configured to measure the teeth (and/or appliance) response to a perturbing force, such as an input vibration or force applied to the teeth. For example, the apparatus may be configured to measure the free vibration response to a mechanical impulse input. The apparatus may then determine the peak-to-peak decay of the underdamped oscillation and the period of the system; from these values, the apparatus may then derive the damped natural frequency, the natural frequency, and a damping ratio. In a second order system, these values may define the impedance.

For linear systems, the apparatus may fit parameter of a parametric model of the mechanical impedance to a measured bode plot. For non-linear system, the apparatus may use generalized frequency response functions to analyze non-linear systems (e.g., forced vibrations response, sinusoidal frequency sweeps, etc., including machine learning).

Figure 16F:
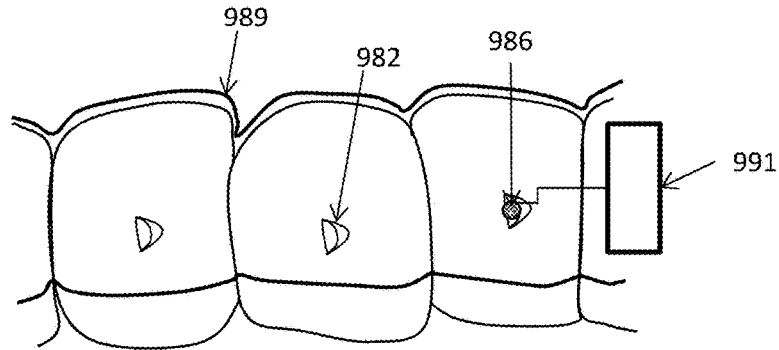
FIG. 16F shows a portion of an intraoral appliance configured to measure mechanical impedance. In this example, one or more motion sensors (e.g., accelerometers) may be coupled to the tooth (as part of the attachment, as shown) and may communicate with electronic components on the intraoral appliance (e.g., memory, processor, power supply, wireless communications, etc.). The apparatus may also include or may be used in conjunction with a mechanical actuator to provide a known (or measured) perturbing vibration, and the processor may use the known force input with the output from the accelerometer to determine mechanical impedance for the tooth/teeth.
Figure 20A:
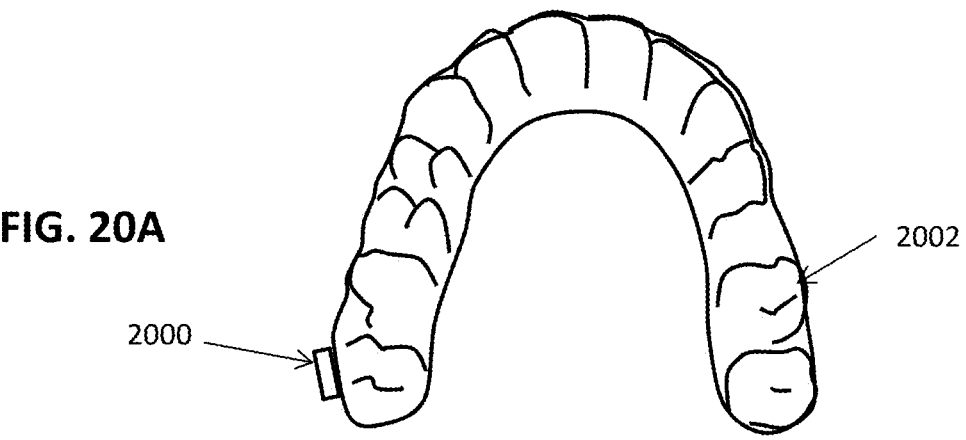
FIGS. 20A through 20D illustrate an exemplary method for fabricating an intraoral appliance with an integrated monitoring device.
Figure 20B:
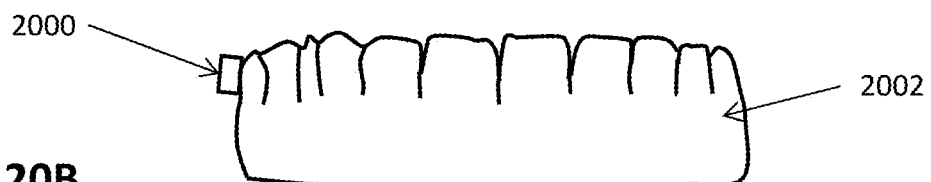
Figure 20C:
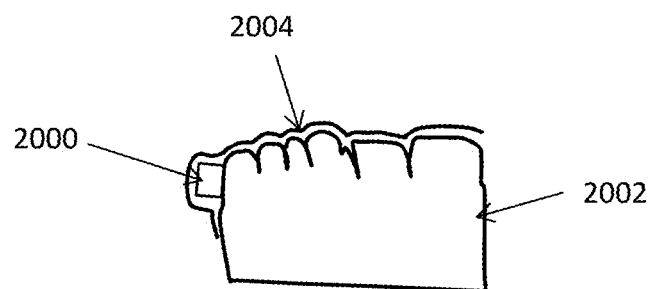
Figure 20D:
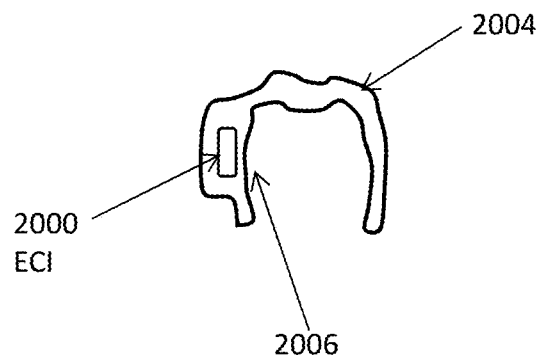

For example, FIG. 16F shows a side view of another example of an apparatus for measuring mechanical impedance of a tooth or teeth. In this example, a plurality of attachments 982 are used to secure an orthodontic appliance (e.g., aligner 989) to the teeth. The aligner includes a processor 991, wireless communication circuitry, and may include additional hardware, software and/or firmware for detecting sensor data to determine mechanical impedance of the teeth and/or aligner. The attachments may include one or more sensors, including motion (e.g., accelerometers) and/or force sensors; these one or more sensors may communicate directly (e.g., via electrical contact) with the processor 991 on the aligner.

In FIG. 16F, this configuration may be used as described above, and/or may be used to determine a frequency response to an applied input signal. For example, any of these apparatuses may include an actuator to apply a vibration or force input to the teeth (e.g., a vibration motor, miniature piston, etc.). The force applied by the actuator may be measured or estimated and used in conjunction with the detected response (e.g., motion/acceleration data). Alternatively, the apparatus my take into account naturally occurring force inputs (e.g., masticatory forces), and may measure or estimate them; as mentioned above, using one or more force sensors. The force data as well as the response movement/acceleration data may be used to determine mechanical impedance.

The resulting mechanical impedance data may then be used to assess the health of the tooth movement.

Figure 17A:
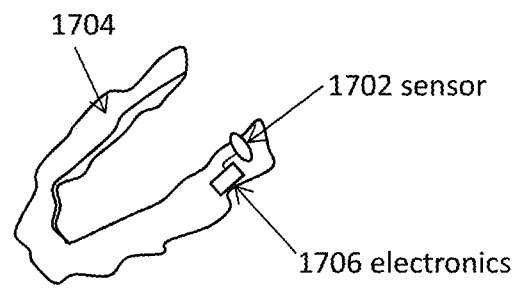
FIG. 17A shows an example of a monitoring device including a gas flow sensor.

Alternatively or in combination, the monitoring devices described herein can include one or more gas flow sensors configured to detect whether the intraoral appliance is being worn based on intraoral airflow. For instance, the gas flow sensor can be a hot-wire anemometer configured to measure airflow associated with breathing, mastication, speech, snoring, and the like. The embodiments herein can also incorporate microfluidic-based gas flow sensors, as desired. Optionally, gas flow sensors can also be used to measure airflow to determine whether the patient is experiencing a sleep apnea event. For example, the monitoring device can determine whether the measured airflow pattern is similar to airflow patterns that occur when the patient is experiencing sleep apnea. This approach can be used in embodiments where the intraoral appliance is a sleep apnea treatment appliance (e.g., a mandibular advancement device), for example. FIG. 17A illustrates a monitoring device 1700 including a gas flow sensor 1702, in accordance with embodiments. The sensor 1702 is integrated into an intraoral appliance 1704. In some embodiments, the sensing portion of the sensor 1702 (e.g., a wire or conductor) extends from the appliance 1704 (e.g., a lingual surface) so as to be exposed to intraoral airflow. The sensing data obtained by the sensor 1702 can be processed and analyzed by other components of the monitoring device 1700 (e.g., controller 1706) in order to determine appliance usage and/or whether patient is experiencing a sleep apnea event.

FIG. 17B illustrates a monitoring device 1720 including a gas flow sensor 1722, in accordance with embodiments. The device 1720 can be substantially similar to the device 1700, except that the sensor 1722 extends across the opposite sides of the appliance 1724 such that the sensing portion is located near the middle of the intraoral airflow. This approach may provide improved sensing accuracy.

FIG. 17C illustrates a monitoring device 1740 including a gas flow sensor 1742, in accordance with embodiments. The device 1740 can be substantially similar to the device 1720, except that the sensor 1742 extends only from one side of appliance 1744. This approach may reduce patient discomfort.

Alternatively or in combination, a monitoring device can include one or more motion sensors configured to detect appliance usage based on movements of one or both of the patient's jaws. Examples of such motion sensors include accelerometers, gyroscopes, piezoelectric film vibration sensors, gravity sensors, and microwave emitters and receivers. The motion sensors can be integrated into an intraoral appliance worn on a patient's upper or lower jaw, or can be distributed across an appliance worn on the upper jaw and an appliance worn on the lower jaw. In some embodiments, the motion sensors are configured to generate data representative of the patient's jaw movement patterns, and the monitoring device processes and analyzes the movement patterns (e.g., using power spectrum and/or kinematic analysis) to determine whether the patterns indicate that the appliance(s) are being worn. Optionally, the monitoring device can distinguish jaw movement patterns associated with different oral activities (e.g., mastication, grinding, speech, etc.).

FIG. 18 illustrates a monitoring device 1800 using motion sensing, in accordance with embodiments. The device 1800 includes one or more motion sensors 1802 integrated into a first intraoral appliance 1804 worn on a patient's jaw (e.g., upper or lower jaw). In some embodiments, the motion sensors 1802 include one or more magnetometers that detect the magnetic field generated by a magnet 1806 integrated into a second intraoral appliance 1808 worn on the opposing jaw. For instance, the device 1800 can include two multi-axis magnetometers used to obtain a six-axis measurement of the relative movements of the upper and lower jaws. In alternative embodiments, rather than using the magnet 1806, the magnetometer(s) 1802 can be used to measure the angle of the patient's jaw relative to the earth's magnetic field, and the angle data can be used to determine whether the appliance is being worn. The motion data generated by the motion sensor(s) 1802 can be used to track jaw movement patterns in order to determine whether the appliances are currently being worn. Other types of motion sensors 1802 can also be used, such as accelerometers, gravity sensors, gyroscopes, or microwave emitters and receivers.

Alternatively or in combination, a monitoring device can include one or more temperature sensors, such as sensors detecting temperature based on infrared radiation, conductive thermistor-based sensors, and the like. The motion detector can determine appliance usage based on whether the measured temperature is within the range of body temperature, e.g., oral cavity temperature. Optionally, this determination can involve comparing the measured temperature with ambient temperature measurements obtained while the appliance is not being worn. In some embodiments, the temperature data is recorded as the raw temperature value. Alternatively, the temperature data can be recorded in binary form (e.g., whether the temperature is within the range of body temperature or not), for example, to save memory space.

Alternatively or in combination, a monitoring device can include one or more strain gauges (e.g., resistive or MEMS-based) to detect the stress and/or strain at one or more locations in the intraoral appliance. The monitoring device can determine whether the measured stress and/or strain values are within the expected ranges for appliance usage. The monitoring device can store the actual stress and/or strain values, or can store just binary data indicating whether or not the appliance is being worn.

Alternatively or in combination, a monitoring device can include one or more pH sensors configured to measure the pH values of fluids (e.g., saliva) in the surrounding environment. The monitoring device can determine whether the appliance is being worn based on whether the measured pH values are within the expected pH range for human saliva, for example.

Alternatively or in combination, a monitoring device can include one or more conductivity sensors configured to measure the conductivity of fluids (e.g., saliva) in the surrounding environment. The monitoring device can determine whether the appliance is being worn based on whether the measured conductivity is within the expected range for human saliva, for example. In some embodiments, the conductivity can be measured over a period of time. This approach can be used to prevent the monitoring device from being deceived by immersion into saliva-mimicking fluids, since the conductivity of human saliva may vary over time based on the body's physiological activities.

Alternatively or in combination, a monitoring device can include one or more humidity sensors configured to detect contact with intraoral fluids (e.g., saliva). The monitoring device can determine whether the appliance is being worn based on whether the measured humidity is within the expected humidity range for the intraoral cavity, for example.

The monitoring devices described herein may be used to measure health information for the patient alternatively to or in combination with detecting appliance usage. Such monitoring devices can include one or more physiological sensors, such as electrocardiography sensors, bio-impedance sensors, photoplethysmography sensors, galvanic skin response sensors, or combinations thereof. For example, a photoplethysmography sensor can be used to measure blood volume changes in the patient's intraoral tissues such as the cheeks or gingiva. As another example, a galvanic skin response sensor can be used to measure the conductivity of intraoral tissues, which may vary based on the minerals released onto the outer tissue surfaces from glands, for example. In some embodiments, the monitoring devices described herein are configured to differentiate between sensor data indicative of appliance usage and sensor data produced by other types of patient interactions with the appliance (e.g., the appliance being held in a patient's hand). Such differentiation can be accomplished by training the monitoring device to distinguish between data patterns indicative of appliance usage and data patterns produced by other interactions, e.g., based on a training data set prior to actual patient monitoring and/or data generated during monitoring. Alternatively or in combination, this differentiation can be performed by other devices besides the monitoring device, e.g., by an external processor performing post-processing on the data obtained by the monitoring device.

FIG. 19 illustrates a method 1900 for monitoring usage of an intraoral appliance, in accordance with embodiments. The method 1900 can be performed using any embodiment of the systems and devices described herein. In some embodiments, some or all of the steps are performed using a processor of a monitoring device operably coupled to an intraoral appliance. Alternatively or in combination, some or all of the steps can be performed by a processor of a device external to the patient's intraoral cavity, e.g., a separate computing device or system.

In step 1910, sensor data is received from one or more sensors operably coupled to an intraoral appliance. The one or more sensors can include any of the sensor types described herein, including but not limited to touch or tactile sensors (e.g., capacitive, resistive), proximity sensors, audio sensors (e.g., microelectromechanical system (MEMS) microphones), color sensors (e.g., RGB color sensors), electromagnetic sensors (e.g., magnetic reed sensors, magnetometer), light sensors, force sensors (e.g., force-dependent resistive materials), pressure sensors, temperature sensors, motion sensors (e.g., accelerometers, gyroscopes), vibration sensors, piezoelectric sensors, strain gauges, pH sensors, conductivity sensors, gas flow sensors, gas detection sensors, humidity or moisture sensors, physiological sensors (e.g., electrocardiography sensors, bio-impedance sensors, photoplethysmography sensors, galvanic skin response sensors), or combinations thereof. The sensor(s) can be physically integrated with (e.g., coupled to, embedded in, formed with, etc.) the intraoral appliance, or can be positioned in the intraoral cavity (e.g., attached to a tooth) so as to interact with the intraoral appliance. The sensor data can be indicative of whether the appliance is currently being worn in the patient's mouth, in accordance with the embodiments described herein.

In step 1920, the sensor data is processed to determine whether the appliance is being worn. For example, the processing step can involve determining whether the sensor data matches a pattern and/or falls within a range of values indicating that the appliance is being worn. Alternatively or in combination, the processing step can involve determine whether the sensor data is different from a pattern and/or lies outside a range of values indicating that the appliance is not being worn. Optionally, the processing step can involve associating the sensor data with a timestamp representing when the data was obtained such that temporal appliance usage information can be determined. The processed sensor data can include appliance usage information indicating whether the appliance is currently being worn, the duration of appliance usage, and/or the date-time the appliance was in use. In some embodiments, step 1920 can alternatively or additionally involve processing the sensor data to determine patient health information, as discussed herein.

In step 1930, the sensor data generated in step 1910 and/or processed sensor data generated in step 1920 is optionally transmitted to a remote device. The remote device can be a mobile device (e.g., smartphone), personal computer, laptop, tablet, wearable device, cloud computing server, or the like. Step 1930 can be performed using wireless or wired communication methods, as desired. Step 1930 can be performed automatically (e.g., at predetermined time intervals) or in response to instructions received from the remote device (e.g., a command to transmit the sensor data and/or appliance usage).

The monitoring devices described herein can be physically integrated into an intraoral appliance in a variety of ways. In some embodiments, the monitoring device is integrated into the appliance during or after fabrication of the appliance. For example, the monitoring device can be attached to an appliance using adhesives, fasteners, a latching mechanism, or a combination thereof after the appliance has been fabricated. Optionally, the appliance can be formed with complementary features or structures (e.g., recesses, receptacles, guides, apertures, etc.) shaped to receive and accommodate the monitoring device or components thereof.

In some embodiments, a monitoring device is coupled to the appliance as a prefabricated unit during or after fabrication of the appliance, such as by being inserted and sealed into a receptacle in the appliance, attached to an appliance (e.g., by a latching mechanism, adhesive, fastener). Alternatively, the monitoring device can be assembled in situ on the appliance during or after appliance fabrication. For instance, in embodiments where the appliance is manufactured by direct fabrication (e.g., 3D printing), the monitoring device can be printed simultaneously with the appliance, inserted into the appliance during fabrication, or after assembled the appliance has been fabricated. Optionally, some of the monitoring device components may be prefabricated and other components may be assembled in situ. It shall be appreciated that the various fabrication methods described herein can be combined in various ways in order to produce an appliance with integrated monitoring device components.

FIGS. 20A through 20D illustrate a method for fabricating an intraoral appliance with an integrated monitoring device, in accordance with embodiments. The method can be applied to any embodiment of the monitoring devices and appliances described herein, and can be used in combination with any of the other fabrication methods described herein. In a first step (FIGS. 20A (top view) and 20B (side view)), a prefabricated monitoring device 2000 is coupled to a positive model 2002 of a patient's dentition. The monitoring device 2000 can be attached using an adhesive and/or a mechanical fastener, for example. Optionally, the monitoring device 2000 can be hermetically sealed prior to being attached to the model 2002. In a second step (FIG. 20C), a material is formed (e.g., thermoformed) over the monitoring device 2000 and model 2002 so as to produce an appliance shell 2004. In a third step (FIG. 20D), the mold 2002 is removed, resulting in an appliance shell 2004 with an embedded monitoring device 2000. Optionally, the monitoring device 2000 can be encapsulated using a biocompatible adhesive 2006 (e.g., a UV-curable glue), a layer of material, or other sealing element.

Figure 21A:
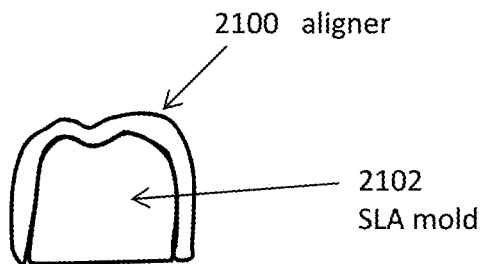
FIGS. 21A through 21C illustrate an example of a method for fabricating an intraoral appliance with an integrated monitoring device.
Figure 21B:
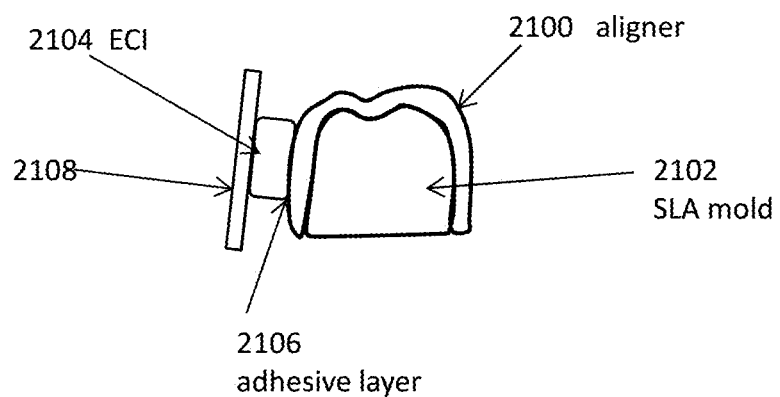
Figure 21C:
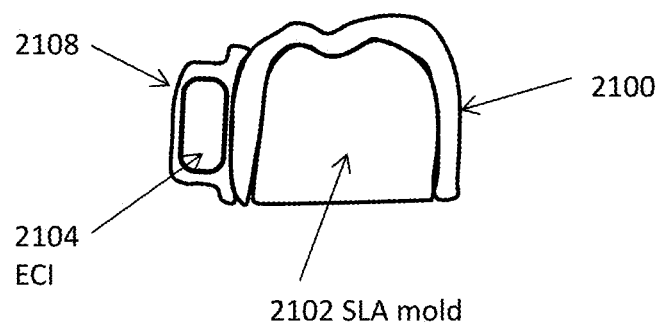

FIGS. 21A through 21C illustrate a method for fabricating an intraoral appliance with an integrated monitoring device, in accordance with embodiments. The method can be applied to any embodiment of the monitoring devices and appliances described herein, and can be used in combination with any of the other fabrication methods described herein. In a first step (FIG. 21A), an appliance 2100 is formed (e.g., thermoformed) over a positive model 2102 of a patient's dentition. In a second step (FIG. 21B), a prefabricated monitoring device 2104 is attached to the appliance 2100, e.g., using an adhesive layer 2106 and/or fastener, and a thermoplastic material 2108 is attached to the outer surface of the monitoring device 2104. In a third step (FIG. 21C), the thermoplastic material 2108 is thermoformed so as to form a cover encapsulating the monitoring device 2104 into the appliance 2100. The positive model 2102 can be removed e.g., before or after the third step.

Alternatively or in combination, the method can involve forming a positive geometry corresponding to the geometry of the monitoring device 2104 on the positive model 2102 (e.g., by 3D printing, CNC milling, etc.), such that the appliance 2100 is thermoformed with a receptacle for the monitoring device 2104. The monitoring device 2104 can then be placed and sealed into the receptacle.

Alternatively or in combination, an intraoral appliance with an integrated monitoring device can be produced by fabricating the appliance (e.g., by indirect or direct fabrication), then attaching a prefabricated monitoring device to the fabricated appliance, e.g., using adhesives, fasteners, a latching mechanism, etc. Optionally, the monitoring device can be hermetically sealed (e.g., by molding) before being attached to the appliance.

Alternatively or in combination, an intraoral appliance with an integrated monitoring device can be fabricated by coupling flexible and/or printed components of a monitoring device onto the appliance during or after forming the appliance. The components can be coupled in various ways, such as thermoforming, laminating, adhesives, coating, and so on.

Alternatively or in combination, an intraoral appliance with an integrated monitoring device can be fabricated by 3D printing a base for the monitoring device, then building up the electronic components for the monitoring device onto the base. In some embodiments, the base is shaped to conform to the geometry of the tooth receiving cavity and/or target tooth where the monitoring device will be located. The 3D printed portions of the monitoring device can be shaped to lie flush with the surface of the appliance to facilitate integration of the monitoring device with the appliance. Alternatively or in combination, an intraoral appliance with an integrated monitoring device can be fabricated by etching the surface of the appliance (e.g., using a masking process) and then depositing conductive inks, stretchable materials, etc. onto the etched portions to build up the electronic components of the monitoring device (e.g., wires, connections, electrodes, etc.) on the appliance.

Figure 22:
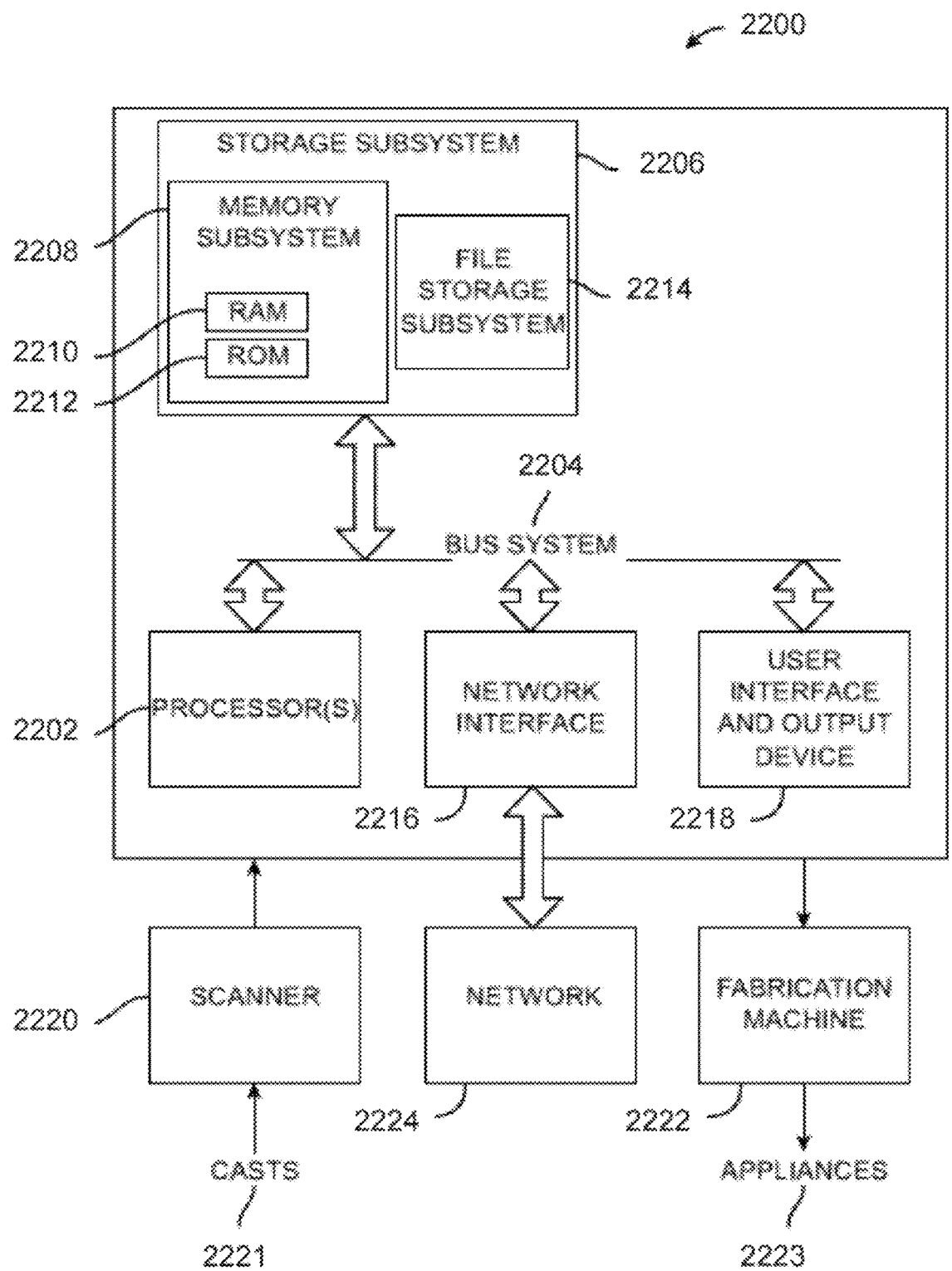
FIG. 22 is a simplified block diagram of an example of a data processing system.

FIG. 22 is a simplified block diagram of a data processing system 2200 that may be used in executing methods and processes described herein. The data processing system 2200 typically includes at least one processor 2202 that communicates with one or more peripheral devices via bus subsystem 2204. These peripheral devices typically include a storage subsystem 2206 (memory subsystem 2208 and file storage subsystem 2214), a set of user interface input and output devices 2218, and an interface to outside networks 2216. This interface is shown schematically as "Network Interface" block 2216, and is coupled to corresponding interface devices in other data processing systems via communication network interface 2224. Data processing system 2200 can include, for example, one or more computers, such as a personal computer, workstation, mainframe, laptop, and the like.

The user interface input devices 2218 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like. Storage subsystem 2206 maintains the basic required programming, including computer readable media having instructions (e.g., operating instructions, etc.), and data constructs. The program modules discussed herein are typically stored in storage subsystem 2206. Storage subsystem 2206 typically includes memory subsystem 2208 and file storage subsystem 2214. Memory subsystem 2208 typically includes a number of memories (e.g., RAM 2210, ROM 2212, etc.) including computer readable memory for storage of fixed instructions, instructions and data during program execution, basic input/output system, etc. File storage subsystem 2214 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 2220 includes any means for obtaining a digital representation (e.g., images, surface topography data, etc.) of a patient's teeth (e.g., by scanning physical models of the teeth such as casts 2221, by scanning impressions taken of the teeth, or by directly scanning the intraoral cavity), which can be obtained either from the patient or from treating professional, such as an orthodontist, and includes means of providing the digital representation to data processing system 2200 for further processing. Scanner 2220 may be located at a location remote with respect to other components of the system and can communicate image data and/or information to data processing system 2200, for example, via a network interface 2224. Fabrication system 2222 fabricates appliances 2223 based on a treatment plan, including data set information received from data processing system 2200. Fabrication machine 2222 can, for example, be located at a remote location and receive data set information from data processing system 2200 via network interface 2224.

EXAMPLES

Any of the monitoring apparatuses described herein, which may be referred to as ECI's and/or data loggers, may be wirelessly connected or connected by a wire ("wire-connected"), or both. For example, when a wired communication with a monitoring apparatus is used, the apparatus may be connected via one or more pins/contacts on an outer surface of the apparatus, either when worn and/or attached to an orthodontic appliance (such an aligner) or after removing from the appliance. Data communication with the monitoring device may be enabled via a reader having one or more mechanical probes that may act as electrical contacts with electrodes/pads in or on the monitoring apparatus. For example, the probes may be located in a case or housing for holding the appliance, which can then separately communicate with a hand-held electronics device such as a smartphone, via Bluetooth. Thus, for example, the monitoring apparatus may connect via a wired connection to a case, and the case may then transmit the data (either raw or unmodified data or modified, analyzed and/or formatted data) to a separate handheld device, such as a smartphone.

The monitoring apparatus may include one or more (e.g., a plurality of) connection pads which may be encapsulated in a self-healing polymer that opens upon insertion of probes and retract to original shape upon removal of the probes providing water sealing. Alternatively or additionally, the connection pads may be exposed out of ECI but grounded/disabled when aligner and/or ECI is in a mouth or in contact with water/saliva. Upon being energized by reader probes, the ECI pads may switch to communication mode.

Any of the monitoring apparatuses described herein may also be configured to be stored in an inactive configuration, in which some or all of the internal contacts are disabled (e.g., disabling the connection between the battery and the processor or other components by a physical break, gap, pin, barrier, etc. that may be removed (e.g., connecting/reconnecting the power source to the circuitry) manually or automatically prior to use, including prior to removing from a case or packaging, prior inserting the device into a subject's mouth, prior to connecting the monitoring apparatus to a dental appliance, etc. For example, the apparatus may include mechanical activation of the monitoring apparatus via removing a tiny pin.

In any of the ECI apparatuses described herein, a mechanical activation/deactivation connection may be used, as described above. Any of these ECIs (e.g., "data loggers") may be configured for wired (direct mechanical/electrical) connection to a reader. The ECI may include internal circuitry (e.g., an ASIC, and/or any of the circuitry described above) one or more sensors, memory, etc.) and a battery that are enclosed or at least partially enclosed, in a housing. A plurality of data pads may be present outside of this housing, so that an electrical connection can be made to the internal circuitry. As mentioned, the entire device, including the pads, may be covered by a protective elastomer (e.g., a self-healing elastomer). This elastomer may be any appropriate material, typically a biocompatible, electrically insulative material that is self-healing or self-sealing after being pierced.

The monitoring apparatus (ECI) operation may be initiated by the user, e.g., patient, dental technician, etc., including mechanically activating using a pin, rod, or the like. For example, prior to use of the ECI, the user may remove an activation rod. When in place, the rod may breaks connection between the battery and the circuit, ensuring zero off current to the ECI circuitry (e.g., ASIC). When the activation rod is removed, the battery may be connected to the ECI ASIC, initiating the data logging sequence. During operation, the ECI ASIC may acquire raw sensor data, as described above. For example, the apparatus may acquire raw capacitance and temperature data at 10 minute intervals, and store each sample in memory (e.g., EEPPROM). The sampling intervals may be counted as individual events, translated into desired time interval display format by the intermediate interface device. Thus, any of the apparatuses described herein may have reduced size/footprint, by eliminating the need for a real time clock and related EEPROM memory. The ECI may include a housing (packaging) consists of a rigid material holding the the internal circuitry and battery part of the assembly, and may also include an elastomeric coating over the housing and the data pads. Data may be retrieved from the devices even when the battery is completely depleted, such as if the patient fails to deliver the ECI back to the dental professional (e.g., orthodontist) within the small battery's lifetime. As an alternatively variation, the operation of mechanical activating mechanism may be reversed from which is described above, so that the ECI apparatus is activated by inserting, rather than removing, an activating rod, pin, etc.

In other variations, a similar mechanical control or switch may be provided by including a spring contact that is held open by a magnetic field, rather than using an activating rod/pin. In this example, the apparatus may be activated by removing it from a package; when in the packaging a permanent magnet (e.g., built into the packaging/housing) may hold a spring contact away from the circuitry, disconnecting the battery from the rest of the circuitry (e.g., ASIC), breaking the connection between the battery and the rest of the circuit, also ensuring zero off-current to the circuitry. Removing the device from the packaging may allow the spring contact to close, activating the data logging sequence, so that the apparatus can acquire data (e.g., capacitance and/or temperature data at a continuous 10 min intervals, and store the data in the memory for later read-out from the data pads).

Although mechanical activation may be used in the context of an apparatus having data contact pads for making a wired connection, any of the apparatuses, including those configured to operate wirelessly, may be configured to mechanical activation.

Figure 24:
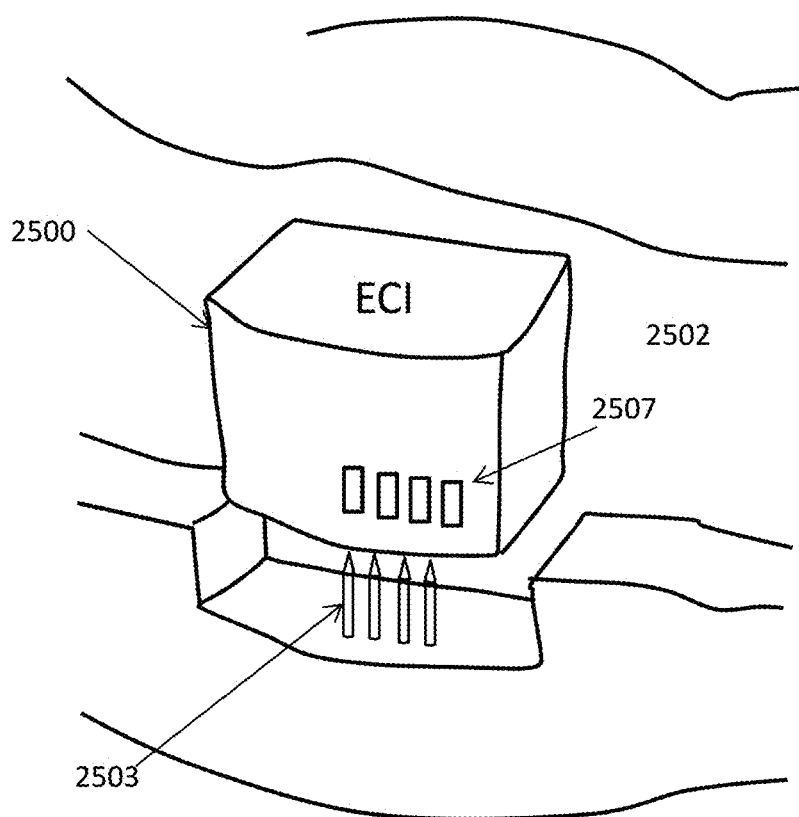
FIG. 24 illustrates one example of coupling an ECI apparatus to an aligner.

In addition, any of the ECI apparatuses described herein may be configured to be inserted/connected to an orthodontic appliance (such as an aligner) by the user or a dental professional. For example, FIG. 24 illustrates an example of an ECI apparatus 2500 that can be inserted onto an aligner 2502. In this case, the ECI apparatus shown is configured for a wired connection (via the pads 2507), however wireless ECI apparatuses may be similarly configured for connection onto an aligner 2502. The aligner may therefore include on or more retaining features, as described above, including pins 2503, as shown in FIG. 24. In some variations, the retaining feature on the aligner may make the mechanical connection between the battery and the circuitry. In some variations, the pins may connect to one or more sensors on the aligner. The pins may penetrate an over molding material, which may be present on any of the variations (including the wireless and wired connection devices).

As mentioned, data may be retrieved from any of these apparatuses using an intermediate interface device such as a housing or case. When the ECI apparatus is configured to make a wired connection, the intermediate device may be fitted with sharp probes to penetrate the over mold elastomer and make electrical contact with any data pads on the PCB. The intermediate device may then retrieve, process, calibrate, and encrypt the data as needed, then transmit to a handheld device such as a smart phone, e.g., via Bluetooth. The data can then be displayed on the smartphone or other display medium using custom applications software, which the patient and/or orthodontist may be able to download for execution on the smartphone or other mobile device In any of the variations described herein, the same pins can be used for connecting and as a conductivity sensing probe for detection of saliva medium.

Figure 25:
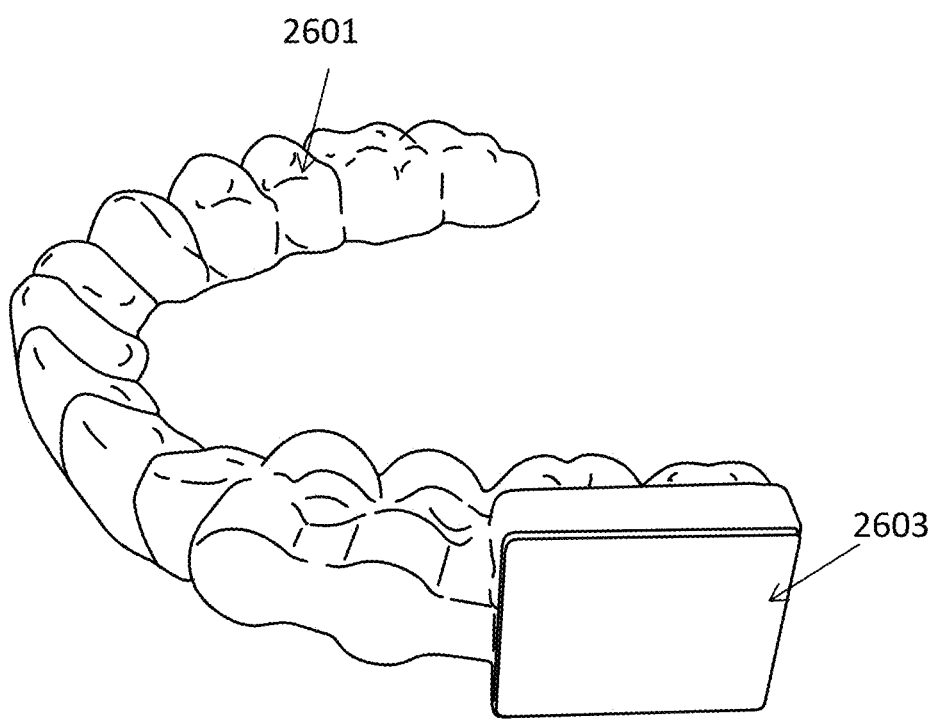
FIG. 25 shows an exemplary prototype of an ECI apparatus coupled to an aligner.

Although FIGS. 24 and 25 illustrate the connective pads as covered by the over molding material, in some variations the connection pads may be exposed. For example, the connection pads may be exposed out of ECI but grounded/disabled when Aligner and ECI are in the user's mouth or in contact with water/saliva. Upon being energized by reader probes the ECI pads may switch to a communication mode during which data may be transferred.

Any of the devices described herein may also or alternatively be connected by a wireless connection. FIG. 25 illustrates one example of an ECI prototype constructed as described herein, including one or more temperature and capacitive sensors. In this example, the ECI 2603 is connected to an aligner (shell 2601). In FIG. 25, the prototype is relatively large; it may be much smaller in practice, for example, by reducing the size of the processor, sensors and other internal components. For example the prototype shown in FIG. 25 may include a Texas Instruments FDC1004 capacitive-to-digital converter (with a footprint of 10×8 mm); this footprint may be significantly reduced in size, e.g., using QFN rather than SOP package. The data logger may include an on-chip temperature sensing data logger (e.g., an NFC type, such as a THOR data logger). The exemplary prototype shown in FIG. 25 may be wirelessly connected to an intermediate device, and therefore a handheld electronics device such as a smartphone.

Figure 26:
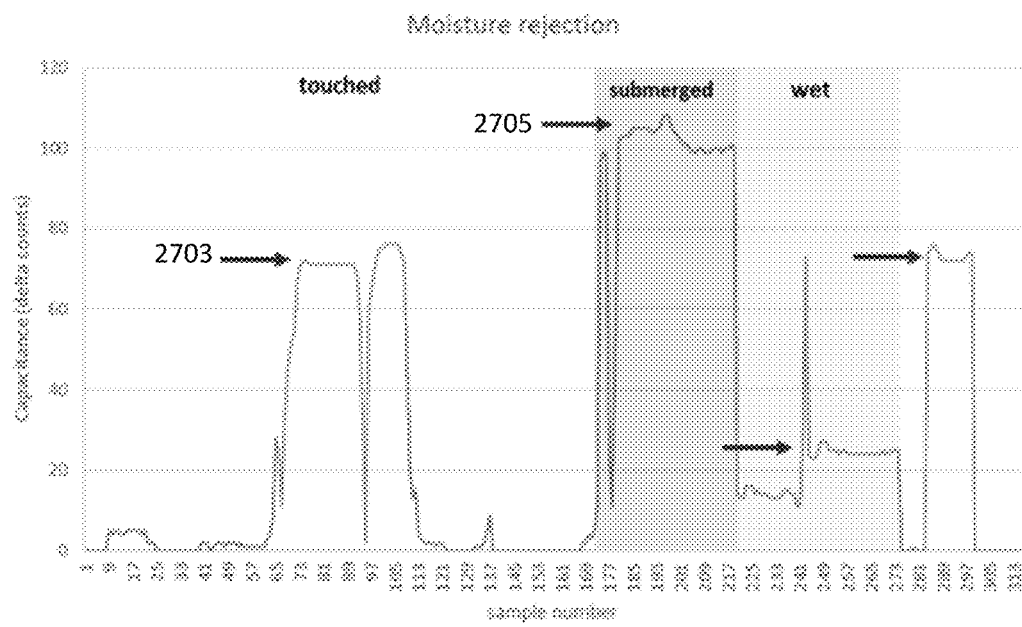
FIG. 26 graphically illustrates the use of a capacitance sensor to detect when an aligner is being worn by a user, and/or is submerged in a fluid (e.g., water).
Figure 27:
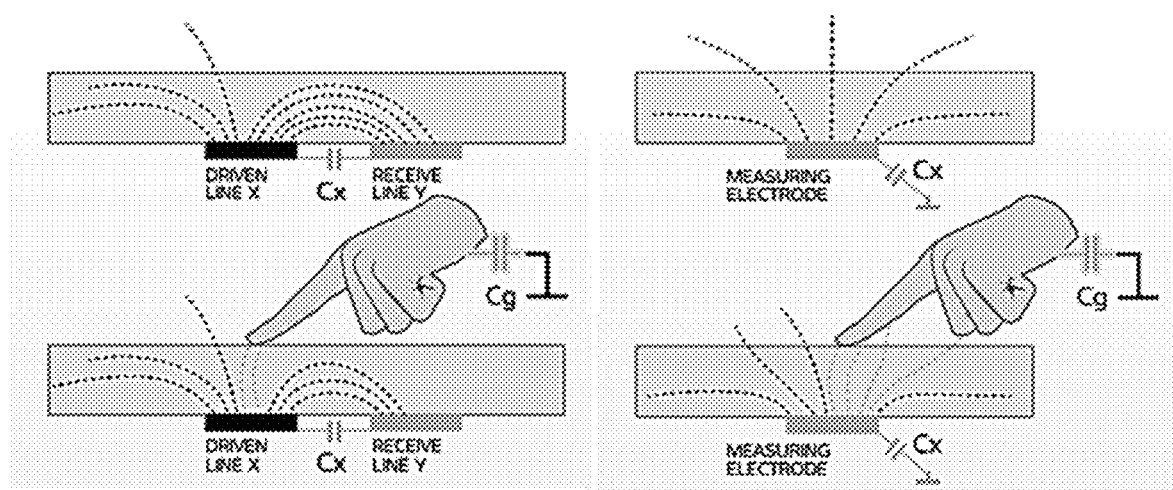
FIG. 27 graphically illustrates mutual capacitance measurements (on left) and self-capacitance measurements (on right).

In any of the apparatuses described herein, the ECI may include a capacitive sensor, which may be configured to accurately determine when the apparatus is present on a tooth/teeth, rather than outside of the mouth, even when submerged in water or other material that may mimic saliva. For example, a prototype such as that shown in FIG. 25 was used as a proof-of-concept to show that capacitance data may be used to determine when an oral appliance was present in the mouth of the user, rather than just submerged (or outside of the mouth). In FIG. 26, capacitance (and temperature) was recorded using the device of FIG. 25 every 5 minutes for fifty-four hours, while subjecting the device to different conditions and looking at the capacitance. As shown, the apparatus is able to distinguish between being worn ("touched" 2703) and submerged in saline ("submerged 2705). As discussed above, the capacitive sensor configuration may be configured to be mutual capacitance measurements or self-capacitance measurements (see, e.g., FIG. 27, left and right, respectively). The capacitance sensor may saturate, however using the proper frequency range and/or ground size may permit the capacitance detector circuitry to distinguish between saturation due to being in the mouth versus being submerged in a fluid.

Figure 28:
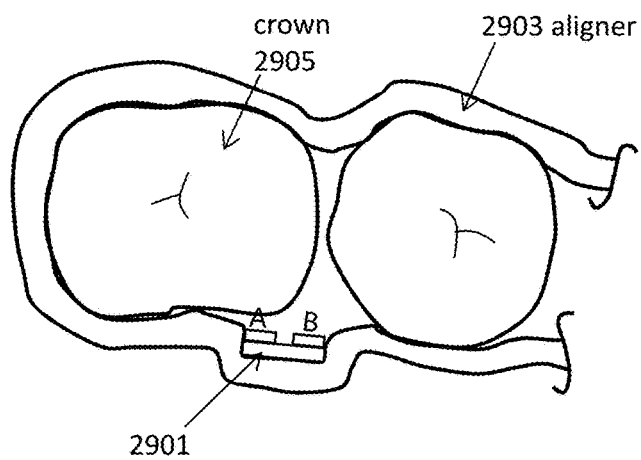
FIG. 28 shows an example an ECI apparatus having a pair of capacitive electrodes.
Figure 29A:
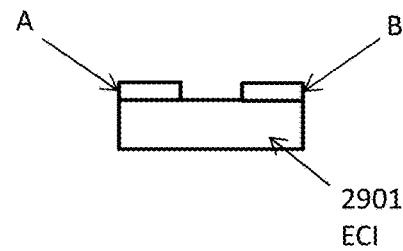
FIG. 29A shows an enlarged view of the sensing electrodes on an ECI apparatus.
Figure 29B:
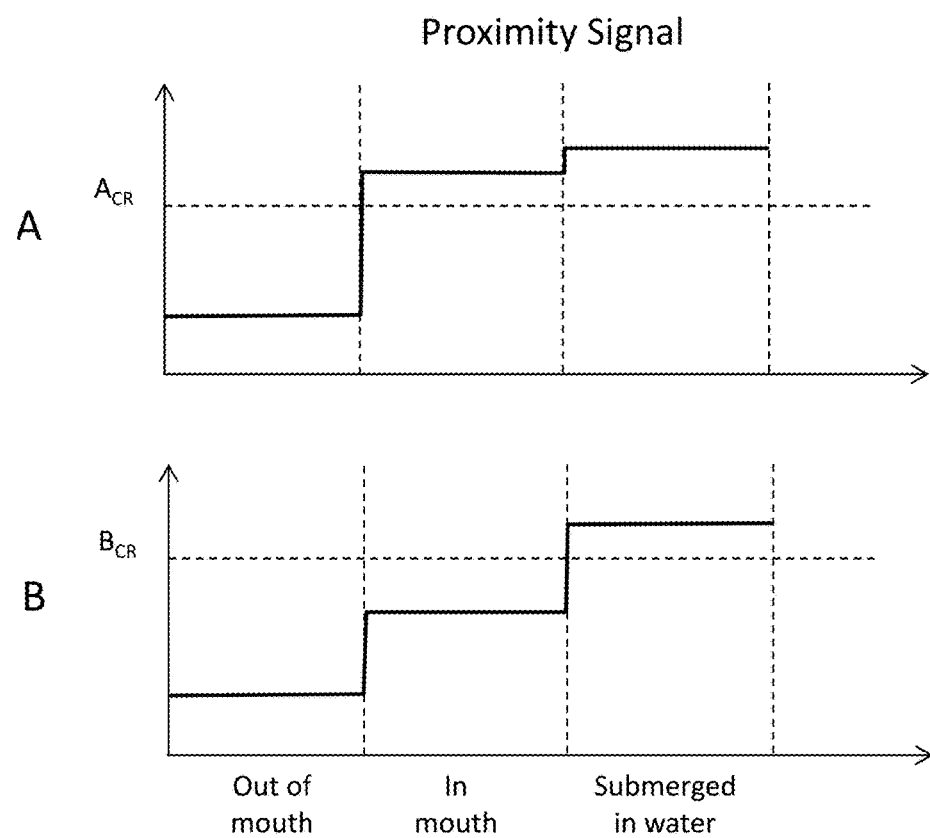
FIG. 29B illustrates the use of capacitive signals from different sensing electrodes to distinguish wearing of an appliance including an ECI apparatus as described.

For example, FIGS. 28 and 29A-29B illustrate one example of an ECI that is configured to distinguish between being worn and other conditions that may otherwise provide capacitive signals similar to those provided when in a fluid solution but not worn. In FIG. 28, the ECI 2901 is shown worn on a subject's teeth 2905 as part of an aligner 2903. The aligner in this case is shown having two sensing electrodes (A and B). The first electrode (A) is configured to be in close proximity to a crown of a tooth when the aligner is worn. The second (B) is configured to be 'far' proximity to the crown of the tooth when worn. FIG. 29A shows a schematic of the ECI, including the A and B sensing electrodes. FIG. 29B illustrates how capacitive signals from these sensing electrodes may be used to distinguish when the device is actually being worn in the mouth, versus when the ECI is out of the mouth or submerged in a saliva-like environment. The logic used to distinguish these conditions may be used to determine a more accurate 'worn' or 'not worn' metric that may be output by the ECI or by software/firmware/hardware in communication with the ECI (e.g., from an application software running on a smartphone, etc.). In FIG. 29B, the signal from the A contact sensor is shown aligned with the signal from the B contact sensor. In this case, three conditions are shown, as well as rough signal amplitudes. When the ECI is out of the mouth, the signal on the A sensing electrode is low; similarly, the signal on the B sensing electrode is low. When the device is worn as shown in FIG. 28, the signal on the A sensing electrode is high (greater than a threshold amount, ACR), and the signal on the B sensing electrode is higher than when out of the mouth, but lower than a threshold (BCR). When the device is submerged in water, however, the signals on both the A sensing electrode and B sensing electrode are high, above the ACR and BCR thresholds. Thus, the apparatus may distinguish between in, out and submerged cases, by rejecting readings when A>ACR and B>BCR as false positives. When both A and B are below their thresholds the device is out of the mouth, and when the A signal is above threshold but the B signal is below threshold, the device may be determined to be in the users mouth.

FIGS. 30A-30C illustrate another example of a method for discriminating between these conditions (in mouth, out of the mouth, and submerged). In this example, the apparatus may again include a pair of sensing electrodes "A" 3001 and "B" 3003, however they are positioned on either side of a tooth on the aligner, and a complex impedance measure, Z, may be taken between them. This "guard" electrode configuration may use short detection pulses to distinguish between false positive readings. This signal may be used in conjunction with proximity sensing to increase the specificity of the detection. The placement of the sensing electrodes may be optimized to minimize the likelihood of false negatives (e.g., shorting by saliva). For example, the electrodes may be placed at the ends of the arch, as shown in FIG. 30C. In this configuration, the complex impedance, Z, may be 0 when the electrodes are placed in water, rather than against the teeth. As shown in FIG. 30D, when the proximity sensor shows that the real capacitance is low, the apparatus is out of the mouth; when the proximity sensor shown a high or moderately high capacitance, and the complex impedance measurement is low, the apparatus is likely submerged in a solution (e.g., of water), and thus these measurements can be rejected as false positives.

Figure 31A:
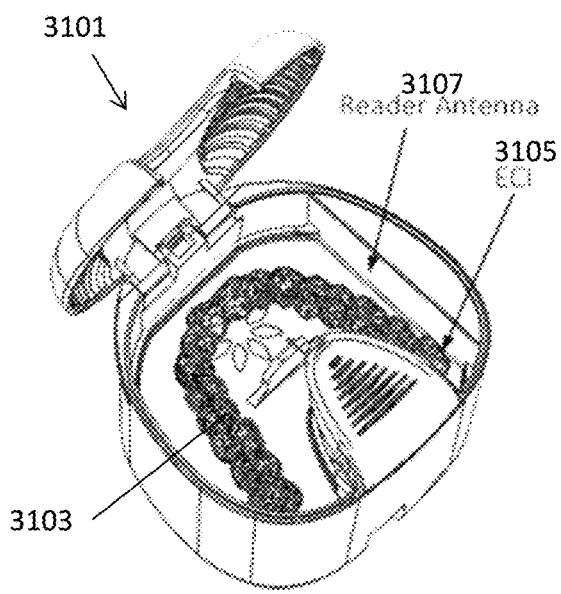
FIGS. 31A-31D illustrate views of one variation of an aligner case configured as an intermediate device for coupling a near-filed signal (NFC) from an ECI apparatus for output as a Bluetooth signal to a phone.
Figure 31B:
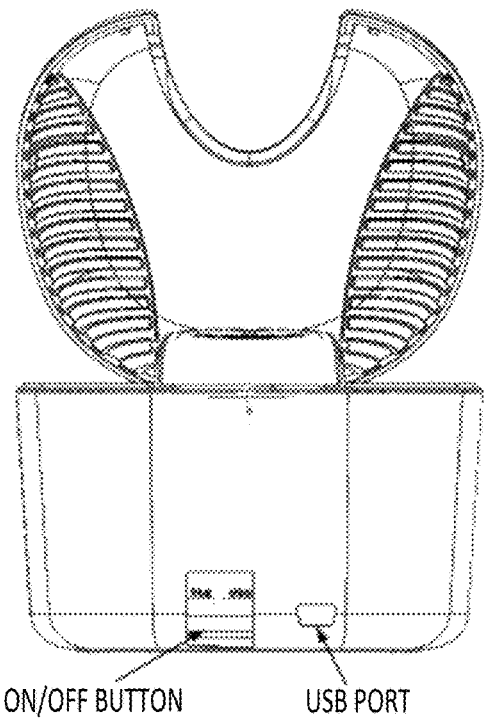
Figure 31C:
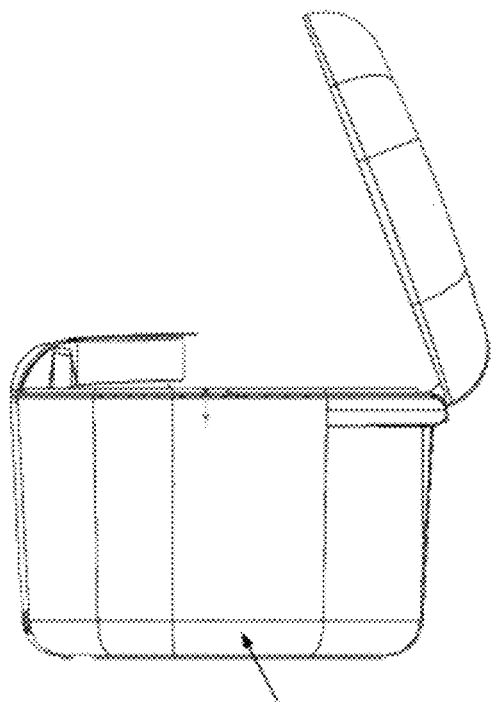
Figure 31D:
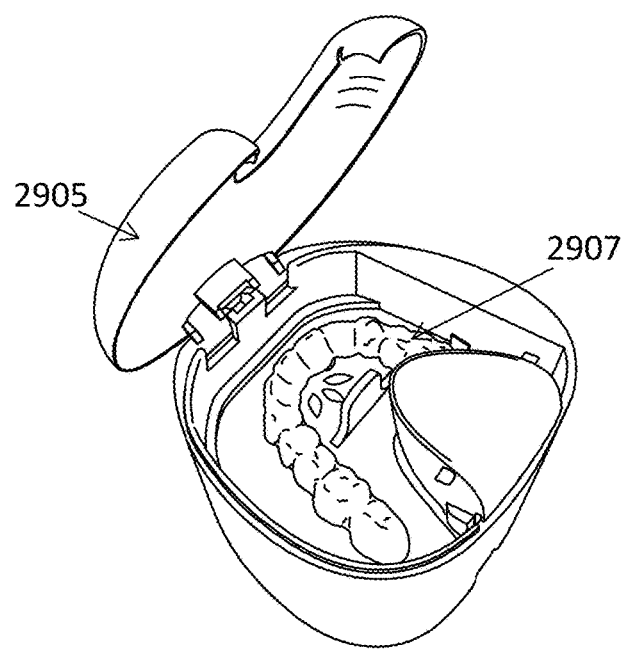

When the ECI apparatuses described herein wirelessly communicate data (e.g., data output) to a handheld device, such as a smartphone, an intermediate apparatus such as a case or container, which may hold either just the ECI module or apparatus, and/or it may hold the ECI apparatus and an appliance (such as an aligner) to which the ECI apparatus is attached. FIGS. 31A-31D illustrate one example of a container that acts as an intermediary device, receiving near field communication signals from the ECI module, and transmitting these signals to a smartphone or other handheld device by Bluetooth. Because of the relatively small size of the ECI apparatus, any antenna component used for wirelessly transmitting signals must also be small; this may pose a problem for directly communicating with a smartphone or other apparatus, as it may be difficult to align the antenna of the ECI apparatus with the antenna of a smartphone or other hand-held electronics device. In this case, a case or holder such as that shown and described in FIGS. 31A-31D may be used to both securely hold the appliance and ECI and to transfer any data recorded by the ECI from the ECI to the case and then on to a mobile devices such as a smartphone, transferring the data first as NFC from the ECI to the intermediate case, then as BLE from the intermediate case to the smartphone. The case or other intermediate device may hold the ECI in a predetermined position, including in alignment with one or more antenna. Note that data may be transmitted between the ECI, case and mobile device in an ongoing manner or sequentially (e.g., delaying transmission between the case and the mobile device); delaying transmission may be helpful for determining when the receiving device (e.g., mobile device) is ready to receive the data, and the intermediate device may hold onto the data until the receiving device indicates it is ready. In FIG. 31A, the aligner 3103 fits into the case 3101 so that the ECI 3105 is aligned with a reader antenna 3107 for reliable transmission via NFC. The intermediate device, such as a case, may be passive (e.g., transferring on the data) or it may be active, e.g., modifying, filtering, annotating, analyzing, averaging, etc. the data.

Figure 34A:
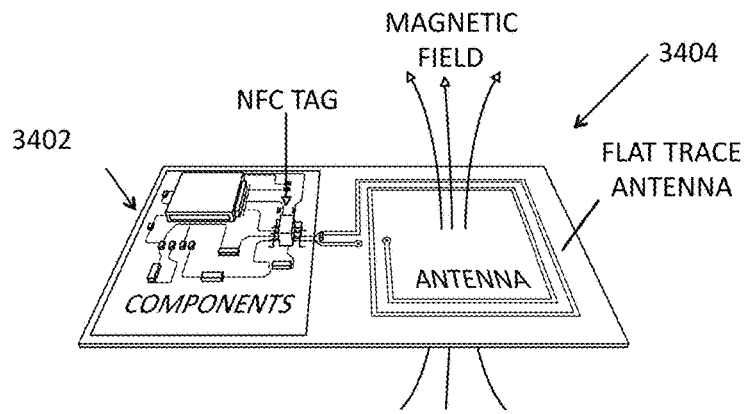
FIGS. 34A and 34B illustrate a trace antenna and the use of a trace antenna to read data from an ECI, respectively.
Figure 34B:
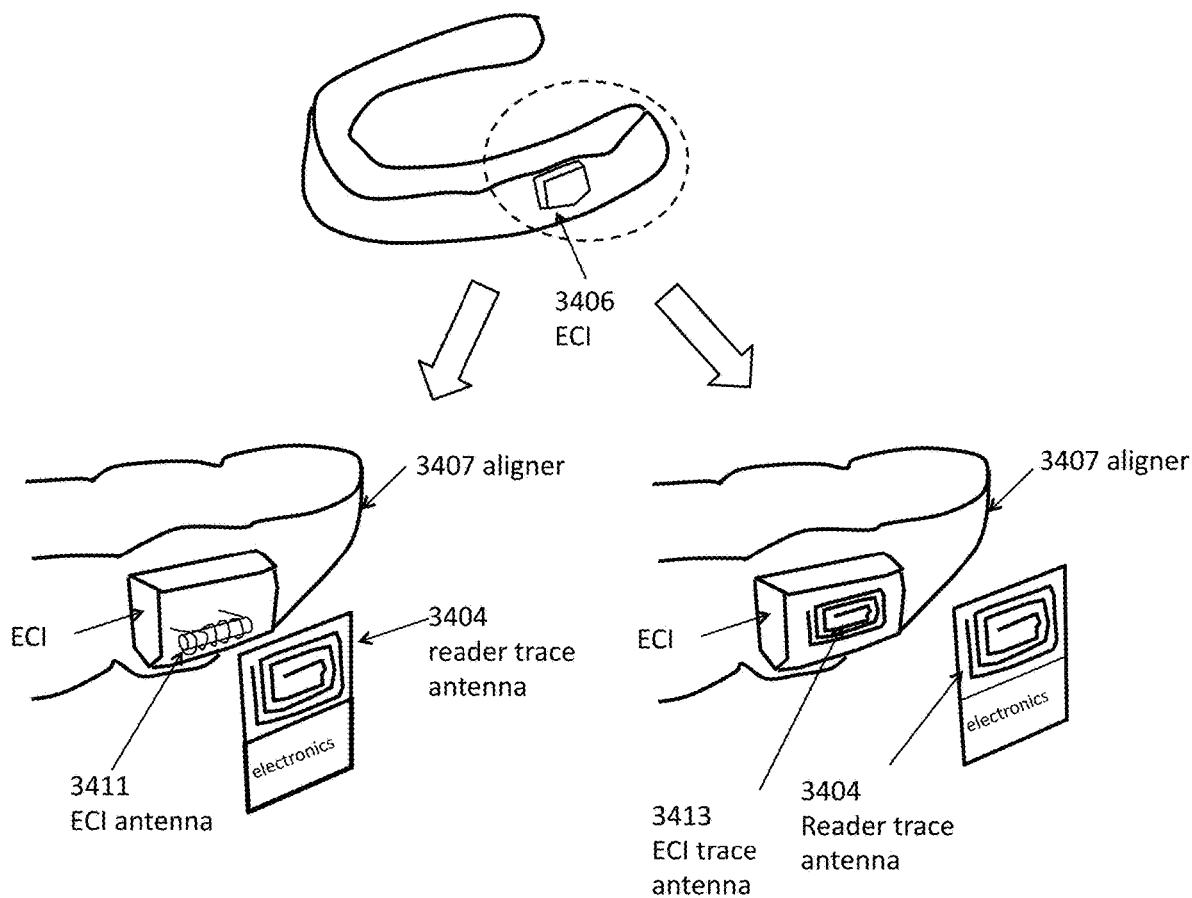

In general, when the ECI apparatus is configure to wirelessly transfer data, the near-field communication antenna (NFC antenna) may be a flat antenna, such as a trace antenna, and/or it may be a coil antenna. FIGS. 34A and 34B illustrate a flat (trace) antenna and the user of such an antenna to transfer data from an appliance incorporating an ECI data recorder. In FIG. 34A, the trace antenna is formed on a substrate (e.g., PCB substrate) and forms a loop 3404 (or multiple loops) and connects to antenna circuitry 3402. The trace antenna produces a field that is substantially transverse to the plane of the substrate. In FIG. 34B the aligner 3407 may be aligned with the attached ECI 3406 adjacent to the antenna loop 3404. In FIG. 34B, two separate NFC antennas are shown in alternative views of the ECI. In the upper portion, the ECI antenna is a coil antenna 3411; the antenna in the lower ECI is a trace antenna 3413.

FIG. 35A illustrates an enlarged view of a generic coil antenna (e.g., a coil wound around a ferrite rod) that may be used for NFC; FIG. 35B shows an example of an ECI and reader, both of which use coil antenna. In FIG. 35B, the ECI antenna 3505 includes a ferrite core, as does the coil antenna on the reader 3507. Any of the readers (including intermediate devices such as holders, etc.) may use any appropriate antenna, including coil antennas and trace antennas. In FIGS. 34B and 35B the readers may be used while the appliance (shown as an aligner) is attached to the ECI.

Figure 36A:
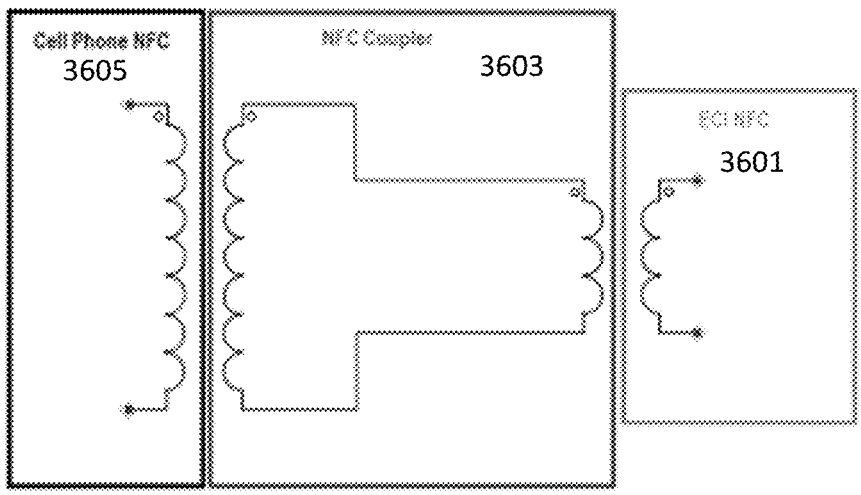
FIG. 36A shows a schematic of a circuit diagram for an NFC coupler coupling between an ECI apparatus and a smartphone.
Figure 36C:
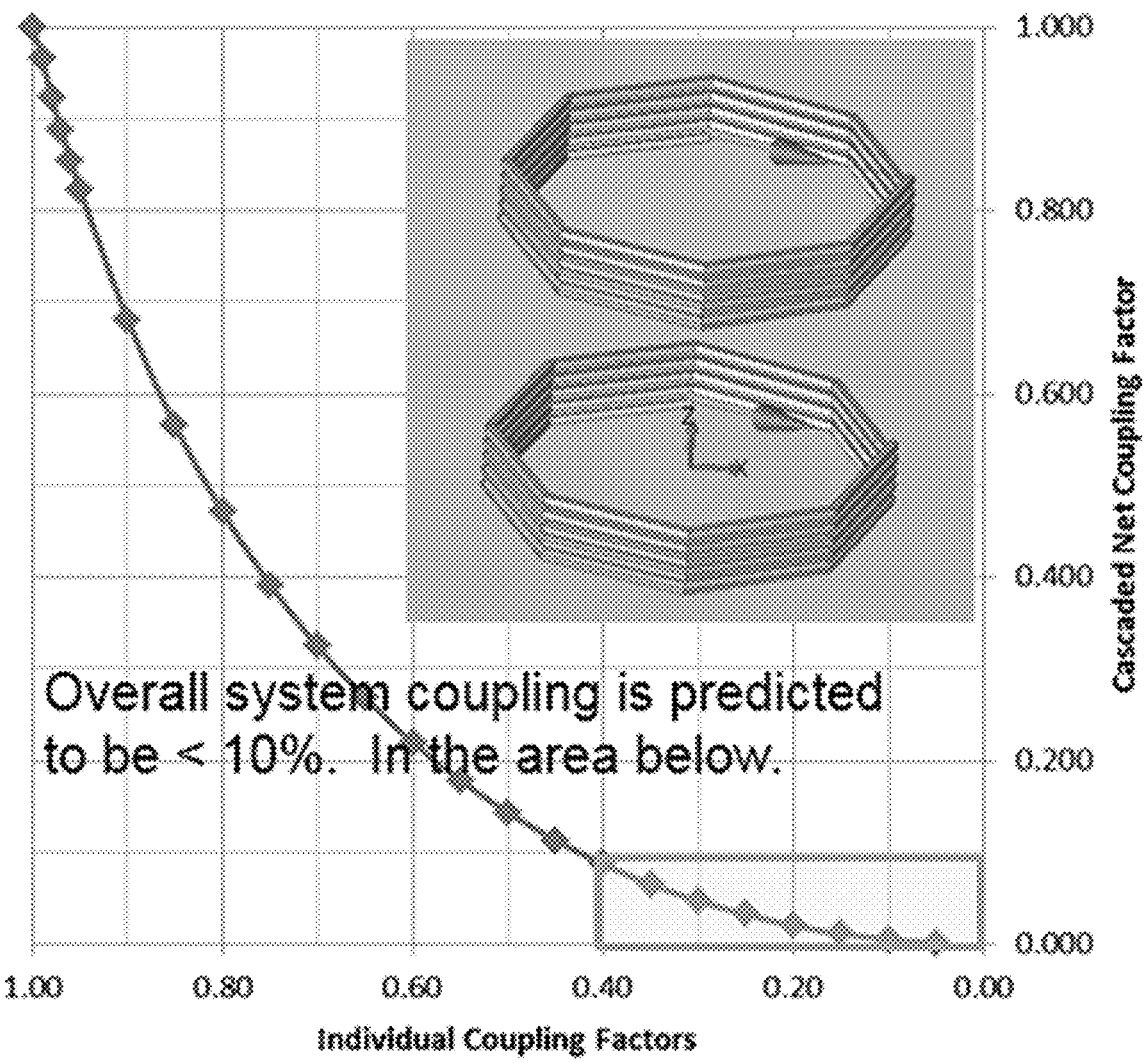
FIG. 36C illustrate overall system coupling between NFC antennas.

As mentioned, there is typically a size discrepancy between the NFC antenna in the ECI apparatus and the antenna in a phone (e.g., smartphone) and other handheld electronics device. Thus, the energy transfer efficiency between a relatively large NFC loop antenna such as may be present in a smartphone and the much smaller ECI loop antenna (e.g., typically only as large as a tooth width) maybe extremely low, including less than 1% due to the antenna size mismatch. Thus, it may be beneficial to use an energy coupler, including as part of an intermediate device (e.g., booster, etc.) which may be configured as a case, mount, holder, or otherwise. FIGS. 36A-36C illustrates a passive NFC energy coupler that may be used. In FIG. 36A, the circuit diagram illustrates the use of a NFC coupler 3603 between an ECI apparatus NFC antenna 3601 and the antenna of a smartphone 3605. Any appropriate antenna may be used as part of the NFC coupler, including a toroid ferrite coupler 3607 having an air gap 3609 in the ferrite core, as shown in FIG. 36B; the ECI (or the NFC antenna of the ECI) may be placed within the air gap. FIG. 36C illustrate the overall system coupling prediction using an NFC coupler.

Figure 37A:
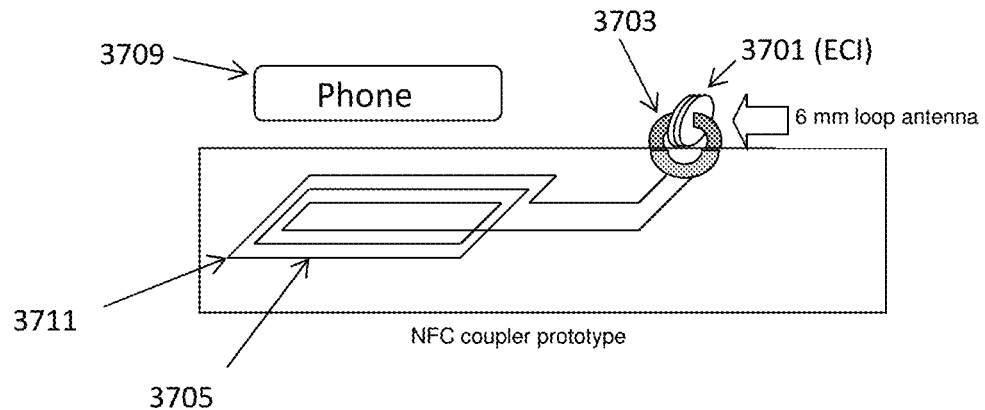
FIGS. 37A and 37B illustrate, schematically, an NFC coupling device.
Figure 37B:
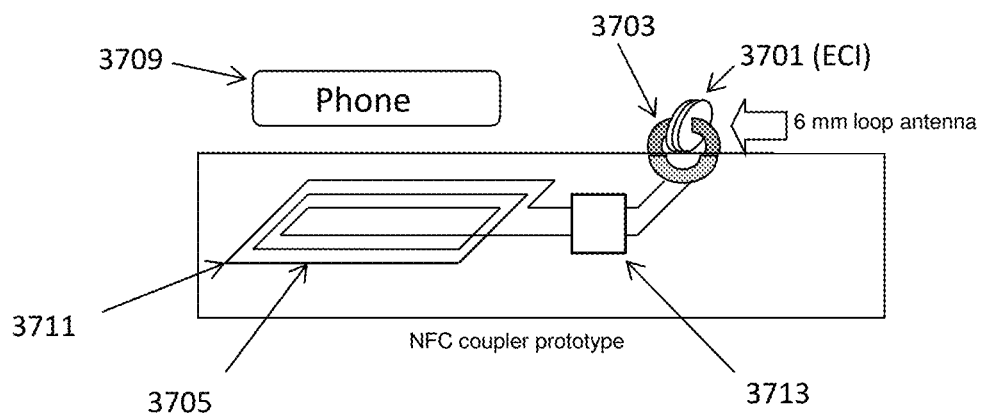

FIGS. 37A and 37B illustrate the use of an NFC to NFC coupler prototype that may be used as an intermediate device. As shown in FIG. 37A, an ECI apparatus (shown schematically as having a coil antenna) 3701 is positioned within range of an NFC antenna 3703, shown in this example a coil antenna having an air gap with a ferrite coil (e.g., a 6 mm loop antenna). The signal received from the NFC antenna is then retransmitted using second antenna 3705 of the NFC coupler to transmit by NFC to a phone 3707 placed in range to the second, larger antenna 3711. As will be described in FIG. 39, below, the first antenna may be matched to the ECI antenna and the second antenna may be matched to the antenna in the phone. In addition, the NFC coupler apparatus may provide alignment between the phone antenna and the second antenna 3711 and the ECI antenna and the first antenna, and may hold the phone and/or the ECI securely in the position. The prototype shown in 37B also includes indicates that additional circuitry (e.g. amplifiers, filters, etc.) 3413 may be used to modify the data signal received from the ECI before it is passed on to the phone. In general, any signal processing may be performed at this stage, or the signal may simply be passed. In one example a 3 dB attenuator is positioned between the first antenna 3703 and the second antenna 2711.

Figure 38:
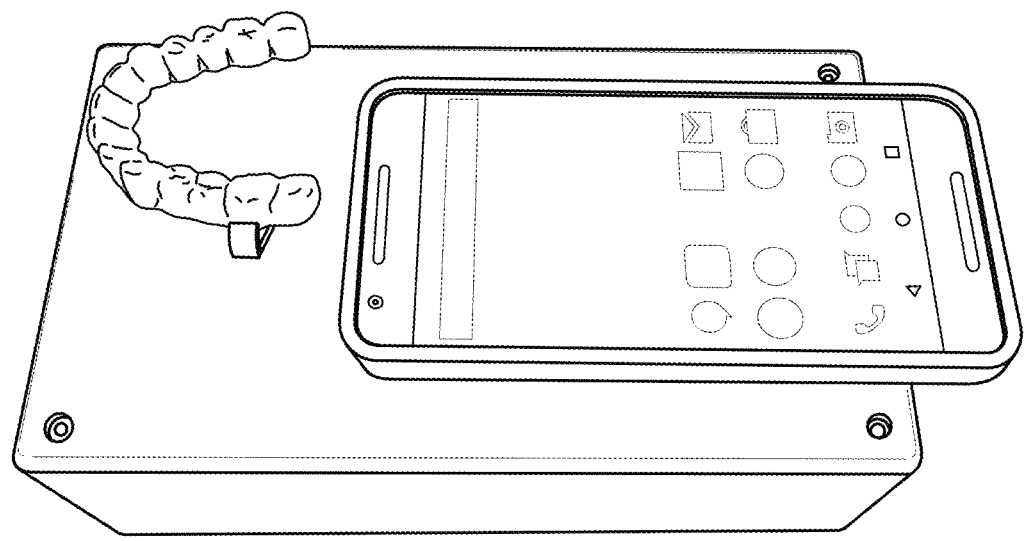
FIG. 38 illustrates a prototype of an NFC coupling device such as the one shown in FIG. 37A.
Figure 39:
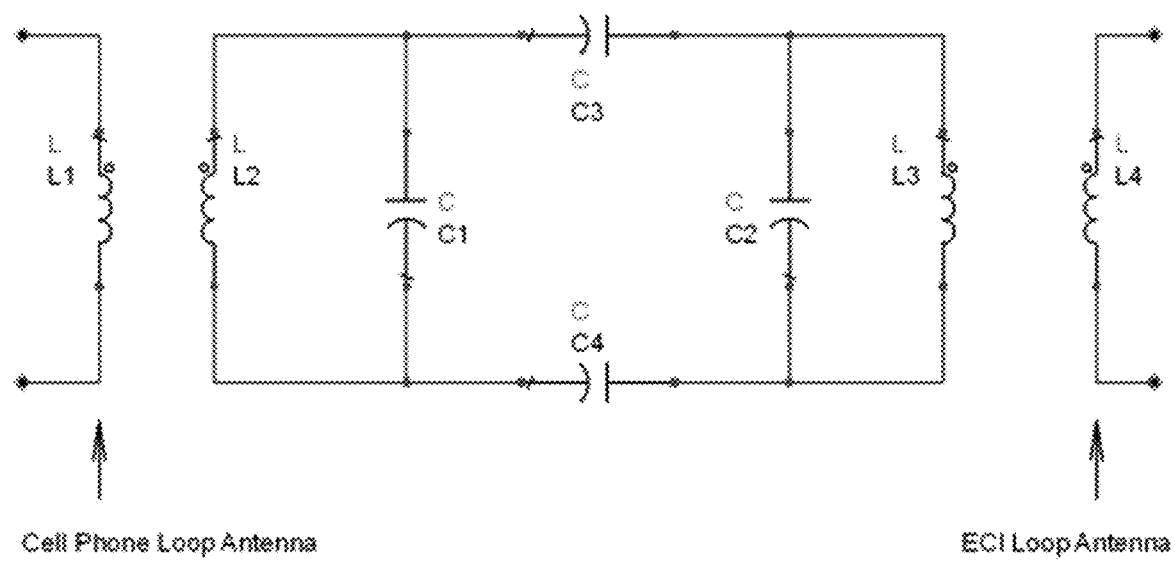
FIG. 39 is an exemplary circuit diagram of an NFC coupling device.

FIG. 38A shows a prototype of the NFC coupler similar to that schematically illustrated in FIGS. 37A and 37B. In FIG. 38, an aligner having an ECI is placed on the NFC coupler so that the ECI antenna is aligned with the NFC antenna of the NFC coupler (not visible in FIG. 38). A phone receiving the signal passed on the NFC coupler is positioned over the phone antenna region of the NFC coupler. FIG. 39 shows a schematic circuit diagram of the apparatus of FIG. 38. In this example, a pair of shunts (C1, C2) and a series of capacitors (C3, C4) transform the inductive impedance of both of the NFC coupler coils to a resistive impedance at the center of the circuit, greatly eliminating the impedance mismatch losses in the system.

Figure 32:
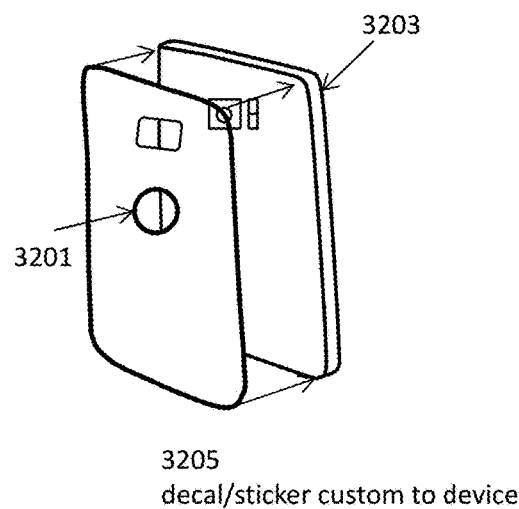
FIG. 32 illustrates one example of a system for transmitting data directly from an ECI to a smartphone.

In addition to transfer of data from the ECI by an intermediate device such as a case or other relay apparatus, in some variations, the ECI may be configured (in some variations in conjunction with other system components, including hardware, software and/or firmware) for direct transfer of data from the ECI to a mobile, handheld device such as a smartphone (e.g., NFC to NFC communication or alternatively, NFC to Bluetooth or other wireless protocol). For example, FIG. 32 illustrates a first example of a system for transmitting data directly from an ECI to a mobile handheld device. In FIG. 32, a marker or guide (e.g., sticker, decal, phone cover/case, sleeve, etc.) may indicate a position 3201 or location for placement of an ECI or aligner/appliance and ECI on the phone 3203 to reliably transfer data (e.g., via NFC) from the ECI apparatus to the smartphone. In FIG. 32 the guide markings are part of a decal 3205.

Figure 33A:
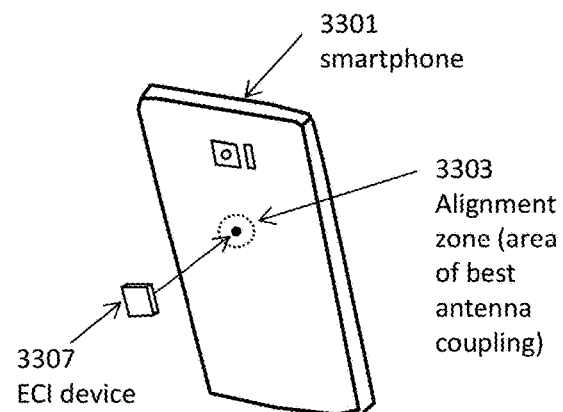
FIGS. 33A-33C illustrate an example of a system for transmitting data directly from an ECI to a smartphone using a holder/clip tool to hold the ECI in alignment with the antenna of the phone.
Figure 33B:
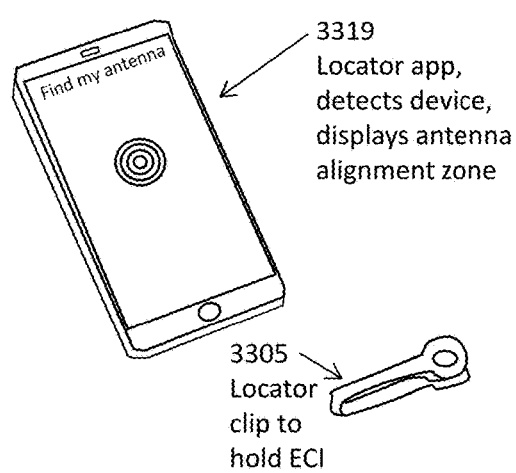
Figure 33C:
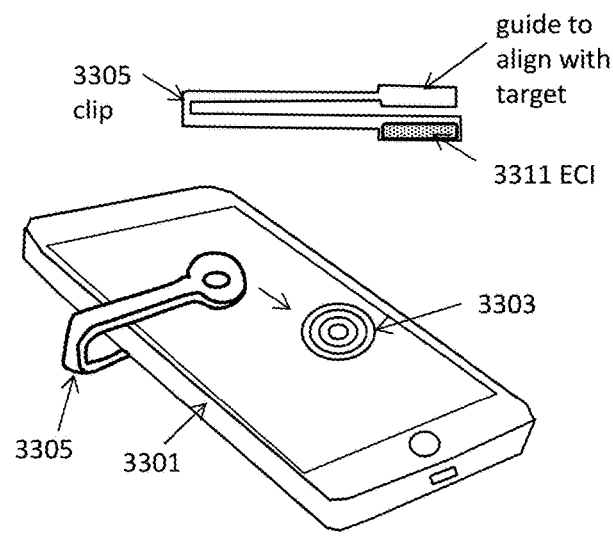

In some variations the application software on the mobile device (e.g., phone) may also provide guidance for alignment of the ECI, including indicating on the screen where to place the ECI apparatus and/or appliance and ECI. The software may also indicate by visual, audio, or both when the ECI is in good alignment, allowing the user to correct/adjust the alignment. For example, FIG. 33A illustrates another example of direct communication between the ECI and a smartphone. In this example, the application software for data transfer from the ECI to the phone 3301 indicates by displaying an alignment zone 3303 on the screen of the phone where to position the ECI. In FIGS. 33B-33C, an additional holder or interface 3305 to hold the ECI securely on the phone is shown, and FIG. 33C illustrates the use of the holder 3305 to hold the ECI on the optimal target for transfer of data. In this example, the data receiver is a mobile/handheld device (e.g., smartphone) that may help align the ECI for transfer of the data, as illustrated in FIGS. 33B and 33C. In these illustrations, the screen of the mobile device shows a target that may indicate the position for placement of the ECI relative to the mobile device for best communication between the ECI (e.g., an antenna such as a NFC antenna) in the ECI and an antenna in the smartphone (such as an NFC antenna). In this example, the target (which is drawn as a bullseye, but may be any marker or indicator 3303) is shown on the screen and the user may manually align the target-matching portion of the 'clip' 3305 for positioning opposite of the target 3303. This allows an ECI attached or on the clip (see top of FIG. 33C) to be held optimal alignment. The mobile device may determine the location of the target 3303 based on one or more criterion, including the hardware (e.g., mobile device) configuration, model, etc., such as the known location of the antenna within the device of a particular make and model that may be determined by the application method (e.g., software) operating the mobile device (shown in FIGS. 33B and 33C as a "Find my Antenna" application method). In some variations, the application method may calculate the target 3303 position based on feedback between the receiver (mobile device) antenna and the ECI device.

Other alignment mechanisms and techniques may also be used to align and/or hold the ECI apparatus in communication with the phone for wireless transfer of data from the ECI to the smartphone. For example, in some variations a magnetic force may be used to attract the ECI to a target location. Other mechanical alignment mechanisms may be used to secure the ECI apparatus in alignment with the antenna region of the phone. For example, a phone case or cover (e.g., sleeve) may be used that includes a depression/holding region for aligning the ECI with the antenna of the phone. In some variations the mount/cover/sleeve may include one or more pins to hold the ECI device in position.

Figure 41:
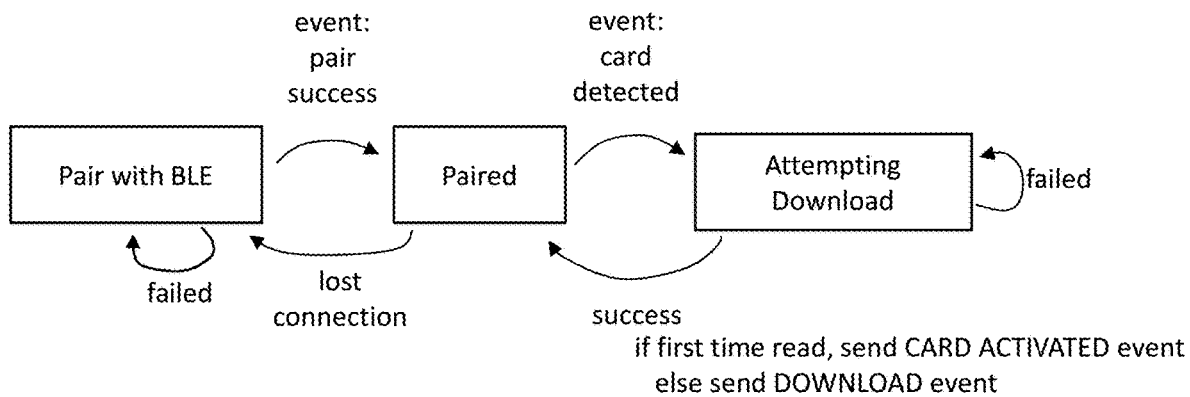
FIG. 41 is a flow diagram of a communications protocol that may be part of an application program.
Figure 43:
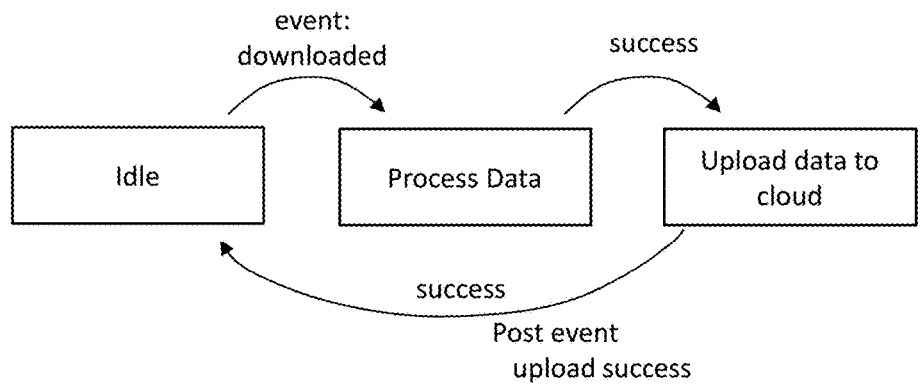
FIG. 43 is a flow diagram for data processing using an application program processing EIC data.
Figure 44:
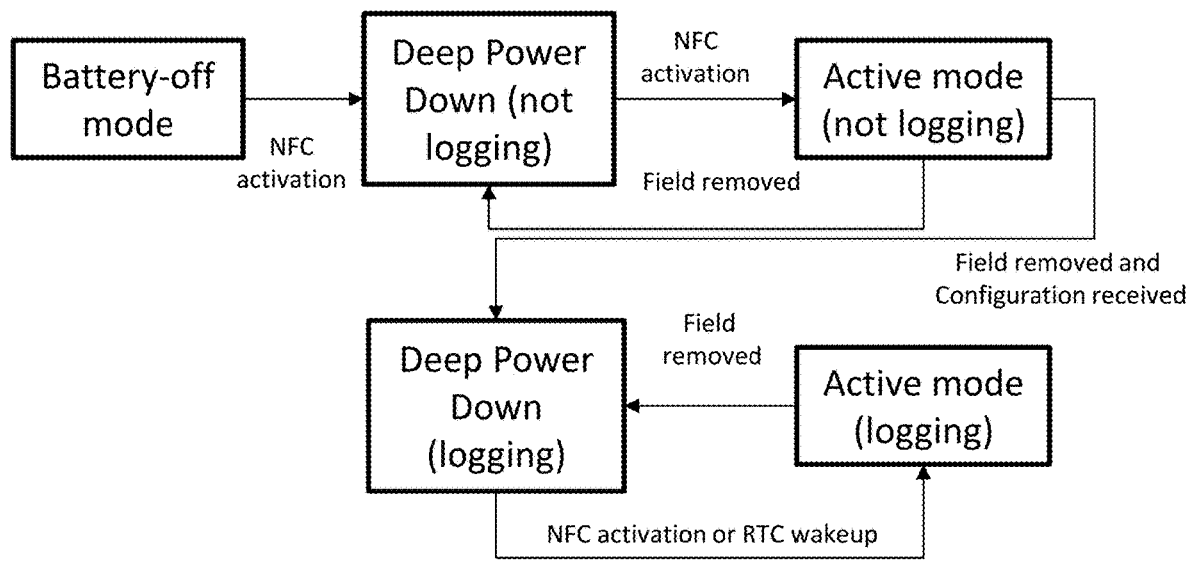
FIG. 44 is a flow diagram schematically illustrating operational states of an ECI device.
Figure 45:
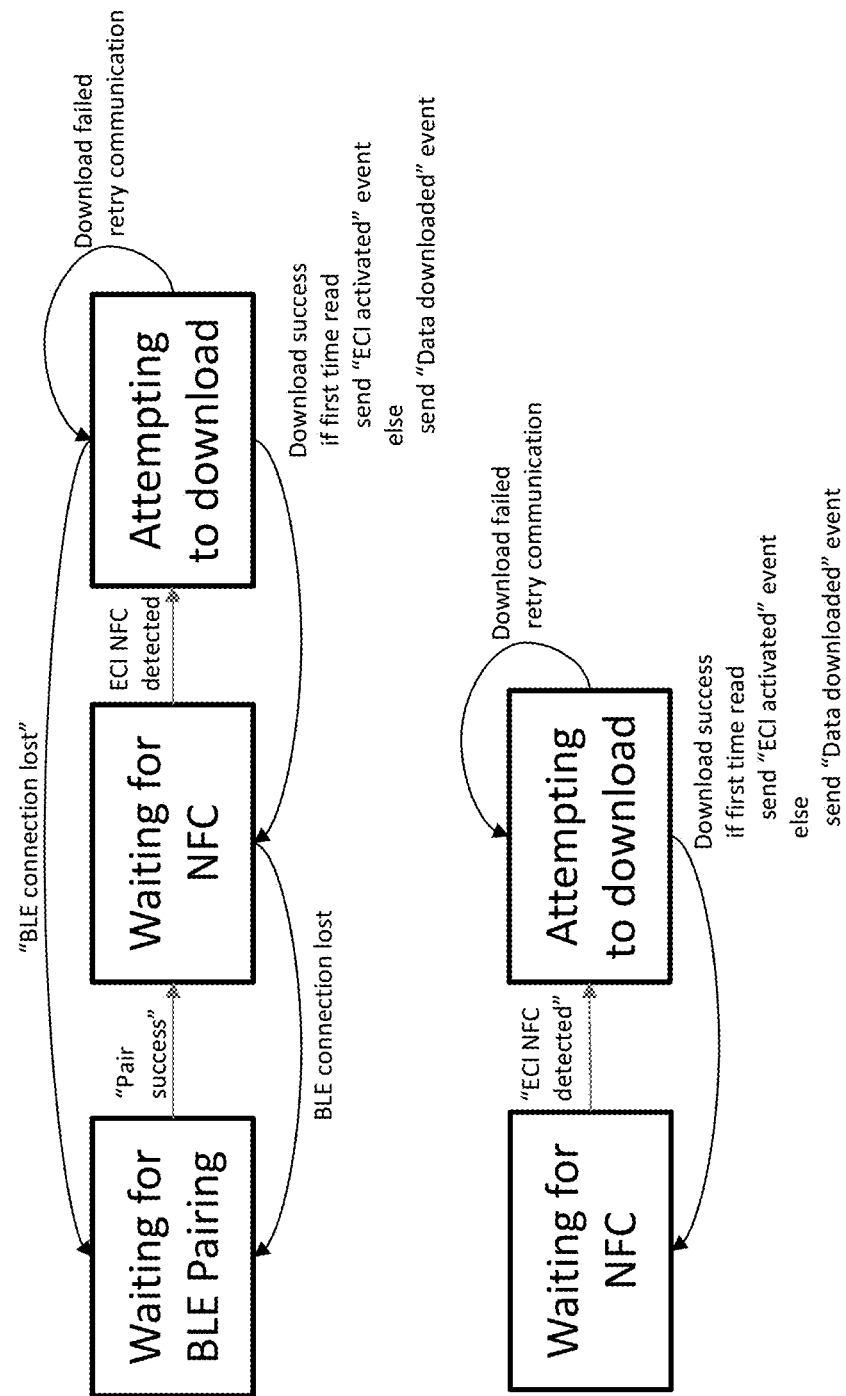
FIG. 45 is a flow chart illustrating the control of communications by a receiving processor (e.g., smartphone) communicating with an ECI device.
Figure 46:
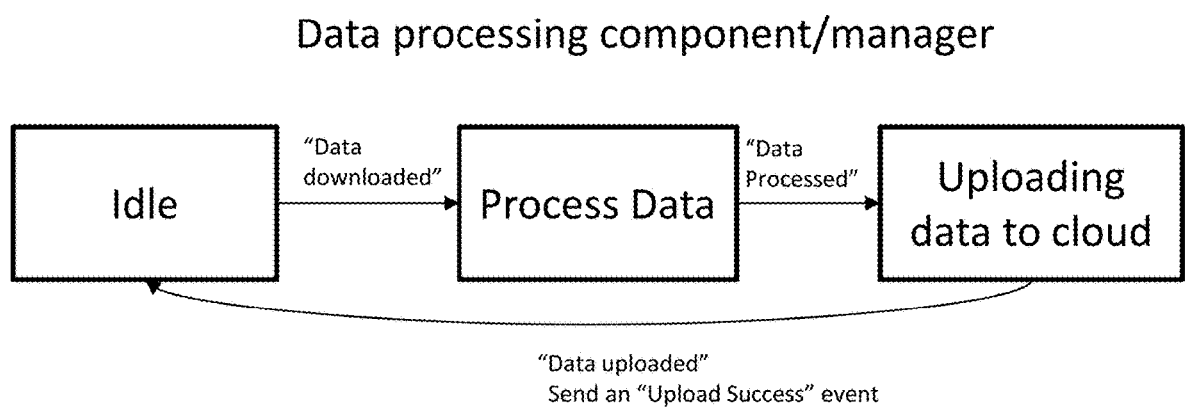
FIG. 46 is an example of a process chart for a data processing component/manager.
Figure 47:
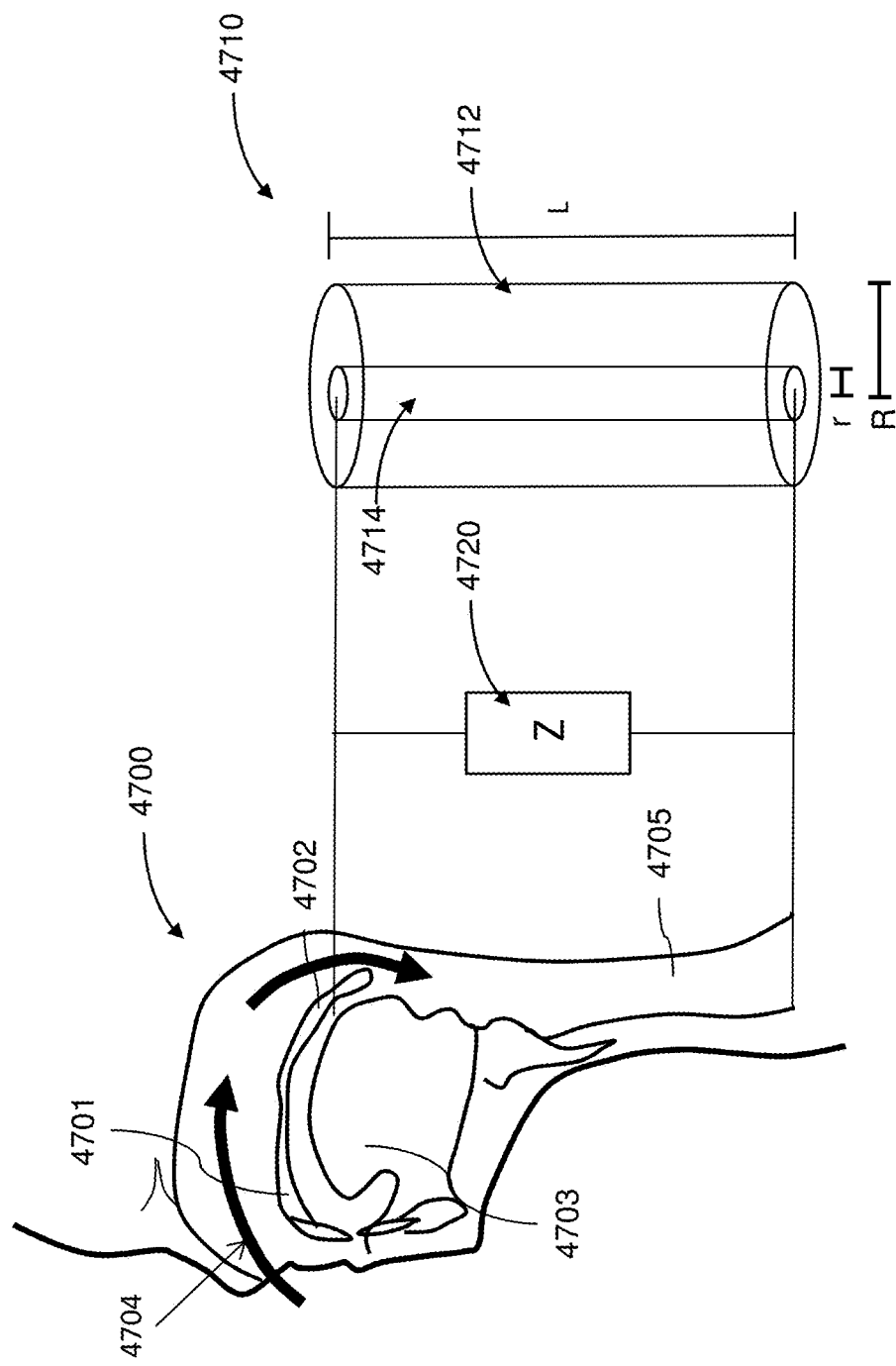
FIG. 47 illustrates an impedance model of a patient's airway.

As mentioned above, any of the apparatuses described herein (including systems) may communicate with a handheld electronics device such a smartphone via control software running on the smartphone (or other hand-held electronics). This application software may interface with the electronic compliance indicator and may enhance wireless communications between the electronic compliance indicator (ECI) using NFC and BLE protocols. The application can complement or supplement the ECI by incorporating mechanisms for encouraging compliance (e.g., incentives, gamification, etc.), and may also provide data processing, visualization, and/or sharing of the data from the ECI. An ECI apparatus may generally record sensor data from patients wearing an orthodontic appliance such as an aligner. The data may be stored in physical memory on the ECI and retrieved by another device, e.g., using NFC and BLE technologies as described above (or NFC and NFC), so that the smartphone may retrieve the data. The smartphone application (app) may consist of several components, some of which are described in FIGS. 41, 42 and 43. For example, in FIG. 41 schematically illustrates an NFC/BLE communication control. In addition, FIGS. 44, 45 and 46 schematically illustrate operational states of the ECI device, as well as control of communication between the device and a remote processor (e.g., smartphone).

Figure 40:
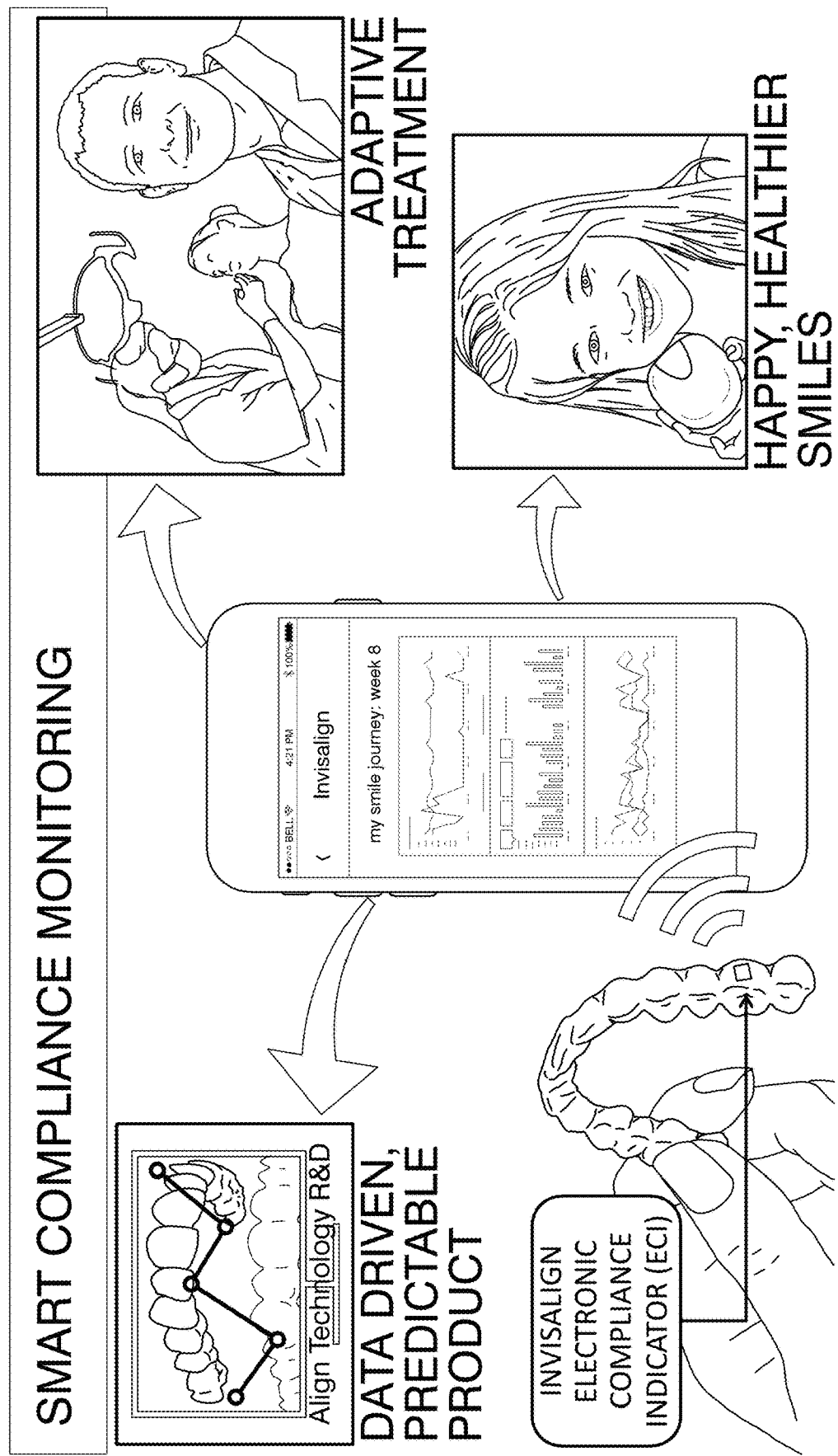
FIG. 40 is an example of a user interface for an application program that may coordinate data transfer and/or analysis and/or compliance monitoring.
Figure 42:
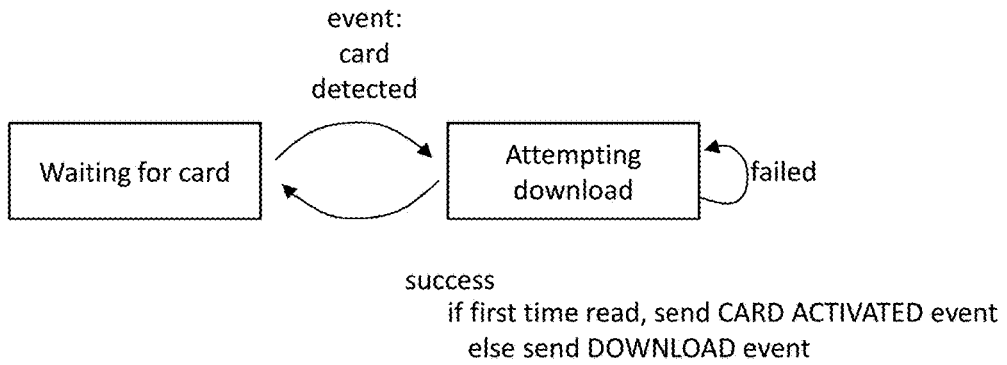
FIG. 42 is a flow diagram for a coordinating near field communication between a smartphone and an ECI apparatus.

Handling wireless communications and data transfer with the ECI may be coordinated by the application software. The application can post events to may include other elements of the application, for example: a home screen or user interface (UI) manager that can respond to an event (e.g., a "CARD ACTIVATED" event, as shown in FIGS. 41-42, when the ECI is first turned on and receives confirmation back) to provide a notification to the user or launch a welcome or instructions screen; and/or a data analysis manager that can respond to data transfer (e.g., an "UPDLOAD SUCCESS" in FIG. 43) events. The application software may generate displays, including graphs, and may look for patterns in the data to improve accuracy/specificity/sensitivity of the compliance data. It may post events such as "LOW COMPLIANCE," "HIGH COMPLIANCE," etc. See, e.g., FIG. 40 (center), showing a user interface for an exemplary application software including a smart compliance monitoring.

Some components of the application software may not exist or run locally (on the smart phone), but could run on a remote server. For example, data history and data analysis can be hosted on a remote server. In this case, the app may also have a component to upload and download data to and from this server.

The application software may help the user to manage the operation of the appliance and/or the ECI on the appliance, including starting/stopping timing/sensing/recording, and/or transferring data to/from the ECI, activating/de-activating the ECI, etc. Events that are posted from normal use can be used to complement or supplement the ECI system from the application software. For example, the application software may manage notifications or reminders related to the appliance and/or ECI and/or can respond to an event (e.g., a "CARD ACTIVATED" event) by initiating a timer, which can post another event when it expires. One possible response to this event may be to push a notification to the user to remind the user to connect the ECI device to the phone. This notification can be an alarm, email, text message, etc. This service could also respond to a "LOW COMPLIANCE" by notifying other connected users (e.g., parents or doctors).

The application software may also coordinate an incentives system which responds to specific events related to wearing/using the orthodontic appliances described herein. For example, and application software may include or operate a game with virtual rewards (e.g., coins, trophies, RPG elements "level up"/upgrade your smile, points, etc.), monetary rewards (e.g., discounts, coupons, gift cards, etc.), and/or motivational messages. For example when the "CARD ACTIVATED" event occurs by outputting→"You've activated your first aligner! You're on your way to a happy healthy smile." After a DOWNLOADED event, a specific message may be displayed or transmitted to the user depending on the data, e.g., "great job wearing your aligners this week," "just 2 more aligners to go!" or the like.

FIG. 42 illustrates a potential flow diagram for an application software as described herein for controlling NFC, including detecting the ECI. FIG. 43 illustrates a potential control diagram for an application software controlling data processing.

An example of the operational states for an ECI device is shown in FIG. 44, illustrating the interaction of the communication between the device (e.g., an appliance with monitoring sensors, shown as the ECI) and a remote processor such as a smartphone. In FIG. 44, the device transitions between various power down and logging states in which NFC is active or removed. Other possible states may include an active mode in which logging is complete, and active mode with live measurements.

FIG. 45 illustrates the management of communications by the receiving processor, such as a smartphone, on which control logic (e.g., software) is operating; FIG. 45 illustrates one example of how the phone/receiver app may behave and interact. For example, in FIG. 45, the smartphone may toggle between waiting for BLE pairing, waiting for NFC and attempting to download, or waiting for NFC and attempting to download, depending on the communication status between the smartphone and the orthodontic appliance with the sensor (e.g., ECI). A communications manager (e.g., the software/firmware on the smartphone) can be responsible for managing BLE or NFC only communications. It can post events so that external components or managers can act on them (e.g., a Data Manager can act on a "Data Downloaded" event, and another component, not illustrated here, could act on a "Data Uploaded" event). Similarly, FIG. 46 illustrates an example of a process chart for a data processing component/manager.

The present disclosure provides improved systems, methods, and apparatus for monitoring physiological characteristics of a patient's intraoral cavity and airway. Appliances are provided with sensors configured to send, and receive signals, and a processor records those signals to memory. The signals can be analyzed to determine physiological characteristics of the patient. The intraoral appliance may also be a treatment appliance, treating an underlying condition and monitoring physiological characteristics to track the efficacy of that treatment.

As used herein the term "and/or" is used as a functional word to indicate that two words or expressions are to be taken together or individually. For example, A and/or B encompasses A alone, B alone, and A and B together.

The present disclosure provides orthodontic systems, apparatus, and related methods for monitoring physiological characteristics of a patient, as well as for assessing treatment parameters such as appliance efficacy.

In one aspect, a method for monitoring a physiological characteristic of a patient is provided. The method comprises positioning an intraoral appliance in the patient's intraoral cavity. The intraoral appliance is shaped to receive the patient's teeth and comprises a plurality of electrodes each positioned to make electrical contact with a different part of the patient's intraoral cavity. The method further comprises measuring an electrical impedance using the plurality of electrodes and determining the physiological characteristic based on the electrical impedance. In some embodiments, the measuring and determining steps are performed by one or more processors disposed on or within the intraoral appliance.

In some cases, the physiological characteristic comprises one or more of: airway diameter, airway volume, airway resistance, lung fluid level, soft tissue crowding, breathing rate, muscle activity, ionic composition of saliva, or ionic composition of oral mucosa. The physiological characteristic can be related to a sleep disorder of the patient, and the sleep disorder can comprise one or more of sleep apnea, snoring, or bruxism. In some embodiments, the sleep disorder comprises sleep apnea and the intraoral appliance is configured to treat the sleep apnea.

In some cases, the efficacy of the intraoral appliance in treating the sleep apnea is determined based on the determined physiological characteristic. The one or more processors may be configured to make this determination.

In some cases, the electrical impedance comprises a near-field impedance and the physiological characteristic comprises one or more of soft tissue crowding, ionic composition of saliva, or ionic composition of oral mucosa. In some cases, the electrical impedance comprises a far-field impedance and the physiological characteristic comprises one or more of lung fluid level or airway length.

In another aspect, a method is provided for monitoring a characteristic of a patient's intraoral cavity or airway. The method comprises positioning an intraoral appliance in the patient's intraoral cavity. The intraoral appliance is shaped to receive the patient's teeth and includes a transmitter and a receiver. The method further comprises causing the transmitter to emit a signal within the patient's intraoral cavity, measuring a signal returning from the patient's intraoral cavity or airway in response to the emitted signal using the receiver, and determining the characteristic of the patient's intraoral cavity or airway based on the measured signal. In some embodiments, the measuring and determining steps are performed by one or more processors disposed on or within the intraoral appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

FIG. 1 illustrates an impedance model of a patient's airway 4700. The airway 4700 comprises an intraoral cavity bounded on the maxillary side by the hard palate 101 and soft palate 4702, bounded on the mandibular side by the tongue 4703 and maxilla, and bounded on the lateral sides by the cheeks. As the patient breathes, airflow 4704 passes through the mouth and sinuses and travels down the upper airway 4705 toward the lungs. Obstruction of these passageways can cause sleep apnea, and may be due to conditions such as soft tissue crowding or narrowing of parts of the upper airway, for example. A patient's airway may be modeled as a substantially cylindrical passageway between the intraoral cavity and the lungs. In some embodiments, the patient's trachea is approximated as a cylinder 4710 of length L with an outer shell 4712 of soft tissue and a hollow core 4714 filled with air. The conductivity of soft tissue is much higher than that of air; accordingly, the impedance of the airway can be approximated as the resistance of a hollow cylinder with outer radius R (the radius of the tissue surrounding the airway in the neck), inner radius r (the airway radius), and length L (the airway length). The resistivity p can be approximated as that of the airway tissue, and the impedance 4720 can be estimated by the equation $Z=\rho L/A$, where A is the total conductive area—in this case the outer cylinder area minus the inner (substantially non-conductive) cylinder area. This gives a total impedance 4720 of about $Z=\rho L/\pi(R^2-r^2)$. More generally, in some embodiments the impedance will be proportional to the resistivity of soft tissue and the length of the airway, while being inversely proportional to the cross-sectional area of the conductive tissue of the airway. For electrical signals traveling between the intraoral cavity and the lower airway, the upper airway may thus be treated as a circuit element characterized by an impedance Z similar to this equation. The impedance Z depends on the inner radius r—in particular, as r increases, Z increases, and as r decreases, Z decreases. Thus, by measuring the variation of impedance over time, it is possible to determine changes in airway width from corresponding changes in impedance.

Figure 48A:
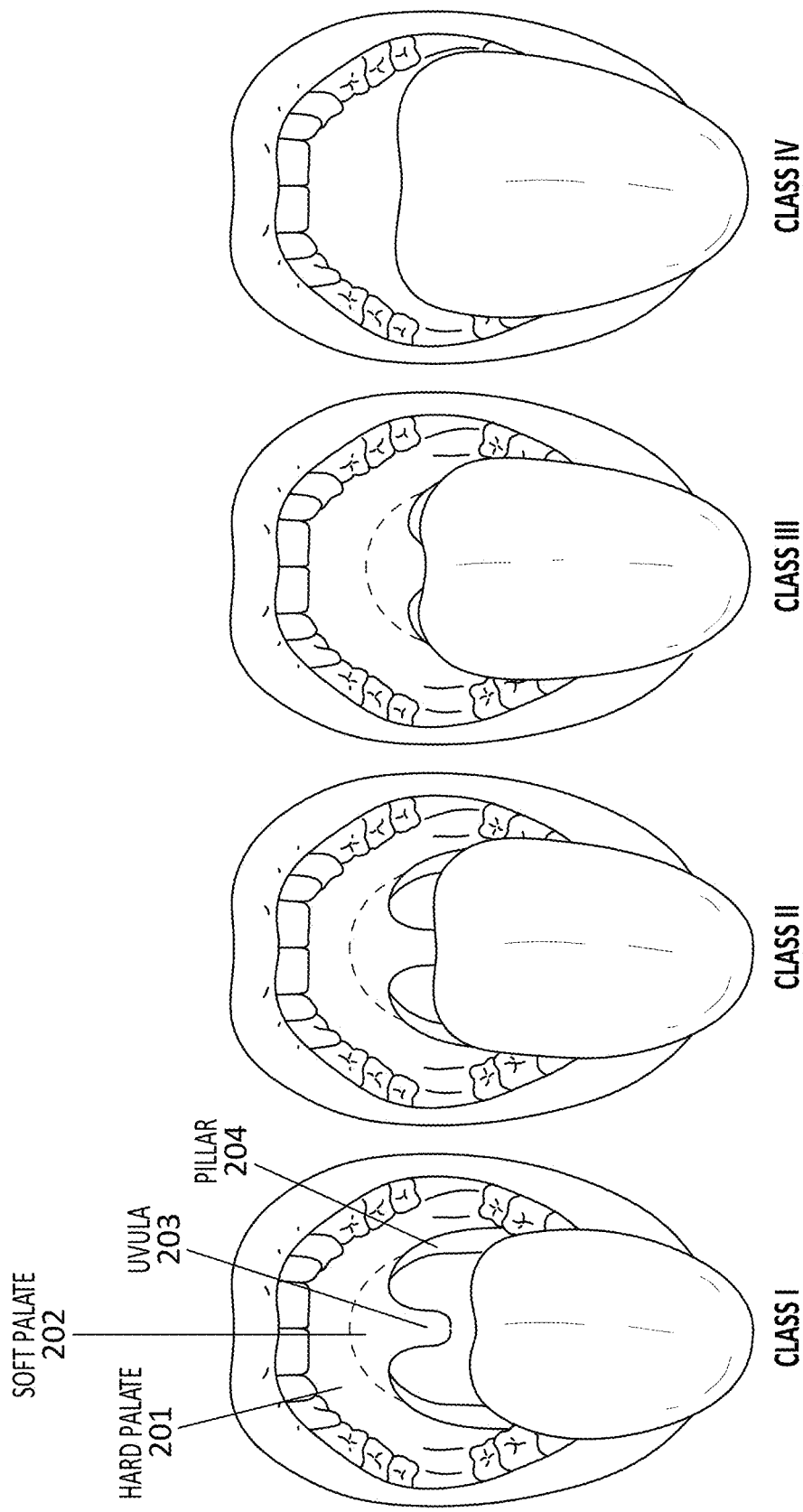
FIG. 48A illustrates the variation of patient airway width for different Mallampati scores.

Variation of airway width can be particularly important in patients with sleep apnea and related disorders, as sleep disturbance and snoring can result from an insufficiently wide airway. FIG. 48A illustrates the variation of patient airway width for different Mallampati scores. A patient with a Mallampati score of I has a large, unobstructed airway with hard palate 201, soft palate 202, uvula 203, and pillars 204 visible; a patient with a Mallampati score of II has a smaller airway with pillars no longer visible; a patient with a Mallampati score of III has only the hard and soft palate and base of the uvula visible; and a patient with a Mallampati score of IV has only the hard palate visible. Higher Mallampati score may be associated with greater likelihood of sleep apnea, with class III and class IV especially likely to exhibit sleep apnea.

Figure 48B:
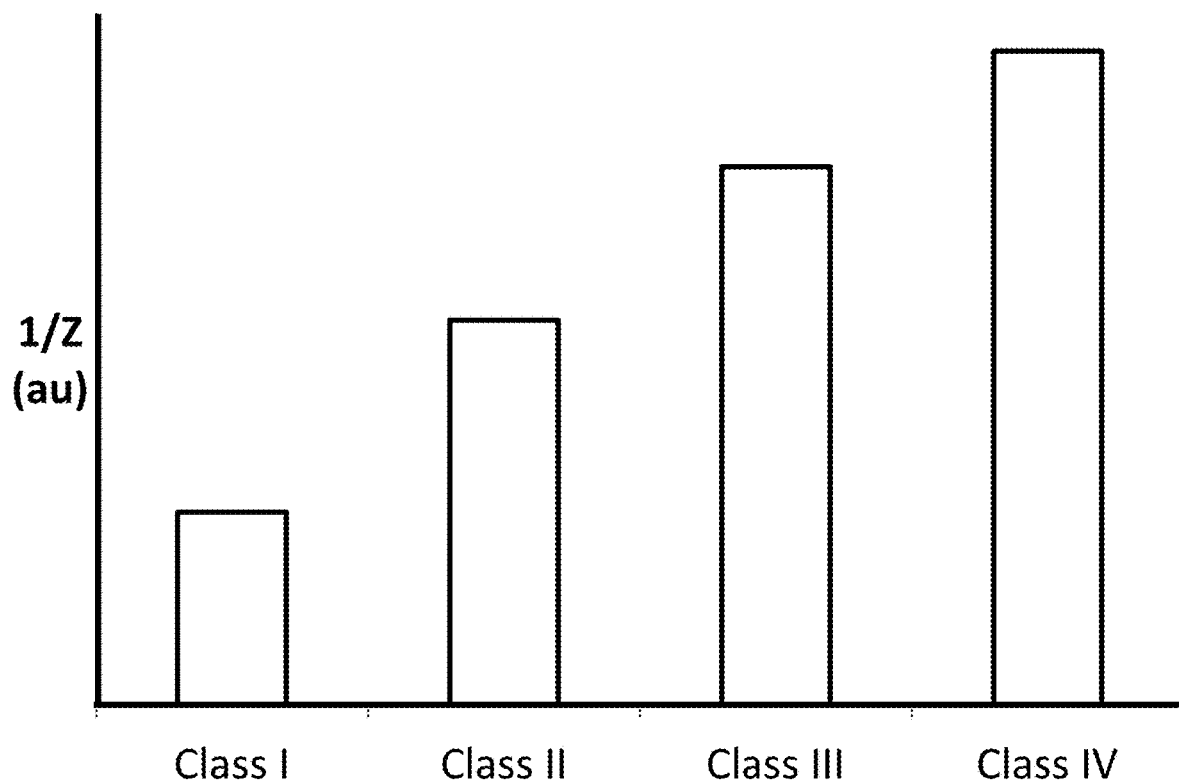
FIG. 48B illustrates the corresponding variation of airway resistance as a function of Mallampati score.

As can be seen from FIG. 48A, in some embodiments, the unobstructed cross-sectional area of the patient's airway decreases with increasing Mallampati score, such that a higher Mallampati score is associated with smaller airway area. As discussed with respect to FIG. 1, smaller airway cross section may correspond to lower electrical impedance. FIG. 48B illustrates the correlation between Mallampati score and airway impedance, plotting Mallampati score against inverse impedance 1/Z. Because increasing 1/Z corresponds to increasing Mallampati score, a measurement of electrical impedance along the airway can be used to determine Mallampati score. An appliance capable of measuring impedance in continuously or continually when worn by a patient allows for continuous monitoring of airway width, for example while a patient is sleeping. Data generated by such measurements can be used in the diagnosis and treatment of sleep apnea.

In some embodiments, the present disclosure provides systems, methods, and devices for measuring characteristics of the patient's intraoral cavity and/or airway based on electrical impedance. Examples of characteristics that may be measured include airway diameter, airway volume, airway resistance, lung fluid level, soft tissue crowding, breathing rate, muscle activity, the ionic composition of saliva, or the ionic composition of oral mucosa. Measurements can be made based on near field impedance, far field impedance, or combinations thereof. As used herein, near field may refer to measurements of impedance along or around the shortest path between two electrodes. For electrodes within the mouth, for example, a near field impedance may be that portion of the impedance that depends on the resistivity and shape of the tissues of the mouth, or a portion thereof. Near field may be used to measure characteristics such as muscle activity, the ionic composition of saliva, or the ionic composition of oral mucosa, for example. As used herein far field may refer to impedance measurements depending on the characteristics away from the shortest path between two electrodes. For electrodes within the mouth, for example, a far field impedance measurement may measure the effects on impedance due to changes in shape or resistivity of tissues in the upper or lower airway, or in the lungs. Far field may be used to measure characteristics such as airway diameter, airway volume, airway resistance, lung fluid level, soft tissue crowding, breathing rate, for example. Impedance may be measured between two or more points in the patient's intraoral cavity. The location of the measurement points in the intraoral cavity may be varied as desired. For example electrodes may be placed on opposite sides of mouth, at points on the upper and lower jaws, at points on the same jaw (upper or lower), or contacting tissues such as cheeks, palate, gingiva, teeth. The electrodes may be configured to contact points in the mouth at a separation of about 1 mm, 2 mm, 4 mm, 10 mm, 20 mm 40 mm, 100 mm, or 200 mm, for example. Shorter separations may be more sensitive to near-field measurements, while longer separations may be more sensitive to far-field measurements, for example.

Figure 49A:
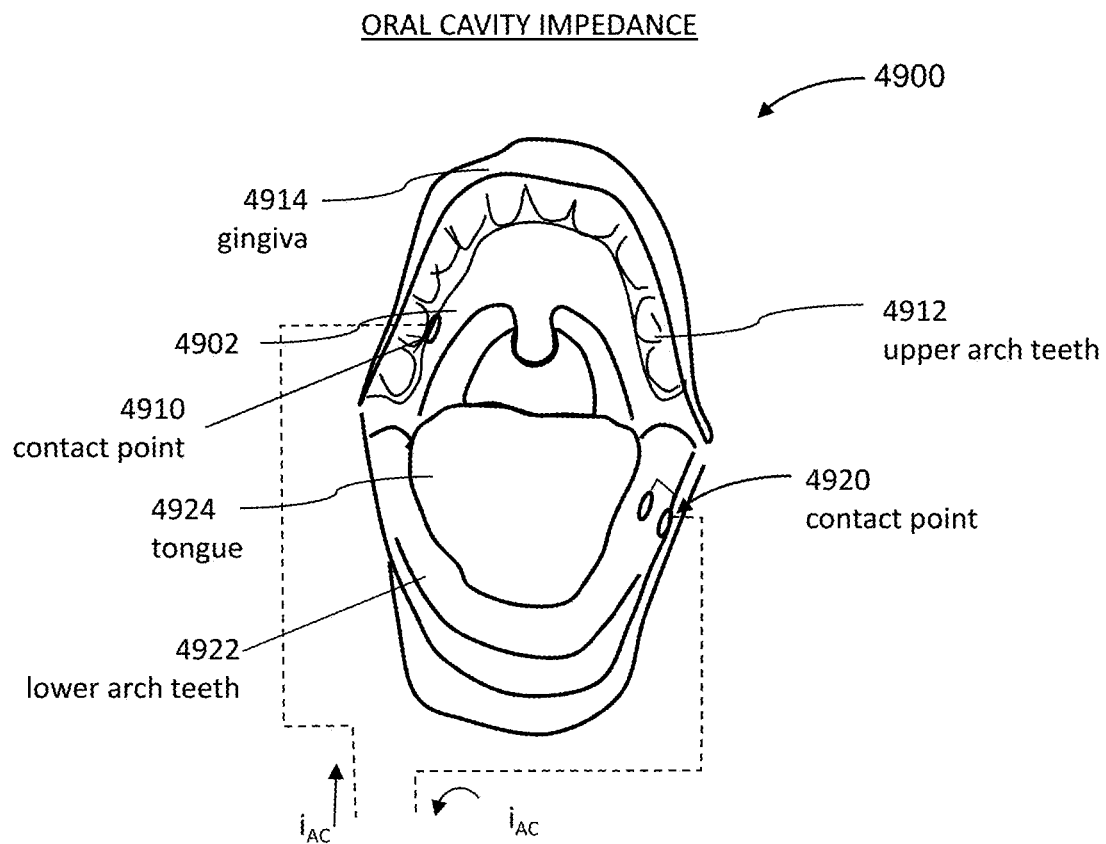
FIG. 49A illustrates a patient's intraoral cavity in conjunction with points from which sensors such as electrodes can be placed to measure characteristics of the intraoral cavity and airway.

FIG. 49A illustrates a patient's intraoral cavity 4900 in conjunction with points from which sensors such as electrodes can be placed to measure characteristics of the intraoral cavity and airway. A pair of contact points 4910 and 4920 are located in the intraoral cavity 4900. One contact point is located along the gingiva of the upper arch 4912, on the lingual side. Although illustrated on the right lingual side near the back of the mouth in FIG. 49A, the location of contact point 4910 may be varied; for example, in some embodiments contact point 4910 is on the buccal side of the upper arch, or on the left side of the mouth, or at any point along the upper or lower arch, including optionally on the same arch as contact point 4920. Contact point 4910 may also be at a point along a cheek of the patient. Similarly, although contact point 4920 is illustrated along the gingiva of the lower arch 4922, on the buccal side opposite the tongue 4924, the contact point 4920 may also be varied in the same manner as contact point 4910, such that any valid contact point for one may be the contact point for the other, including without limitation contact points on the lingual and/or buccal sides of one or more arches, along the hard palate, along the cheek of the patient, or at any other point within the mouth. The position of each contact point pair affects the sensitivities of measurements performed with that pair of points.

For example, referring to the specific choice of contact points illustrated in FIG. 49A, because the airway of the patient stretches away from the intraoral cavity, the airway passageway may be substantially in the far field with respect to electrical impedance. Accordingly, in some embodiments, it is preferred to keep near field signal as small as reasonably possible so as to maximize the relative size of far-field signal. Thus, in some embodiments points 4910 and 4920 are preferably located far apart in the intraoral cavity, as well as near the back of the mouth; in FIG. 49A, this is illustrated with point 4910 located near the upper molars on one side of the mouth while point 4920 is located near the lower molars on the other side of the mouth.

Electrical currents can be induced to flow between contact points, such as points 4910 and 4920 by applying an appropriate voltage, and these currents can be measured to determine electrical impedance. The voltage may be an alternating voltage to induce an alternating current, for example. Current pulses comprising many frequencies may be induced to allow the measurement of impedance at each of multiple different frequencies simultaneously and/or sequentially. In some embodiments, although a portion of the electrical impedance between contact points such as points 4910 and 4920 is due to near field impedance, a portion may also be due to far field impedance, including airway impedance. Contact points that are farther apart may tend to be more sensitive to the far field relative to the near field, while points that are closer together may be more sensitive to the near field relative to the far field. This principle may also be applied for measurements performed with sensors other than electrodes, such as transmitter-receiver pairs as disclosed herein: close-by transmitter-receiver pairs may be more sensitive to the near field while separated transmitter-receiver pairs may be more sensitive to the far field.

Measurements such as impedance measurements can be filtered to isolate that portion of the measured quantity and variation thereof that is due to the variable to be measured and variation thereof. For example, current pulses may be induced and thereafter received by applying a voltage pulse between points 4910 and 4920, then later measuring a return signal. The signal may be tracked as a function of time. The time it takes for a pulse to travel to the lungs and back can correspond to the round trip distance divided by the speed of electrical current, which can be a significant fraction of the speed of light. With sufficient time resolution, such as nanosecond resolution, it is possible to determine how far a pulse has traveled based on its round trip time; by measuring signal strength at the delay time corresponding to a round trip through the airway, a direct measurement of the far field impedance of the airway can be obtained. In some cases, the relative phase of current pulses may be measured to determine the far field impedance, as phase can be affected by time delay.

A portion of the near-field impedance will also depend on the airway width, as the available paths between points 4910 and 4920 along the surface of the intraoral cavity include paths that travel near the airway opening. If the airway opening is smaller, shorter paths are available, which lowers impedance in the near field. Impedance can also be measured repeatedly over longer time periods to allow better filtering of noise sources and isolation of the effect of airway width variation on impedance. For example, as a patient breathes the airway changes shape, so variations in airway impedance correlated with patient respiration can be used to isolate impedance variation caused by airway width variation. Similarly, for other measurements, changes in impedance or other measured properties can be correlated to that particular measurement; for example, changes in ionic saliva content can be determined from near field impedance changes, and physical properties of a tooth or tooth-PDL system can be determined from measured acceleration in response to forces applied by an actuator. It will be appreciated that points 4910 and 4920 may be varied throughout the intraoral cavity to change the measurement sensitivity and specificity; for example, to determine appropriate positions for measurement sensor location, a plurality of point pairs can be tested in the mouth of a patient, and the point pair with highest signal-to-noise ratio for that measurement can be selected for use in that patient or other patients. Other measurements, such as transmitter-receiver measurements, may follow the same pattern for their respective measurement variables and can likewise be placed at variable positions throughout the intraoral cavity to change their sensitivities and specificities for their respective measurements.

Figure 49B:
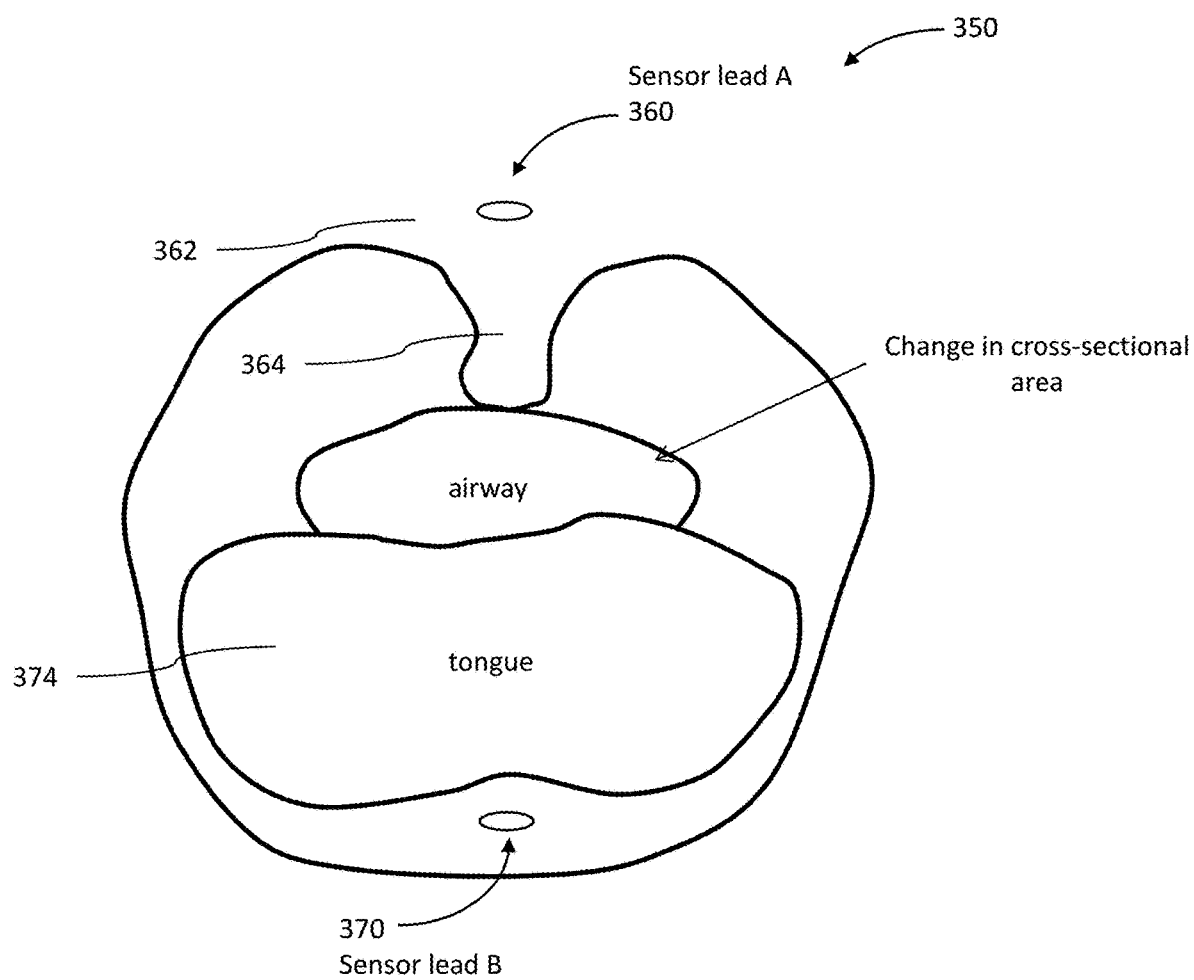
FIG. 49B illustrates alternative positions in which sensors such as electrodes can be placed to measure characteristics of the intraoral cavity and airway.

FIG. 49B illustrates alternative positions in which sensors such as electrodes can be placed to measure characteristics of the intraoral cavity and airway. In sensor configuration 350, a first sensor 360 is located along the maxillary palate near the soft tissue 362 and uvula 364. A second sensor is located along the mandibular palate between the tongue 374 and the mandibular teeth (not shown). In this embodiment, the sensors are located on opposite sides of the airway, such that the airway lies along the shortest path between the two sensors. In the case that sensors 360 and 370 are electrodes, for example, the impedance between the two sensors will depend in part on the width of the airway, with lower impedance corresponding to a narrower (and thus more occluded) airway.

In some embodiments, the impedance measurements described herein are performed using electrical sensors coupled to an oral appliance. Examples of such oral appliances include dental retainers, aligners, and mouthguards. In some embodiments, the oral appliance is used to treat sleep apnea, such as a mandibular advancement device. In some embodiments, a mandibular advancement device is worn by the patient in the order to displace the lower jaw anteriorly relative to the upper jaw to treat sleep apnea. The mandibular advancement device can be a patient-removable appliance (e.g., the patient can place and remove the appliance without aid from a practitioner) that is inserted into the patient's mouth prior to sleep so as to maintain the lower jaw in an advanced position during sleep, and is removed from the patient's mouth while the patient is awake to allow for normal activity. In alternative embodiments, the intraoral appliance can include one or more components that are not patient-removable (e.g., attachments or brackets affixed to one or more teeth, anchoring devices positioned in the tissue of the intraoral cavity such as bone). In some embodiments, the intraoral appliance includes at least one appliance shell having a plurality of cavities shaped to receive teeth of a single jaw of the patient.

Any number of sensors can be used, such as electrodes, acoustic transducers, and accelerometers. The sensors can be located in any portion of the appliance, such as adjoining the lingual or buccal sides of the gingiva, adjoining the dental surfaces of teeth, adjoining the cheeks, or along the roof or bottom of the mouth. The sensors can be coupled to the appliance in various ways, such as by adhesives, fasteners, embedding within the appliance material, or insertion into cavities formed in the appliance. The measurements described herein may be obtained using sensors coupled to a single appliance worn on the patient's upper or lower jaw. Alternatively, sensors may be distributed between a pair of appliances worn on the upper and lower jaws, respectively. In some embodiments, the oral appliance(s) and sensors are contained entirely within the patient's intraoral cavity when worn. For example, in some embodiments the appliances can be operated without connection to external power sources, control electronics, or external sensor points. The appliance electronics can comprise a power source such as a battery to store energy for continuous operation. The battery can be rechargeable, for example, by plugging the appliance into a recharger when not in use or by recharging using wireless power transfer—in the latter case the appliance can comprise appropriate antenna(s) to receive transmitted power from a base station. The oral appliance(s) and sensors may be patient-removable, allowing for measurements to be performed without the need for sensor apparatus being implanted within patient tissue or affixed to the mouth or teeth of the patient.

FIGS. 50A-50G illustrate a variety of oral appliances comprising electrical sensors such as electrodes positioned in various configurations to allow measurement of impedance due to airway width variation, as well as other physiological characteristics of a patient, including characteristics of a patient's intraoral cavity or airway. Electrodes can be used to monitor resistance changes within the oral cavity, as in patients with abnormal soft tissue crowding, the conductive paths between electrodes may be shorter. Because stretching of soft tissue during changes in mandibular position can alter the conductive pathways within the intraoral cavity, impedance measurements can be used to detect whether the patient has an open or closed mouth, for example, or whether the mandible is retruded or protruded. While well-separated electrodes may be desirable for increased sensitivity to far-field impedance variation in some embodiments, closely-positioned electrodes can also be used for monitoring of physiological characteristics of the patient. For example, the electrical potential generated by muscle cells during activation may be monitored by appropriately-positioned electrodes. Among the physiological activities that may be detected by monitoring muscle movements in this way are temporomandibular joint articulation, increased masseter activity during parafunctional activity (such as grinding or clenching), and upper airway relaxation due, for example, to upper airway collapse or decrease in activity, which are associated with hypopnea or apnea.

Although electrodes are used herein as exemplary sensors in the illustrated orthodontic appliances, sensors other than electrodes may be used for sensing physiological properties of a patient's intraoral cavity and/or airway, by measuring properties other than impedance, such as piezoelectric pulses, acoustic waves, and acceleration. In some embodiments, the physiological properties can be measured by transmitting a signal into the patient's intraoral cavity and/or airway, and measuring the response signal returning from the intraoral cavity and/or airway. The characteristics of the response signal (e.g., amplitude, frequency, etc.) may vary based on the properties of the patient's intraoral cavity and/or airway.

In such embodiments, the electrodes marked in FIGS. 50A-50G may be replaced with appropriate pairs of sensors, acting as transmitter and receiver respectively. For example, transducers can be used for generating and receiving acoustic waves (e.g., ultrasound), and phase and magnitude information of the response signal can be used to image the oral cavity or upper airway. An actuator (such as a piston, vibration motor, or piezo-electric crystal) and an accelerometer may replace respective electrodes. An impulse signal can be sent to a tooth via the actuator and a response signal can be recorded with an accelerometer in contact with the tooth. This response can be correlated with different phases of tooth movement, such as movement due to orthodontic forces applied by an appliance shell, because the stiffness of the tooth-PDL structure will vary with different stages of tooth movement. The response may also be correlated with tooth, root, and/or PDL health, even if no tooth movement is being induced by the appliance shell. Actuators may also be placed to produce forces that can result in electrical currents (for example, via the piezoelectric effect) in structures of the mouth. For example, compression of bone and collagen results in movement of electrons in the crystal lattice, and application of force on the teeth can result in a short piezoelectric effect on the alveolar bone which may be detected by appropriate receiving sensors such as electrodes. Electrical signals produced by alveolar and periodontal ligaments (PDL) when under load can stimulate changes in bone metabolism—electrical sensors such as electrodes may also be used to detect these electrical signals, for example, by monitoring changes in voltage. These examples of measurements can be combined to perform simultaneous or staggered measurements, including combinations with electrode measurements of impedance and other electrical properties. In some embodiments, multiple measurements are performed and their results compared or combined using sensor fusion techniques, thereby improving resolution of each measured quantity.

Figure 50A:
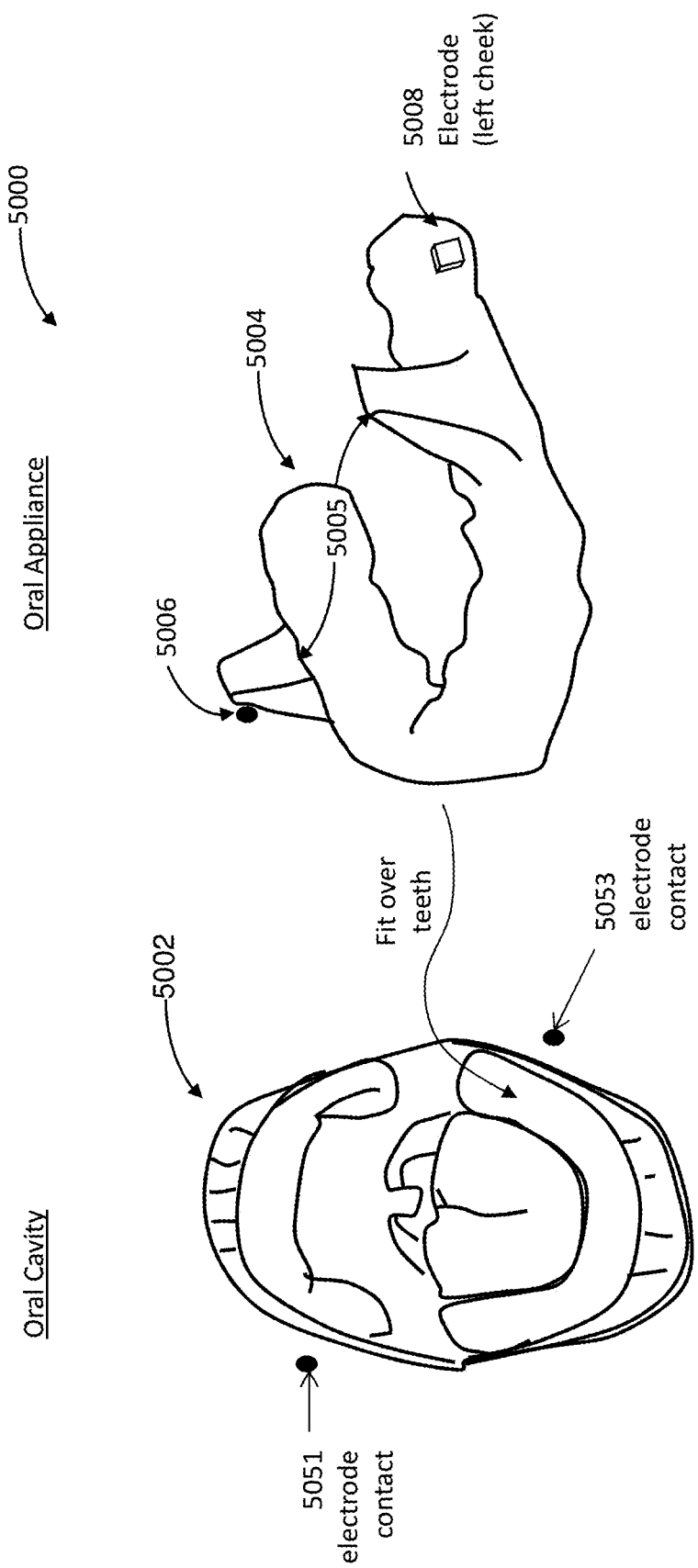
FIG. 50A illustrates an appliance wearable over a patient's teeth comprising sensors positioned at diametrically opposed points in a patient's intraoral cavity.

FIG. 50A illustrates an appliance 5000 wearable over a patient's teeth comprising sensors positioned at diametrically opposed points in a patient's intraoral cavity 5002. The appliance 5000 comprises a shell 5004 with teeth-receiving cavities configured to receive the teeth of a patient when worn in the patient's mouth 5002. The appliance shell comprises protruding portions 405 configured to extend along the cheeks of the patient when the appliance is worn. The protruding portions can be configured to engage protruding portions of an appliance worn on the opposite jaw to provide forces for mandibular advancement, for example. The appliance further comprises a plurality of sensors such as electrodes, with a first electrode 5006 disposed on a protrusion and positioned to come into contact with the right cheek of the patient when worn. The second electrode 5008 is disposed on the shell and positioned to come into contact with the left cheek of the patient when worn. The illustration of the patient's intraoral cavity 5002 shows the points which are contacted by each electrode when the appliance is worn. The electrodes are positioned to contact substantially opposite points near the rear part of the patient's intraoral cavity, providing electrical contact points in areas similar to those illustrated in FIG. 49A. As a result, the electrode positions are well-suited to measure far-field impedance, for example. In alternative embodiments, the appliance 5000 can also be used to perform other types of measurements, as discussed herein.

The appliance 5000 further comprises appropriate wiring disposed within shell 5004, providing electrical contact between sensors, illustrated as electrodes 5006 and 5008 and a processor disposed within the shell. The processor is further connected to a power source such as a battery that provides electrical power. The processor is configured to control voltage values at each electrode to allow the generation of current pulses, alternating current, and/or direct current flow. The circuitry connecting the processor to the electrodes further comprises a current measuring unit, such as an ammeter, so that impedance may be calculated by the processor by a measurement of voltage and current as a function of time. The processor comprises a clock for time measurement, and is connected to memory to allow the recording of sensor data, as well as to contain instructions to be executed by the processor. Optionally, the processor is further connected to a wireless radio transmitter, allowing recorded data to be transmitted to an external receiver for processing by an external computing device. The external receiver may be, for example, a mobile device or WiFi antenna, and the receiver and transmitter may communicate using an appropriate communications protocol such as Bluetooth, cellular, WiFi, or other protocols. FIG. 50C provides more detail of the internal structure of an appliance such as that illustrated in FIG. 50A.

Figure 50B:
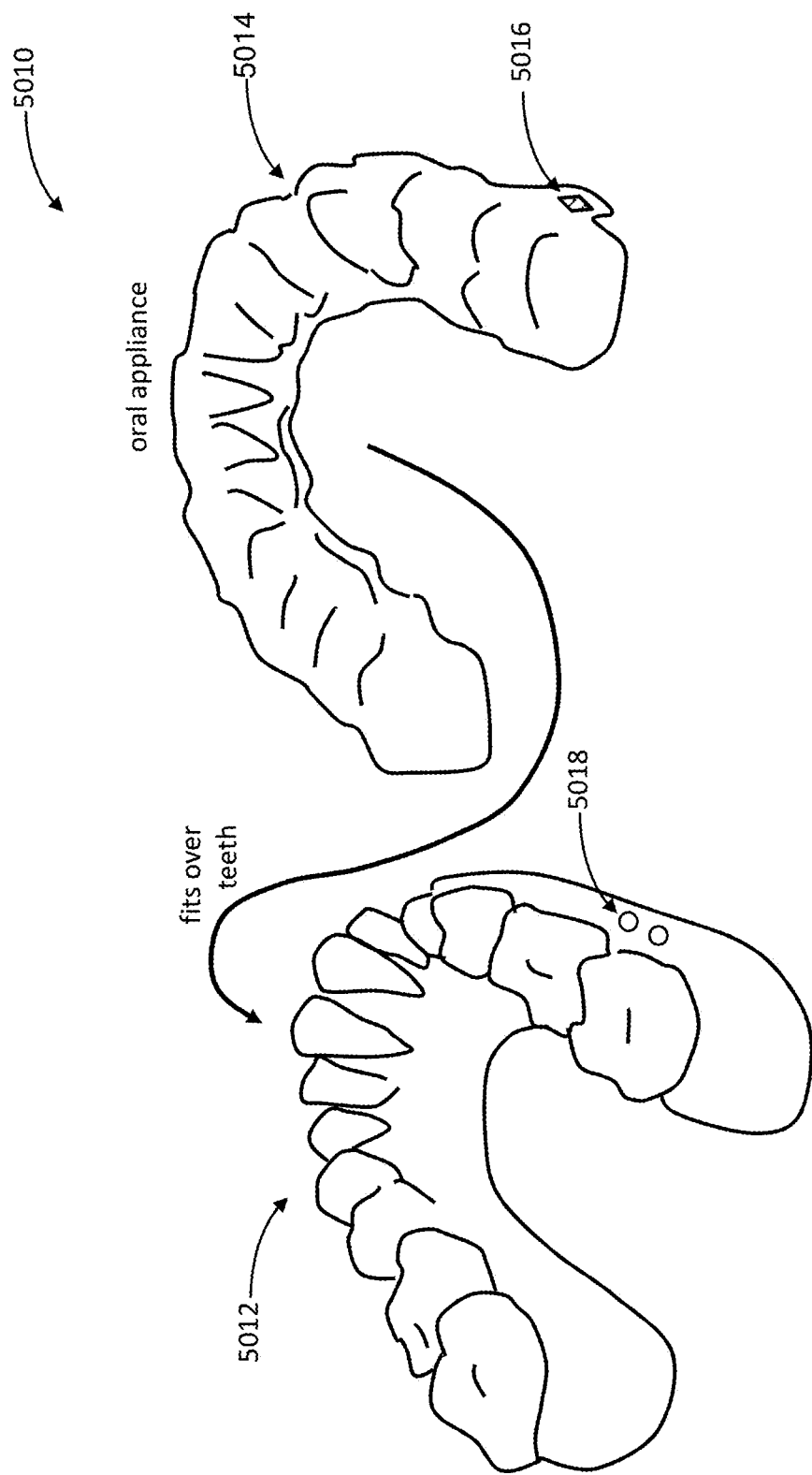
FIG. 50B illustrates an appliance wearable over a patient's teeth comprising sensors positioned in close proximity to each other.
Figure 50C:
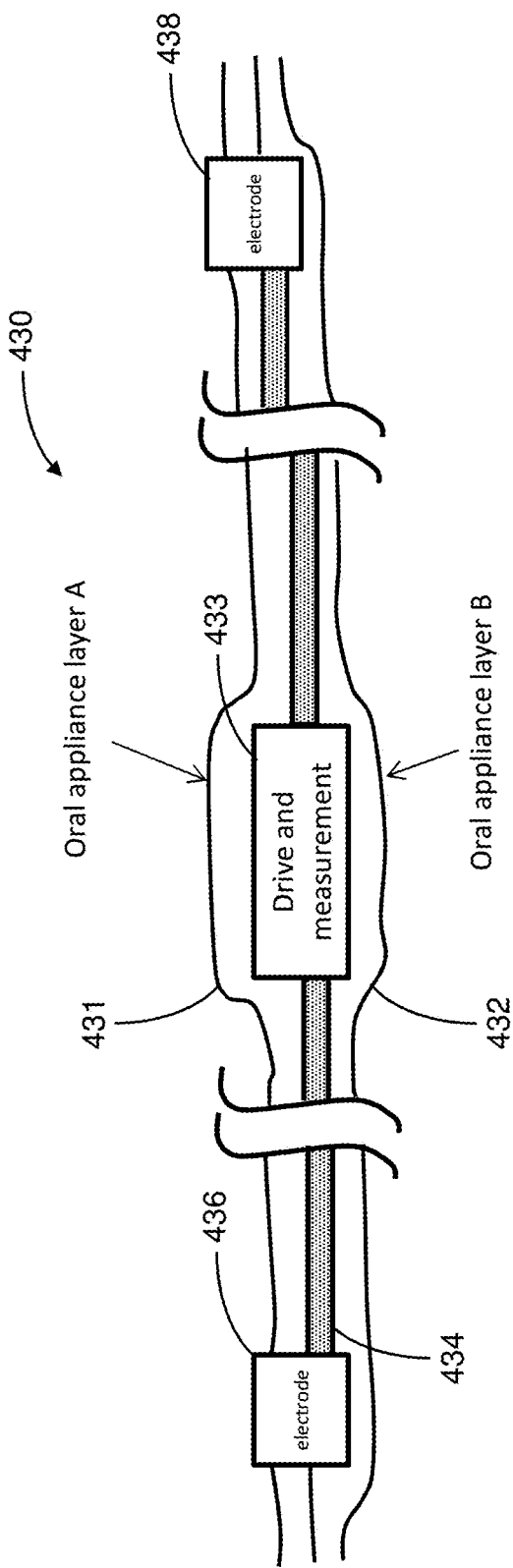
FIG. 50C illustrates an interior of an appliance with an embedded measurement system comprising drive electronics and sensors.

FIG. 50B illustrates an appliance 5010 wearable over a patient's teeth 5012 comprising sensors positioned close proximity to each other. The appliance comprises an appliance shell 5014 and the sensors comprise a plurality of electrodes 5016 in close proximity to each other. Sensors such as electrodes may be in close proximity when, for example, the shortest distance between them is small compared to the width of the airway. Sensors in close proximity may be more sensitive to near-field measurements then more distantly-separated sensors. The electrodes are configured to contact a plurality of nearby points 5018 within the patient's intraoral cavity when the appliance is worn by the patient. In this illustration, the contact points are located on the buccal gingiva; in other embodiments, the contact points may be on the cheeks or lips, or on the lingual side touching the tongue and lingual gingiva. The contact points may also touch the teeth on the lingual and/or buccal side (including one sensor on each side of a tooth). The nearby electrodes are sensitive to near-field variations in impedance; accordingly, they may be used to measure properties such as intraoral impedance caused by changes in saliva quantity or contents. For example, if a patient's mouth becomes more dry, the amount of saliva between electrodes 5016 and around points 5018 will diminish, which can increase the impedance as saliva is not available to carry electrical current. Similarly, changes in contents of saliva, such as pH shifts, can be measured, for example, by their resultant changes in saliva conductivity. These properties may also be measured in combination with far field measurements by providing an appliance with both near-field and far-field electrode configurations, such as by adding near-field electrodes such as illustrated in FIG. 50B to an appliance with far-field electrodes such as FIG. 50A. The respective electrode pairs can be separately connected to and controlled by the processor, or may be controlled by separate processors.

FIG. 50C illustrates an interior of an appliance 430 with an embedded measurement system comprising control electronics and sensors. The appliance 430 comprises oral appliance layers 431 and 432, which surround control electronics 433. Control electronics 433 include a power source such as a battery, drive electronics to generate electrical voltage pulses for inducing electrical current, and measurement electronics for measuring electrical current and voltage as a function of time, then recording the resulting data to memory. The control electronics 433 comprise a processor and memory, the memory containing instructions that, when executed, cause the processor to control the drive and measurement electronics to produce electrical pulses and perform measurements such as impedance measurements, according to the methods as disclosed herein. The control electronics are electrically coupled with wires 434 to one or more sensors such as electrodes 436 and 438. The wires 434 are preferably disposed within the layers of the appliance shell, but may include open connections between shells (see FIG. 50E, for example). The electrodes are disposed to contact the surfaces of the patient's intraoral cavity when the appliance is worn. The electrodes perform both current generation and electrical measurement, under the direction of the control electronics. The basic schematic layout shown in FIG. 50C may be used, with appropriate variations in positions of electrodes, driver electronics, and measurement electronics, in any of a variety of appliance shell configurations, including configurations as shown in FIGS. 50A, 50B, and 50D-50G.

Figure 50D:
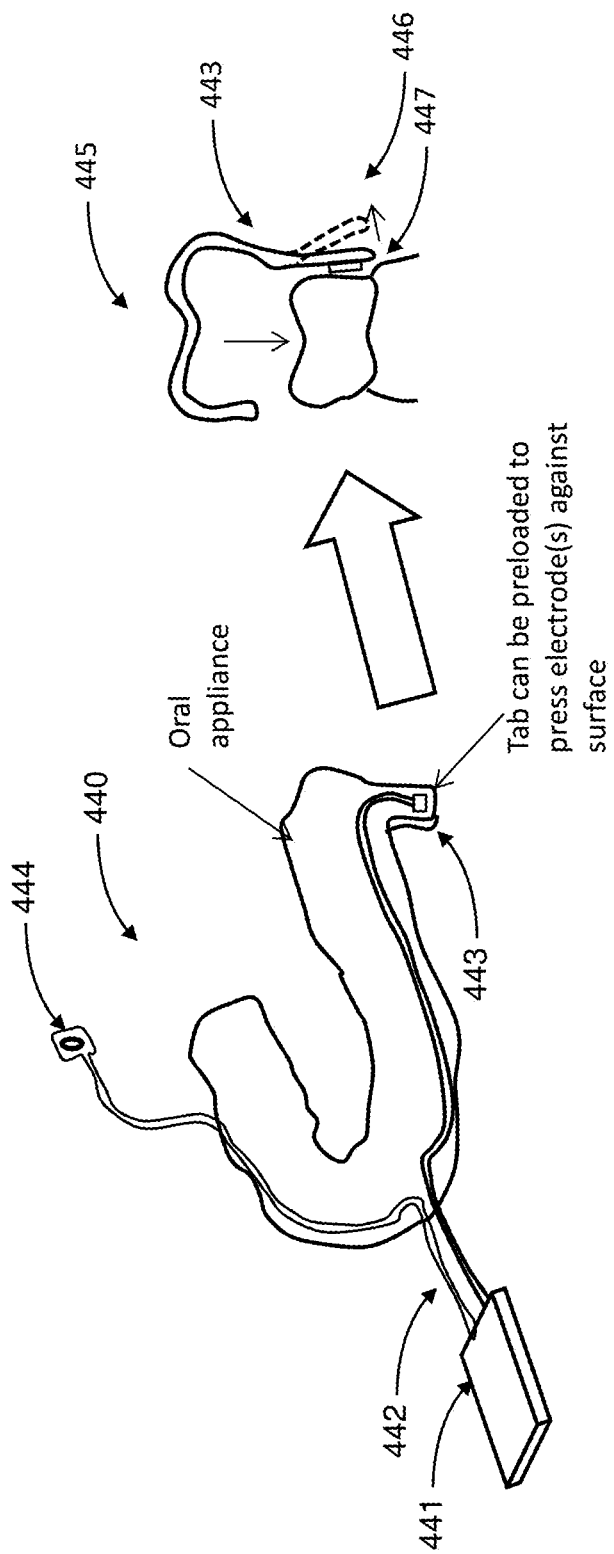
FIG. 50D illustrates examples of alternative, extended positions for sensors and drive electronics.

FIG. 50D illustrates examples of alternative, extended positions for sensors such as electrodes and drive electronics. The configurations of appliance shells and electrodes as shown in FIGS. 50A, 50B, and 50E-50G may be varied to place drive and measurement electronics and electrodes in alternative positions, as needed. For example, FIG. 50D illustrates an appliance 440 with certain variations of this type. The drive electronics 441 of appliance 440 are located outside of the shell, allowing an extra-oral measurement device to be connected. For example, the lead wires 442 may be connected to an external device while the patient sleeps, allowing the appliance to record impedance and other data without needing an internal power source. Electrodes may be located in a tab 443 extending from the gingival edge of the appliance, or even in a flexible, wired connection, such as electrode 444. Electrode 444 can be attached to an appliance or dental attachment on the opposite side of the patient's mouth as appliance 440, for example. This allows a greater flexibility in electrode configuration for performing a variety of measurements within the intraoral cavity of the patient. The tab 443 may be a preloaded tab with an electrode on an inner surface to allow contact to be maintained. As shown in the cross-section view 445 of a portion of appliance 440, the tab 443 is configured to elastically bend between a first configuration 446 away from the dentition and gums and a second configuration 447 pressing an electrode against the gums of the patient when the appliance is worn. The tab 443 is configured to apply a preloaded inwards force to keep the tab in the second configuration 447 to maintain electrical contact between the electrode and the gums of the patient. Such an electrode position is useful, for example, in measurements of impedance and other electrical characteristics of the periodontal ligaments (PDL).

Figure 50E:
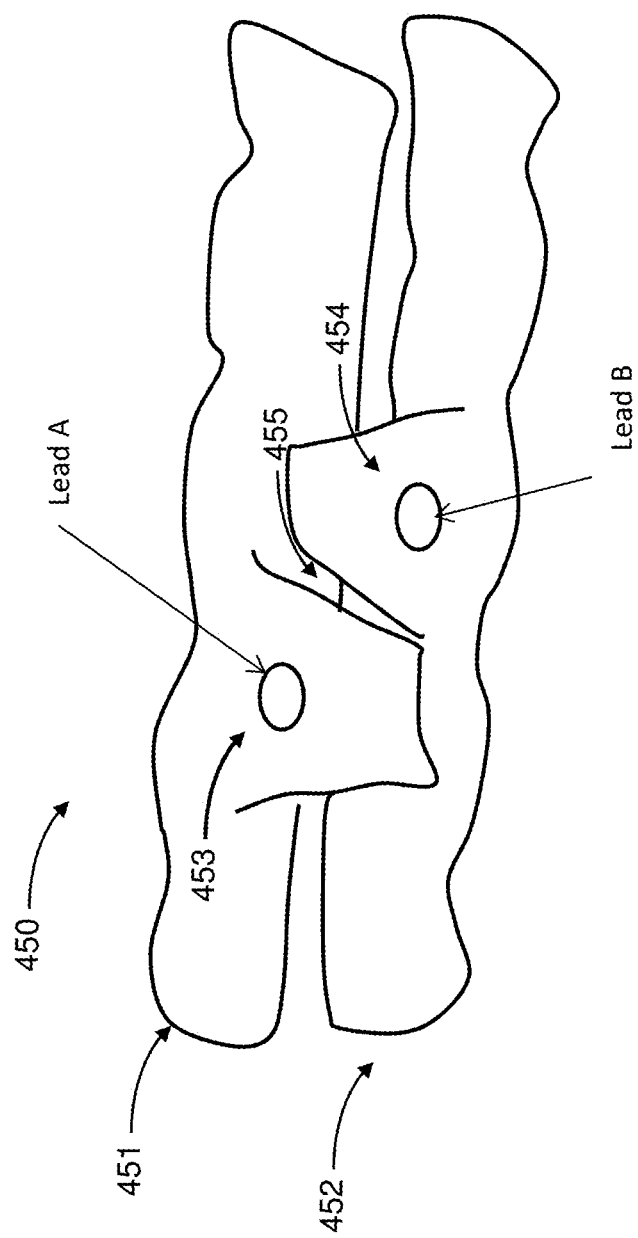
FIG. 50E illustrates an appliance comprising an upper shell to fit a patient's upper teeth and a lower shell to fit the patient's lower teeth, each shell comprising an sensor.

FIG. 50E illustrates an appliance comprising an upper shell to fit a patient's upper teeth and a lower shell to fit the patient's lower teeth, each shell comprising an sensor such as an electrode. The appliance 450 comprises an upper shell 451 comprising an upper electrode 453, and a lower shell 452 comprising a lower electrode 454. Each electrode is located on a protrusion of a mandibular advancement device for the treatment of a condition such as OSA, and the protrusions are configured to come into contact when each appliance is worn on the patient's respective upper and lower teeth to advance the mandible, for example. The interface 455 between protrusions can comprise conductive surfaces on each protrusion, such that the protrusions form an electrical contact, allowing each electrode to be controlled by a processor in one of the two shells. It will be understood that the electrodes 453 and 454 do not have to be located on the protrusions, but may instead be located elsewhere on their respective shells (for example, on opposite sides of the patient's mouth). In such a case, wires may be provided within the shells to connect the electrodes, the processor, and the interface 455 together.

Figure 50F:
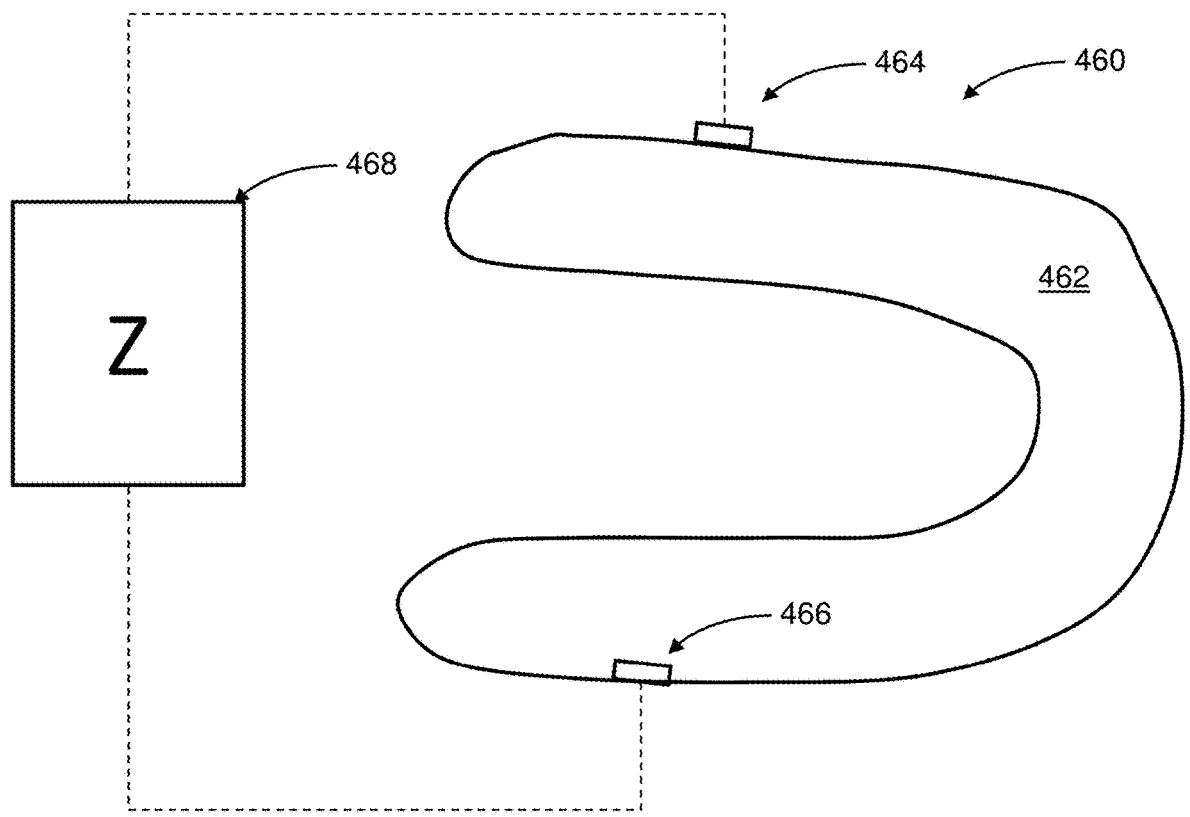
FIG. 50F illustrates an appliance configured to measure impedance between electrodes on opposite sides of the appliance shell.

FIG. 50F illustrates an appliance configured to measure physiological properties using electrodes on opposite sides of the appliance shell. The appliance 460 comprises an appliance shell 462 with two electrodes 464 and 466 on opposite sides of the shell. An impedance 468 may be measured between the electrodes, as illustrated in FIG. 50F in the form of a partial circuit diagram. The appliance shell 462 comprises control electronics including a processor and memory, for example as illustrated in FIG. 50C. The processor determines the impedance Z between electrodes, which is then used to determine one or more physiological characteristics of the patient; for example, airway cross-sectional area.

Figure 50G:
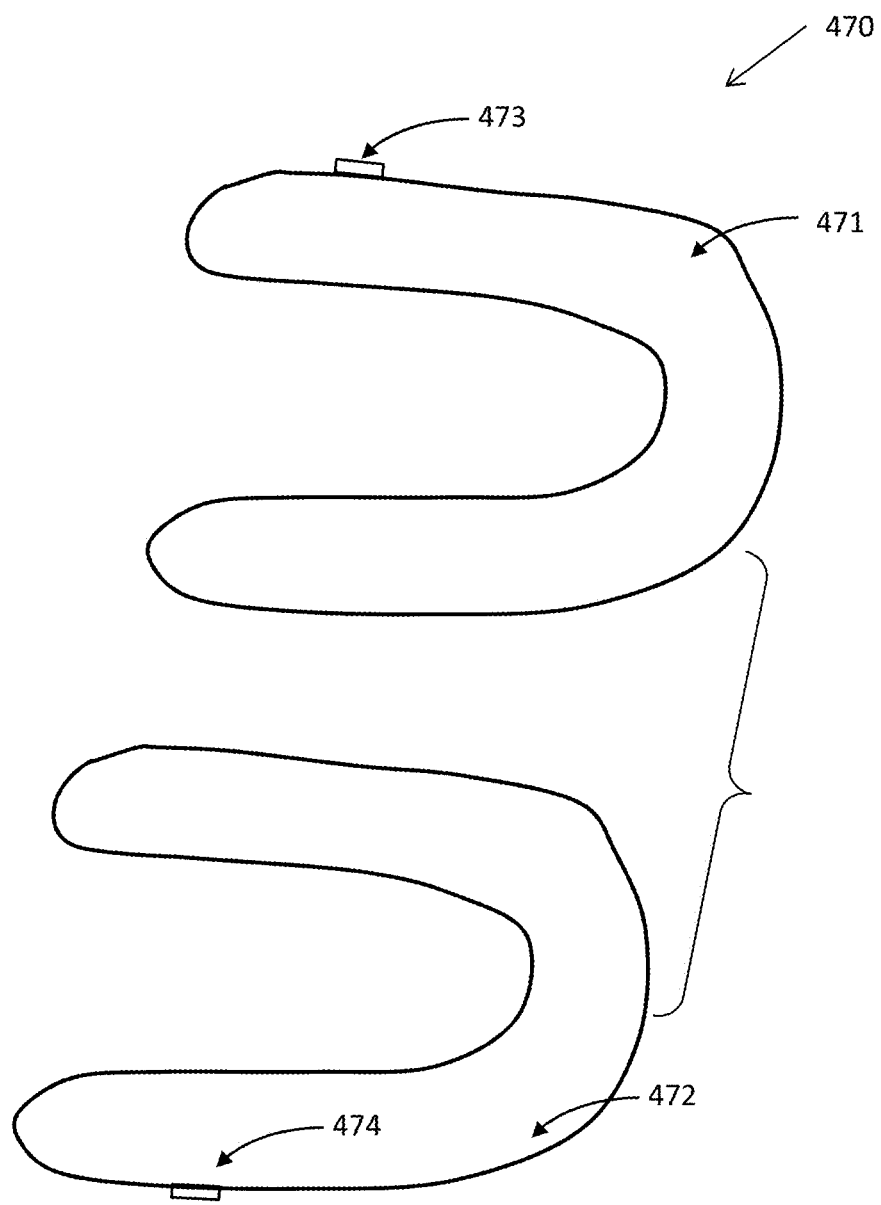
FIG. 50G illustrates an appliance with respective sensors on upper and lower shells, in which the sensors are inductively coupled.

FIG. 50G illustrates an appliance 470 with respective sensors on upper and lower shells, in which the electronic systems of the sensors are inductively coupled. The appliance 470 comprises an upper shell 471 with a sensor 472 and a lower shell 472 with a sensor 474. The two shells each comprise respective control electronics including respective processors, power sources, and measurement and drive electronics. The two shells are not configured to form direct electrical contact; instead, the electronics of the upper and lower shells are inductively coupled, such that each responds to transient electrical pulses emitted from the other. The sensors of FIG. 50G can be configured with one sensor being a transmitter and one being a receiver; for example, an acoustic transmitter and receiver may be used. In this manner, measurements may be performed relating signals to and from sensors in each respective shell without requiring an electrical pathway connecting the upper and lower shell electronics.

In cases in which sensors are located on separate upper and lower appliance shells the two shells may be coupled in various ways to enable coordinated measurement. For example, conductive coupling can be achieved in various ways. A wired connection can be made between opposing arches. In some embodiments, a single, monolithic appliance may be more practical than an appliance for both arches. However, where intermittent sensing is acceptable, conductive connectors can be placed on known contact points, such as is illustrated in FIG. 50E. In another example of coupling, a conductive articulating rod such as a Herbst-style rod can be included between shells to provide a conductive path. Other methods of coupling directly include stretchable conductors, which can function like orthodontic elastics between appropriate hooks or buttons, or implanted wires within the mouth of the patient, such as subcutaneous wires in the cheek or adhesive wires attached on the inner surface of the intraoral cavity.

Figure 51A:
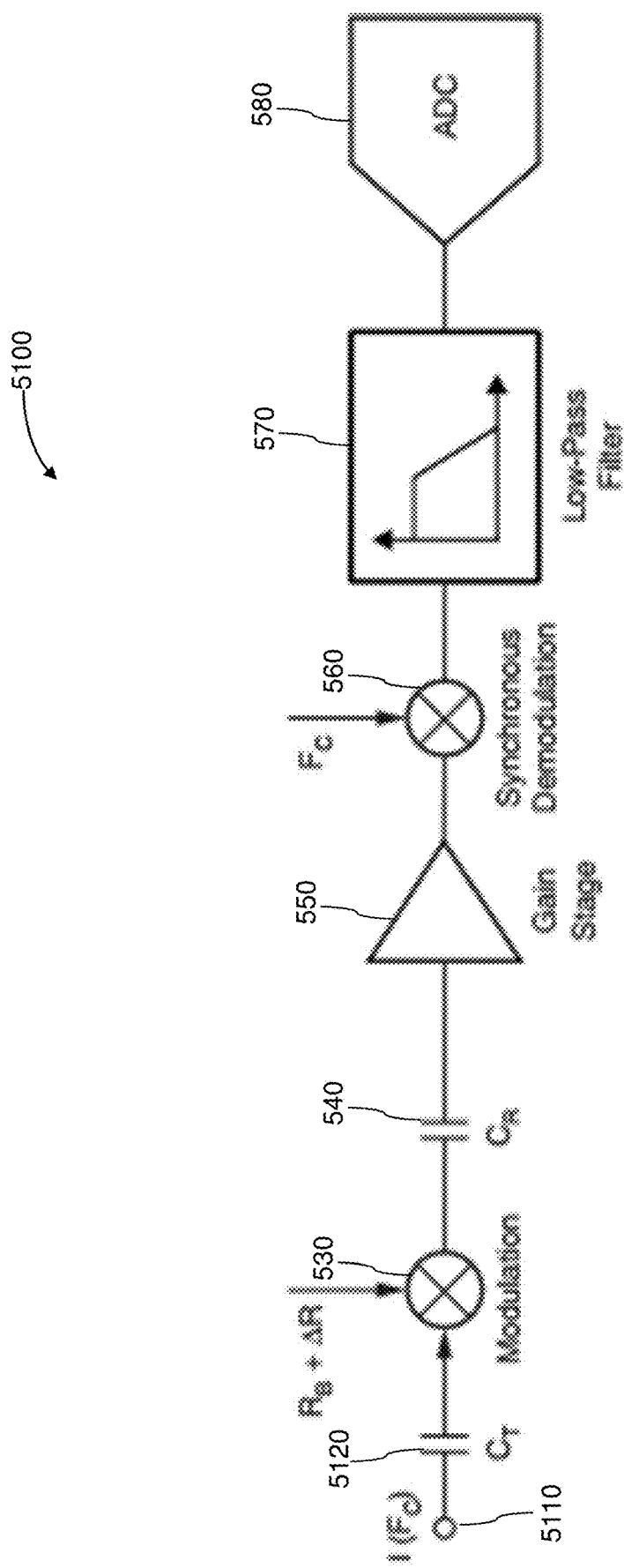
FIG. 51A illustrates a block diagram of a signal chain for performing impedance measurements with the appliances disclosed herein.

FIG. 51A illustrates a block diagram of a signal chain 5100 for performing impedance measurements with the appliances disclosed herein. The driver electronics provide a current 5110 to an electrode characterized by a carrier frequency Fc. To eliminate DC current, the current transmitting electrode is screened from the current source by a high-pass filter in the form of a capacitor 5120. The electrode contacts the patient's intraoral cavity, which provides modulation 530 at low frequencies, corresponding to variations in electrical impedance. This impedance can be modeled as a baseline impedance RB plus a variable impedance ΔR. The modulation is due to changes in ΔR, for example, arising from changes in airway cross-sectional area as the patient breathes. The modulated signal is received at the receiving electrode, which is also screened by a high-pass filter in the form of a capacitor 540. The received signal is then amplified by a gain stage 550. Thereafter, the signal is synchronously demodulated 560 to remove the carrier frequency Fc. Remaining high-frequency components are removed with a low-pass filter 570, producing the final signal to be measured. An analog-to-digital converter 580 then converts the signal to a digital signal, which is processed by a processor that records the resulting measurement data to a non-transitory computer-readable medium.

When the signal chain disclosed in FIG. 51A is applied to monitor physiological characteristics within the mouth of a patient, it is important to use signal frequencies and amplitudes that do not irritate or harm the patient. For inductive measurements with electrodes, safe ranges for current may be about 100 µA or less. Carrier frequencies used to modulate the signals can be chosen to appropriately minimize noise; for example, a carrier frequency of about 10 kHz is useful for many applications. The signal chain disclosed in FIG. 51A may be applied to systems using sensors other than electrodes, replacing the electrodes described above with the appropriate sensor, such as a transducer, a piezo-electric crystal, or an actuator/accelerometer pair. The impedance modulation will correspondingly be replaced with a modulation of the signal to which the particular sensor is sensitive. For systems applying mechanical energy, the mechanical energy applied can be kept less than about 1 N for continuous force. For transient forces such as periodic forces, larger forces may be applied; for example, an amplitude of about 5 N or less can be applied for transient force measurements.

Figure 51B:
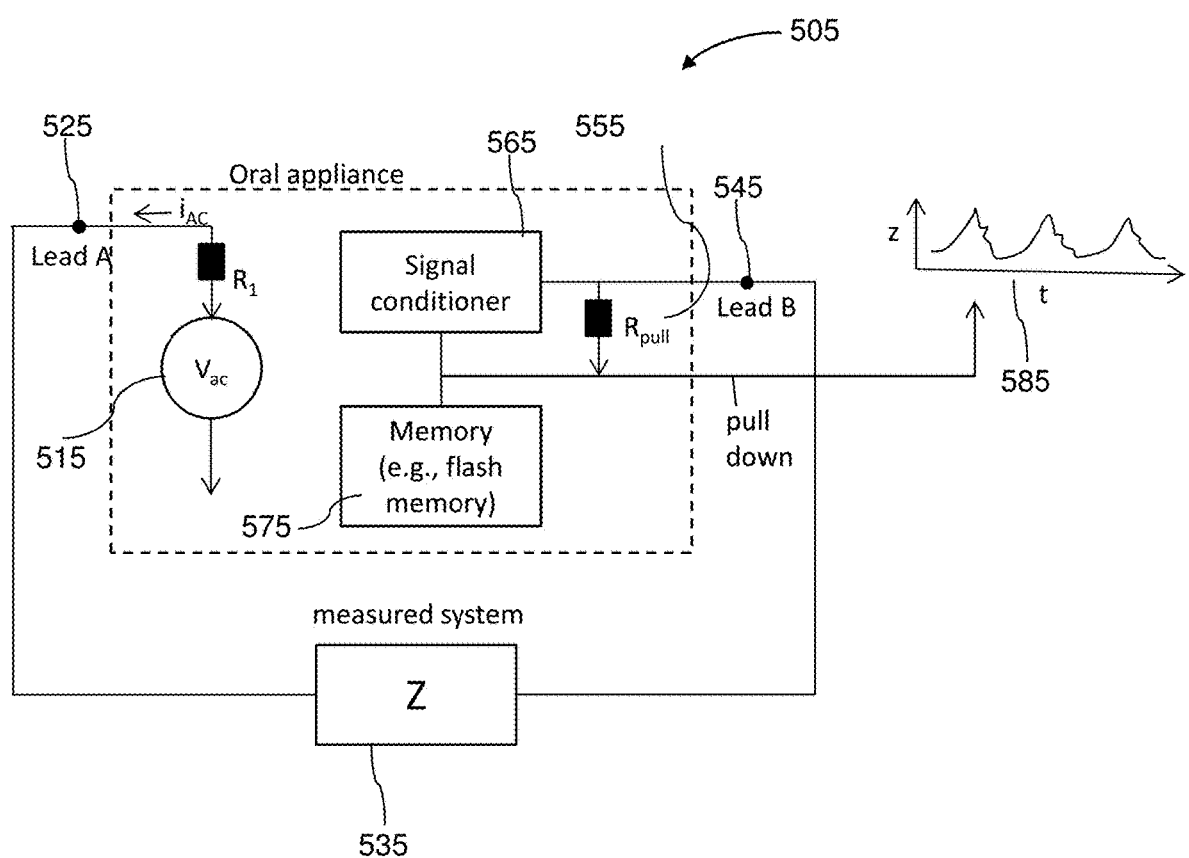
FIG. 51B shows a schematic diagram of an oral appliance comprising a plurality of electrodes for measuring the impedance of a system such as the intraoral cavity or airway of a patient.

FIG. 51B shows a schematic diagram of an oral appliance comprising a plurality of electrodes for measuring the impedance of a system such as the intraoral cavity or airway of a patient. A power source 515 supplies an alternating current to a first electrode lead 525. The electrode lead 525 can be brought into contact with a system 535 to be measured, such as the intraoral cavity of a patient. The voltage drop between lead 525 and lead 545 varies based on the impedance of the system 535, in a manner approximated by Ohm's law (V=I*Z); accordingly, the relationship between the voltage drop and current flow between electrodes 525 and 545 can be used to determine the impedance of the system 535. Each of the voltage and the current can be measured using conventional methods, e.g., with voltmeters and/or ammeters. A pull-up or pull-down resistor 555 can be included to ensure the incoming electrical signal has an appropriate voltage reference. The incoming AC signal from electrode lead 545 is then demodulated at signal conditioner 565, with gain applied as needed to amplify the signal. Remaining high-frequency elements are removed with a low-pass filter, and the signal is then recorded to memory 575 for analysis. As data are accumulated over time, a data plot 585 of impedance vs time can be generated for analysis by the processor. The data can also be transmitted to an external device such as a mobile device for display and analysis, e.g., by a medical professional.

Figure 52:
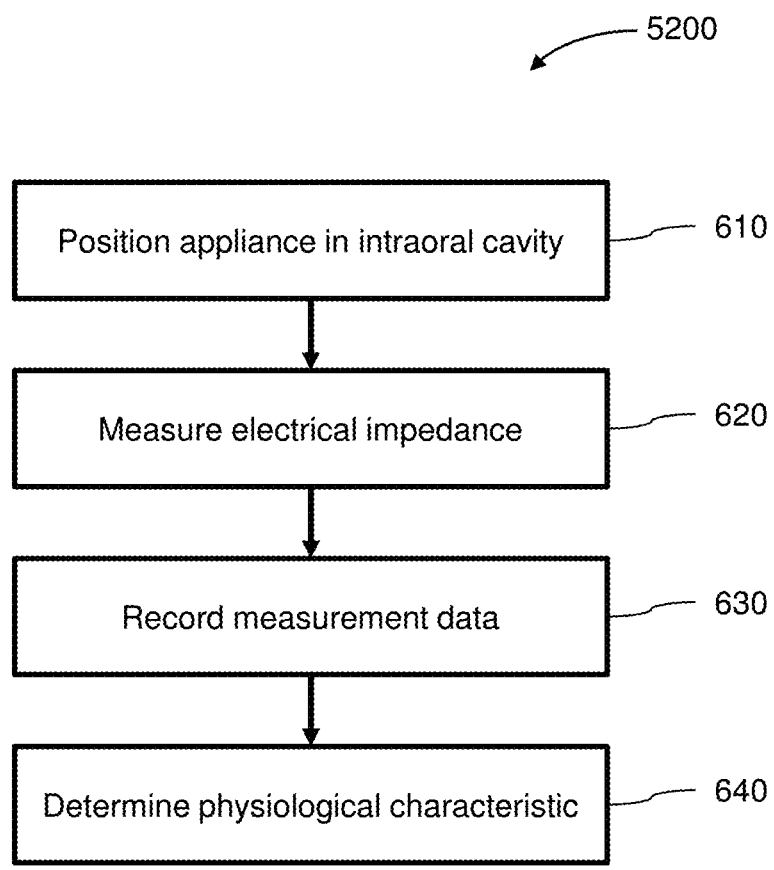
FIG. 52 illustrates a method for monitoring a physiological characteristic of a patient using an appliance as disclosed herein.

FIG. 52 illustrates a method 5200 for monitoring a physiological characteristic of a patient using an intraoral appliance as disclosed herein.

In step 610, the appliance is positioned in the mouth of a patient. The appliance may comprise, for example, an appliance shell, or even a plurality of appliance shells, such as those disclosed herein. The appliance comprises a plurality of electrodes disposed within the one or more shells, and configured to make electrical contact with the patient's intraoral cavity when the intraoral appliance is worn by the patient.

In step 620, an impedance measurement is performed by a processor coupled to the electrodes. The impedance measurement may, for example, be performed using a signal chain such as signal chain 500. The variation of impedance due to physiological changes of the patient such as changes in airway occlusion causes a modulation of a current signal. After amplification and demodulation of a carrier frequency of the current signal, the remaining signal can be sent through a low-pass filter to retrieve an analog signal. The variation of that signal corresponds to variation in impedance. An analog-to-digital converter can generate signal data readable by the processor as a sequence of signal values over time, and the sequence contains information from which impedance variation can be determined. For example, variations in impedance due to breathing can be determined by detecting signal variations with substantially similar frequencies to the breathing rate.

In step 630, the processor records data to memory corresponding to the impedance measurement. Optionally, the processor may cause a transmitter to transmit the data to a remote receiver to be recorded in memory outside the appliance. For example, a mobile device or other computing device may communicate with the processor using wired or wireless technology (such a Bluetooth, WiFi, or cellular communication, for example.)

In step 640, a physiological characteristic is determined based on the impedance measurement data recorded in memory. For example, the physiological characteristic may be airway diameter, airway volume, airway resistance, lung fluid level, soft tissue crowding, breathing rate, muscle activity, ionic composition of saliva, or ionic composition of oral mucosa, or a combination thereof. Airway diameter, volume, and resistance can be determined by measuring variation in far-field impedance as measured by the electrodes. These size changes can be used as indicators of soft-tissue crowding. The signal can be isolated by detecting impedance variations correlated with patient breathing, for example. Breathing rate may be determined by detecting slow, periodic variations in overall impedance with time periods on the order of seconds. Lung fluid level can be determined by measuring properties of returning electrical current pulses, in particular their delay time and phase. Muscle activity, ionic composition of saliva, or ionic composition of oral mucosa can be measured with near-field electrodes: changes in ionic composition change electrical impedance of the intervening fluid, and muscle activity generates electrical currents that can be detected with the electrodes.

Figure 53:
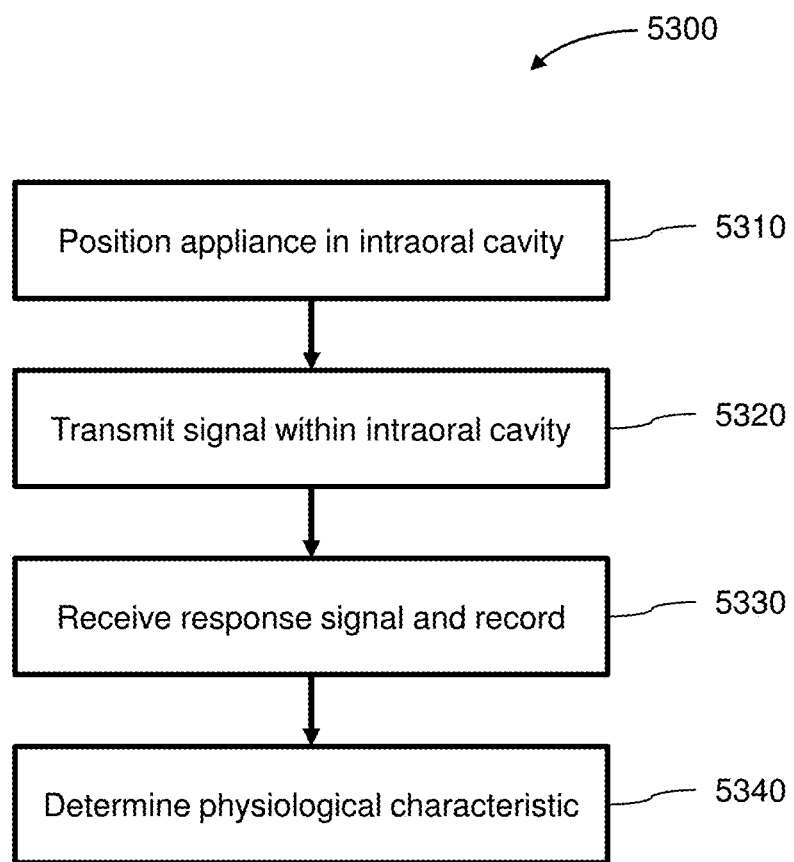
FIG. 53 illustrates a method for monitoring a characteristic of a patient's intraoral cavity or airway.

FIG. 53 illustrates a method 5300 for monitoring a characteristic of a patient's intraoral cavity or airway using transmitter-receiver pairs disposed within an intraoral appliance.

In step 5310, the appliance is positioned in the mouth of a patient. The appliance may comprise, for example, an appliance shell, or even a plurality of appliance shells, such as those disclosed herein. The appliance comprises a transmitter and a receiver disposed within the one or more shells. For example, the transmitter and the receiver may be positioned in place of the electrodes in appliances substantially as described in FIGS. 50A-50F. The transmitter and receiver may also be disposed in a pair of shells with inductively coupled electronics, as disclosed in FIG. 50G.

In step 5320, the transmitter transmits a signal within the intraoral cavity. Examples of transmitters and respective transmitted signals include an electrode transmitting electrical pulses, a transducer transmitting acoustic waves, and an actuator transmitting mechanical force.

In step 5330, a response signal is received and processed by a processor, then recorded to memory. The response signal can arise from an interaction between the transmitted signal and portions of the patient's intraoral cavity and/or airway, such as a scattering, reflection, or stimulation of tissue or fluids, for example. The response signal is received by a receiving sensor. Examples of receiving sensors and respective received signals include an electrode receiving piezoelectric pulses, a transducer receiving reflected acoustic waves, and an accelerometer detecting acceleration. The received signal contains information about the tissues and/or fluids it traveled through that can be analyzed to determine physiological characteristics; for example, modulations of the amplitude, frequency and phase of the received signals can correspond to corresponding changes in the transmission medium of the patient's intraoral cavity or airway.

In step 5340, a physiological characteristic is determined based on the sensor measurement data recorded in memory. The determined physiological characteristic can be, for example, compression response of bone and collagen; temporomandibular joint articulation; grinding or clenching of teeth; decline in upper airway muscle activity; stiffness of tooth-PDL structure; tooth, root, and/or PDL health; root structures based on acoustic responses of surrounding tissue; oral cavity or upper airway shape and size; soft tissue crowding; opening or closing of the mouth; or mandibular protrusion or retrusion. These physiological characteristics may be respectively determined using the appropriate sensors and physiological relationships as described above regarding FIGS. 50A-50G.

Figure 54:
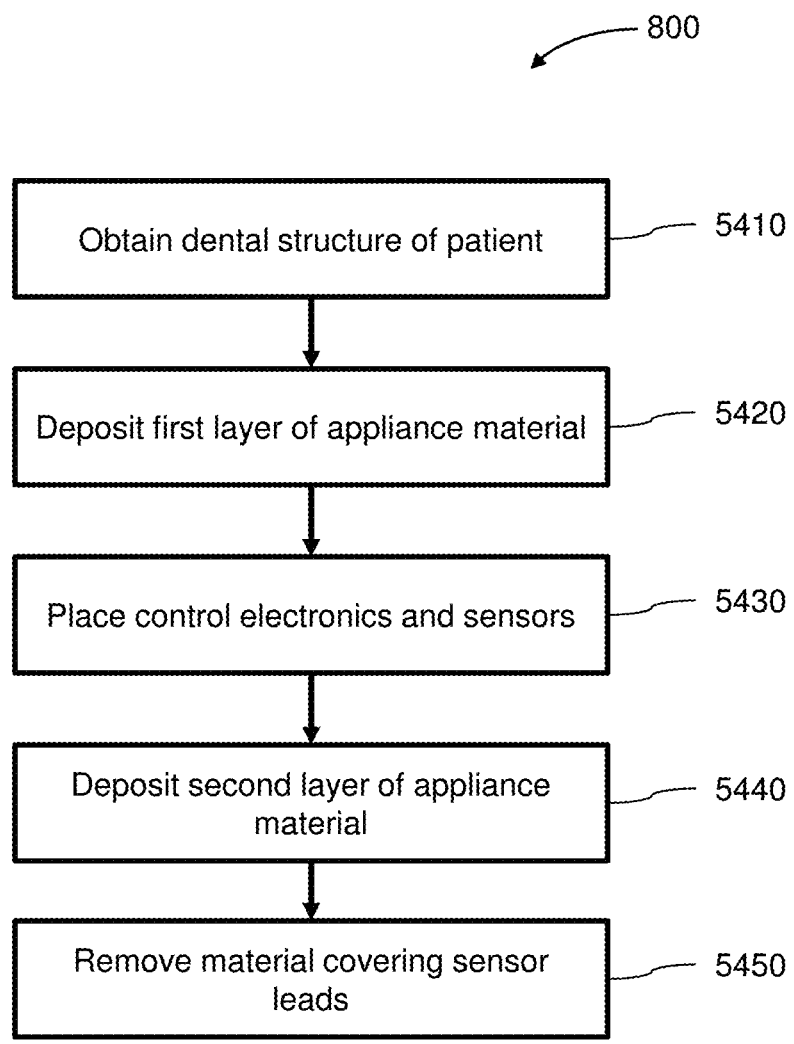
FIG. 54 illustrates a method of manufacturing an appliance comprising sensors and control electronics.

FIG. 54 illustrates a method of manufacturing an appliance comprising sensors and control electronics 5400.

In step 5410, the dental structure of the patient is obtained. This structure may be in the form of a physical mold or model, for example, or a 3D image of the patient's dentition.

In step 5420, a first layer of appliance material is deposited. This deposition may be, for example, the application of a thermoformed layer of plastic over a mold. Alternatively, material may be deposited by direct fabrication, such as using a 3D printer, according to a 3D model of the appliance generated to fit the teeth of the patient, based on the 3D image of the patient's dentition in step 5410. In some embodiments, steps 5420 and 5440 can be combined into a single step in which the appliance shell is directly fabricated around the control electronics and sensors of step 5430.

In step 5430, control electronics and sensors are placed over the first layer of appliance in appropriate locations. Wiring is provided as needed to connect each component of the sensing system. In this step, carbon fiber can be incorporated into the aligner to create an antenna for wireless communication to an external receiver. Multiple electrodes or other sensors can be provided to enhance signal acquisition; for example, in a manner similar to neuroelectrodes used for electroencephalogram measurements.

In step 5440, a second layer of appliance material is deposited, as in step 5420. The second layer, in combination with the first layer, envelops the control electronics and sensors.

In step 5450, any material covering sensor leads can be removed, if necessary. For example, a robotic mill or laser cutter may be used to remove appliance material covering electrodes, transducers, actuators, accelerometers, etc., so as to provide a clear contact with the appropriate part of the patient's mouth when the appliance is worn.

Figure 55:
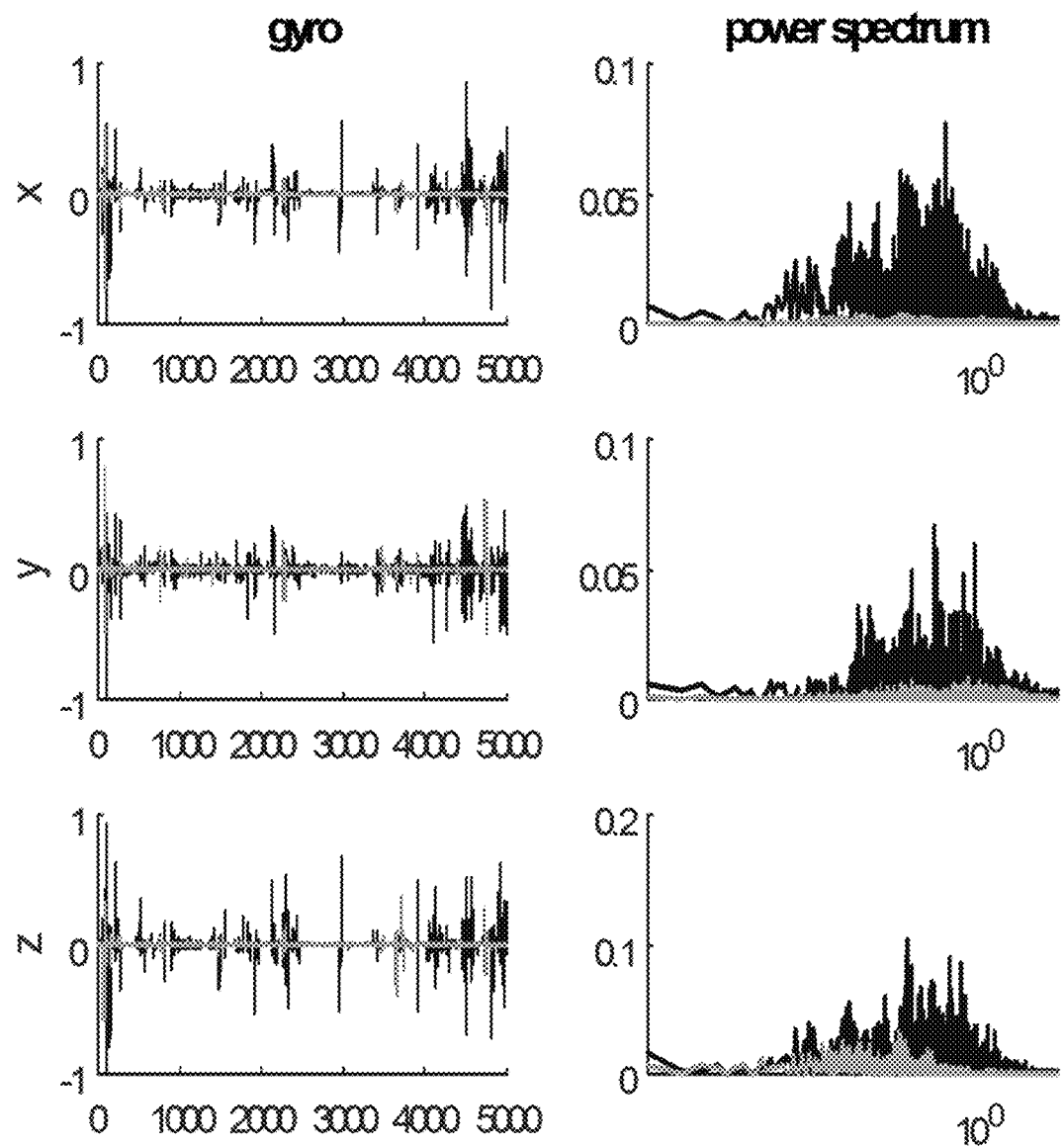
FIG. 55 illustrates exemplary rotational velocity data collected with a gyroscopic accelerometer coupled to the maxilla of a patient.

In order to better isolate signals relevant to the physiological characteristics to be measured, multiple sensor systems can be combined using a sensor fusion technique. For example, as discussed above, airway width variation is correlated with patient breathing. Patient breathing rate can be determined using an accelerometer disposed within the intraoral appliance. FIG. 55 illustrates exemplary rotational velocity data collected with a gyroscopic accelerometer coupled to the maxilla of a patient. The grey spectra illustrate rotational velocity data a sensor loosely coupled to the body, near the hip. The black spectra illustrate corresponding data from a sensor coupled to the jaw of the patient via an appliance. The left spectra illustrate the raw data in each of the x, y, and z dimensions, while the right spectra illustrate the same data transformed into Fourier space and displayed as a power spectrum. The power spectrum of the black curve, measuring jaw movement, shows a maximum somewhat below 1 Hz, corresponding to the breathing rate of the patient. By contrast, the measurement at the patient's hip shows only a weak signal. Thus, intraoral measurement can be used to measure a signal sensitive to a patient's breathing rate. Using this measured breathing rate, it is possible to isolate the effect of airway width variation on impedance measurements from electrodes by detecting impedance variations with substantially matching frequencies. Since impedance measurements are also sensitive to the breathing of the patient, impedance and acceleration signal can be measured by an intraoral appliance and cross-validated to provide a breathing rate measurement with enhanced accuracy.

In some embodiments, an appliance comprising sensors as disclosed herein can be a treatment appliance, such as an orthodontic appliance or an appliance for the treatment of sleep apnea. In such an appliance, the monitoring of physiological conditions can comprise an assessment of treatment efficacy. For example, sleep apnea can be treated with the intraoral appliance, and the effectiveness can be monitored by tracking the resulting change in airway diameter or volume. The movement of teeth due to orthodontic forces can also be measured, such as by monitoring the stiffness of a tooth-PDL structure to which orthodontic forces are being applied by the appliance.

Appliances having teeth receiving cavities such as those disclosed herein include appliances that receive and reposition teeth, e.g., via application of force due to appliance resiliency. Examples of such appliances are generally illustrated with regard to FIG. 1A. FIG. 1A illustrates an exemplary tooth repositioning appliance or aligner 1000 that can be worn by a patient in order to achieve an incremental repositioning of individual teeth 1002 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 1004 on teeth 1002 with corresponding receptacles or apertures 1006 in the appliance 1000 so that the appliance can apply a selected force on the tooth. Exemplary appliances, including those utilized in the Invisalign® System, are described in numerous patents and patent applications assigned to Align Technology, Inc.

including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309, 215 and 6,830,450.

FIG. 1B illustrates a tooth repositioning system 1010 including a plurality of appliances 1012, 1014, 1016. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 1010 can include a first appliance 1012 corresponding to an initial tooth arrangement, one or more intermediate appliances 1014 corresponding to one or more intermediate arrangements, and a final appliance 1016 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 1A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein. Tooth movement of the crown greater than the movement of the root can be referred to as tipping. Equivalent movement of the crown and root can be referred to as translation. Movement of the root greater than the crown can be referred to as root movement.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for monitoring a characteristic of a patient's intraoral cavity or airway, the apparatus comprising:
   an intraoral appliance shaped to receive the patient's teeth and comprising a transmitter and a receiver; and
   one or more processors configured to:
   cause the transmitter to emit a signal within the patient's intraoral cavity,
   measure a signal returning from the patient's intraoral cavity or airway in response to the emitted signal using the receiver, and
   determine the characteristic of the patient's intraoral cavity or airway based on the measured signal.

2. The apparatus of claim 1, wherein the characteristic comprises one or more of: airway diameter, airway volume, airway resistance, lung fluid level, soft tissue crowding, breathing rate, muscle activity, ionic composition of saliva, or ionic composition of oral mucosa.

3. The apparatus of claim 1, wherein the characteristic is related to a sleep disorder of the patient, the sleep disorder comprising one or more of sleep apnea, snoring, or bruxism.

4. The apparatus of claim 1, wherein the emitted signal comprises electrical energy, acoustic energy, or mechanical energy.

5. The apparatus of claim 4, wherein the emitted signal comprises electrical energy and wherein the one or more processors is configured to determine the characteristic of the patient's intraoral cavity or airway based on the measured signal by determining an electrical impedance of the patient's intraoral cavity or airway based on the measured signal.

6. The apparatus of claim 1, wherein the emitted signal comprises a first waveform, the measured signal comprises a second waveform, and wherein the one or more processors is configured to determine the characteristic of the patient's intraoral cavity or airway based on the measured signal by identifying a change between the first and second waveforms.

7. The apparatus of claim 1, wherein the one or more processors are disposed on or within the intraoral appliance.

8. The apparatus of claim 1, wherein the intraoral appliance comprises a polymeric shell having a plurality of teeth-receiving cavities.

9. A method for monitoring a characteristic of a patient's intraoral cavity or airway, the method comprising:
   positioning an intraoral appliance in the patient's intraoral cavity, the intraoral appliance shaped to receive the patient's teeth and comprising a transmitter and a receiver;
   causing the transmitter to emit a signal within the patient's intraoral cavity;
   measuring a signal returning from the patient's intraoral cavity or airway in response to the emitted signal using the receiver; and
   determining the characteristic of the patient's intraoral cavity or airway based on the measured signal.

10. The method of claim 9, wherein the characteristic comprises one or more of:
    airway diameter, airway volume, airway resistance, lung fluid level, soft tissue crowding, breathing rate, muscle activity, ionic composition of saliva, or ionic composition of oral mucosa.

11. The method of claim 9, wherein the characteristic is related to a sleep disorder of the patient, the sleep disorder comprising one or more of sleep apnea, snoring, or bruxism.

12. The method of claim 9, wherein the emitted signal comprises electrical energy, acoustic energy, or mechanical energy.

13. The method of claim 9, wherein the emitted signal comprises electrical energy and wherein determining comprises determining an electrical impedance of the patient's intraoral cavity or airway based on the measured signal.

14. The method of claim 9, wherein the emitted signal comprises a first waveform, the measured signal comprises a second waveform, and wherein determining comprises identifying a change between the first and second waveforms.

15. The method of claim 9, wherein the causing, measuring, and determining steps are performed by one or more processors disposed on or within the intraoral appliance.

16. The method of claim 9, wherein the intraoral appliance comprises a polymeric shell having a plurality of teeth-receiving cavities.

17. A device for monitoring usage of an intraoral appliance, the device comprising:
    an appliance shell comprising a plurality of teeth receiving cavities;
    one or more vibration sensors operably coupled to the appliance shell and configured to generate sensor data of intraoral vibration patterns; and
    a processor operably coupled to the one or more vibration sensors and configured to process the sensor data so as to determine whether the intraoral appliance is being worn on a patient's teeth, wherein the processor determines whether the intraoral appliance is being worn by comparing the intraoral vibration patterns to patient-specific intraoral vibration patterns.

* * * * *